US011873325B2

(12) United States Patent
Berry et al.

(10) Patent No.: US 11,873,325 B2
(45) Date of Patent: Jan. 16, 2024

(54) NUCLEIC ACID ENCODING SM1 RESISTANCE TO ORANGE WHEAT BLOSSOM MIDGE AND METHOD OF USE

(71) Applicant: LIMAGRAIN EUROPE, Saint-Beauzire (FR)

(72) Inventors: Simon Timothy Berry, Litcham (GB); Jordi Comadran, Gerzat (FR); Sebastien Specel, Gerzat (FR)

(73) Assignee: LIMAGRAIN EUROPE, Saint-Beauzire (FR)

( * ) Notice: Subject to any disclaimer, the term of this patent is extended or adjusted under 35 U.S.C. 154(b) by 1210 days.

(21) Appl. No.: 16/340,451

(22) PCT Filed: Oct. 10, 2017

(86) PCT No.: PCT/EP2017/075849
§ 371 (c)(1),
(2) Date: Apr. 9, 2019

(87) PCT Pub. No.: WO2018/069343
PCT Pub. Date: Apr. 19, 2018

(65) Prior Publication Data
US 2020/0140497 A1 May 7, 2020

(30) Foreign Application Priority Data
Oct. 10, 2016 (EP) ..................................... 16306334

(51) Int. Cl.
*C12Q 1/68* (2018.01)
*C12N 15/82* (2006.01)
*C07K 14/415* (2006.01)
*C12N 15/90* (2006.01)
*C12Q 1/6895* (2018.01)

(52) U.S. Cl.
CPC ........ *C07K 14/415* (2013.01); *C12N 15/8286* (2013.01); *C12N 15/902* (2013.01); *C12Q 1/6895* (2013.01); *C12Q 2600/13* (2013.01)

(58) Field of Classification Search
CPC .............. C07K 14/415; C12N 15/8286; C12N 15/902; C12Q 1/6895; C12Q 2600/13
See application file for complete search history.

(56) References Cited

U.S. PATENT DOCUMENTS

2020/0140497 A1* 5/2020 Berry .................. C12N 15/902

OTHER PUBLICATIONS

Chen, T., 2013. Effect of Sm1 on End-use Quality of Durum Wheat (*Triticum turgidum* L. Var Durum) (Doctoral dissertation, University of Saskatchewan). (Year: 2013).*

Genbank Accession No. LR877313, Triticum aestivum genome assembly, chromosome: 2B (submitted Aug. 11, 2020, retrieved on Dec. 13, 2022 from http://www.ncbi.nlm.nih.gov/nuccore/LR877313). (Year: 2020).*
Randhawa et al., 2013. Application of molecular markers to wheat breeding in C anada. Plant Breeding, 132(5), pp. 458-471. (Year: 2013).*
Thambugala et al., 2021. Genetic analysis of oviposition deterrence to orange wheat blossom midge in spring wheat. Theoretical and Applied Genetics, 134(2), pp. 647-660. (Year: 2021).*
Zhang et al., 2020. Molecular mapping of major QTL conferring resistance to orange wheat blossom midge (Sitodiplosis mosellana) in Chinese wheat varieties with selective populations. Theoretical and Applied Genetics, 133(2), pp. 491-502. (Year: 2020).*
Altschul SF, Madden TL, Schaffer AA, Zhang J, Zhang Z, Miller W, Lipman DJ (1997) Gapped BLAST and PSI-BLAST: a new generation of protein database search programs. Nucleic Acids Res. 25: 3389-3402.
Altschul SF, Wootton JC, Gertz EM, Agarwala R, Morgulis A, Schaffer AA, Yu YK (2005) Protein database searches using compositionally adjusted substitution matrices. The FEBS Journal 272: 5101-5109.
Anderson OD, Greene FC (1989) The characterization and comparative analysis of high-molecular-weight glutenin genes from genomes A and B of hexaploid bread wheat. Theoretical and Applied Genetics 77: 689-700.
Anon (2016) Orange wheat blossom midge. AHDB Information sheet No. 53 Summer 2016 (https://cereals.ahdb.org.uk/).
Bailey TL and Elkan C (1994) Fitting a mixture model by expression maximization to discover in biopolymers. Proceedings of the International Conference on Intelligent Systems for Molecular Biology 2: 28-36.
Birkett MA, Bruce TJA, Martin JL, Smart LE, Oakley J, Wadhams LJ (2004) Responses of female orange wheat blossom midge to wheat panicle volatiles. Journal of Chemical Ecology 30: 1319-1328.
Blake NK, Stougaard RN, Weaver DK, Sherman JD, Lanning SP, Narouka Y, Xue Q, Martin JM, Talbert LE (2011) Identification of a quantitative trait locus for resistance to Sitodiplosis mosellana (Géhin), the orange wheat blossom midge, in spring wheat. Plant Breeding 130: 25-30.
Bo Du, Zhang W, Liu B, Hu J, Wei J, Shi Z, He R, Zhu L, Chen R, Han B, He G (2009) Identification and characterization of Bph14, a gene conferring resistance to brown planthopper in rice. Proceedings of the National Academy of Sciences USA 106: 22163-22168.
Bruce TJ, Hooper AM, Ireland L, Jones OT, Martin JL, Smart LE, Oakley J, Wadhams LJ (2007) Development of a pheromone trap monitoring system for orange wheat blossom midge, Sitodiplosis mosellana, in the UK. Pest Management and Science 63: 49-56.
Chavalle S, Censier F, San Martin y Gomez G, De Profta M (2015) Protection of winter wheat against orange wheat blossom midge, Sitodiplosis mosellana (Géhin) (Diptera: Cecidomyiidae): efficacy of insecticides and cultivar resistance. Pest Management Science 71: 783-790.

(Continued)

Primary Examiner — Teresa E Strzelecka
Assistant Examiner — Olayinka A Oyeyemi
(74) Attorney, Agent, or Firm — Arrigo, Lee, Guttman & Mouta-Bellum LLP

(57) ABSTRACT

The present invention relates to nucleic acids encoding for proteins correlated with the resistance of the Sm1 locus in wheat and uses of these nucleic acids, in particular for conferring or improving resistance to orange wheat blossom midge (OWBM) in a plant.

11 Claims, 3 Drawing Sheets

(56) References Cited

OTHER PUBLICATIONS

Christensen AH, Quail PH (1996) Ubiquitin promoter-based vectors for high-level expression of selectable and/or screenable marker genes in monocotyledonous plants. Transgenic Research 5: 213-218.

Depigny-This D, Raynal M, Aspart L, Delseny M, Grellet F (1992) The cruciferin gene family in radish. Plant Molecular Biology 20: 467-479.

Ding H, Lamb RJ, Ames N (2000) Inducible production of phenolic acids in wheat and antibiotic resistance to Sitodiplosis mosellana. Journal of Chemical Ecology 26: 969-985.

Doane JF, Olfert OO, Elliott RH, Hartley S, Meers S (2013) Sitodiplosis mosellana (Géhin), orange wheat blossom midge (Diptera: Cecidomyiidae). In "Biological control programmes in Canada 2001-2012". Eds PG Mason & DR Gillespie. Chapter 39, pp. 272-276.

Dogimont C, Chovelon V, Pauquet J, Boualem A, Bendahmane A (2014) The Vat locus encodes for a CC-NBS-LRR protein that confers resistance to Aphis gossypii infestation and A. gossypii-mediated virus resistance. The Plant Journal 80: 993-1004.

Elliot RH, Mann LW (1996) Susceptibility of red spring wheat, *Triticum aestivum* L. cv. Katepwa, during heading and anthesis to damage by wheat midge, Sitodiplosis mosellana (Géhin) (Diptera: Cecidomyiidae). The Canadian Entomol ogist 128: 367-375.

Gharalari AH, Fox SL, Smith MAH, Lamb RJ (2009a) Oviposition deterrence in spring wheat, Triticum aestivum, against orange wheat blossom midge, Sitodiplosis mosellana: implications for inheritance of deterrence. Entomologia Experimentalis et Applicata 133: 74-83.

Gharalari AH, Smith MAH, Fox SL, Lamb RJ (2011) Volatile compounds from non-preferred wheat spikes reduce oviposition by Sitodiplosis mosellana. The Canadian Entomologist 143: 388-391.

Harris MO, Stuart JJ, Mohan M, Nair S, Lamb RJ, Rohfritsch O (2003) Grasses and gall midges: Plant defense and Insect adaptation. Annual Review of Entomology 48: 549-577.

Ishida Y, Saito H, Ohta S, Hiei Y, Komari T, Kumashiro T (1996) High efficiency transformation of maize (*Zea mays* L.) mediated by Agrobacterium tumefaciens. Nature Biotechnology, 14: 745-750.

Jouanin L, Guerche P, Pamboukdjian N, Tourneur C, Casse Delbart F, Tourneur J (1987) Structure of T-DNA in plants regenerated from roots transformed with Agrobacterium rhizogene strain A4. Molecular and General Genetics 206: 387-392.

Kassa MT, Haas S, Schliephake E, Lewis C, You FM, Pozniak CJ, Kramer I, Perovic D, Sharpe AG, Fobert PR, Koch M, Wise IL, Fenwick P, Berry S, Simmonds J, Hourcade D, Senellart P, Duchalais L, Robert O, Forster J, Thomas JB, Friedt W, Ordon F, Uauy C, McCartney CA (2016) A saturated SNP linkage map for the orange blossom midge resistance gene Sm1. Theoretical and Applied Genetics 129: 1507-1517.

Kay R, Chan, A, Daly M, McPherson J (1987) Duplication of CaMV 35S promoter sequences creates a strong enhancer for plant genes. Science 236:1299-1302.

Lamb RJ, Mckenzie RIH, Wise IL, Barker PS, Smith MAH (2000) Resistance to Sitodiplosis mosellana (Diptera: Cecidomyiidae) in spring wheat (Gramineae). The Canadian Entomologist 132: 591-605.

Lamb RJ, Wise IL, Smith MAH, McKenzie RIH, Thomas J, Olfert OO (2002) Oviposition deterrence against Sitodiplosis mosellana (Diptera: Cecidomyiidae) in spring wheat (Gramineae). The Canadian Entomologist 134: 85-96.

Lamb RJ, Sridhar P, Smith MAH, Wise IL (2003) Oviposition preference and offspring performance of a wheat midge Sitodiplosis mosellana (Géhin) (Diptera: Cecidomyiidae) on defended and less defended wheat plants. Environmental Entomology 32: 414-420.

Lamb RJ, Smith MAH, Wise IL, Mckenzie RIH (2015) Resistance to wheat midge (Diptera: Cecidomyiidae) in winter wheat and the origins of resistance in spring wheat (Poaceae). The Canadian Entomologist 1: 1-10.

McElroy D, Zhang W, Cao J, Wu R (1990) Isolation of an efficient actin promoter for use in rice transformation. The Plant Cell 2: 163-171.

Meyers BC, Dickerman AW, Michelmore RW, Sivaramakrishnan S, Sobral BW, Young ND (1999) Plant disease resistance genes encode members of an ancient and diverse protein family within the nucleotide-binding superfamily. The Plant Journal 20: 317-332.

Oakley JN (1994) Orange wheat blossom midge: a literature review and survey of the 1993 outbreak. Research Review No. 28, HGCA, Hamlyn House, Highgate Hill, London, UK.

Oakley JN, Talbot G, Dyer C, Self MM, Freer JBS, Angus WJ, Barrett JM, Feuerhelm G, Snape J, Sayers L, Bruce TJA, Smart LE, Wadhams LJ (2005) Integrated control of wheat blossom midge: variety choice, use of pheromone traps and treatment thresholds. HGCA Project, Report 363.

Robert LS, Thompson RD, Flavell RB (1989) Tissue-specific expression of a wheat high molecular weight glutenin gene in transgenic tobacco. The Plant Cell 1: 569-578.

Rossi M, Goggin FL, Milligan SB, Klaoshian I, Ullman DE, Williamson VM (1998) The nematode resistance gene Mi of tomato confers resistance against the potato aphid. Proceedings of the National Academy of Sciences USA 95: 9750-9754.

Sarris PF, Cevik V, Dagdas G, Jones JDG, Krasileva KV (2016) Comparative analysis of plant immune receptor architectures uncovers host proteins likely targeted by pathogens. BMC Biology 14:8.

Schweiger W, Steiner B, Vautrin S, Nussbaumer T, Slegwart G, Zamini M, Jungreithmeier F, Gratl V, Lemmens M, Mayer KFX, Berges H, Adam G, Buerstmayr H (2016) Suppressed recombination and unique candidate genes in the divergent haplotype encoding Fhb1, a major Fusarium head blight resistance locus in wheat. Theoretical and Applied Genetics 129: 1607-1623.

Sekhwal KM, Pingchuan L, Lam I, Wang X, Cloutier S, You FM (2015) Disease resistance gene analogs (RGAs) in Plants. The International Journal of Molecular Sciences 16: 19248-19290.

Stemmer PC (1994) DNA shuffling by random fragmentation and reassembly: In vitro recombination for molecular evolution. Proceedings of the National Academy of Sciences USA 91: 10747-10751.

Thomas J, Fineberg N, Penner G, McCartney C, Aung T, Wise I, McCallum B (2005) Chromosome location and markers of Sm1: a gene of wheat that conditions antibiotic resistance to orange wheat blossom midge. Molecular Breeding 15: 183-192.

War AR, Paulraj MG, Ahmad T, Buhroo AA, Hussain B, Ignacimuthu S, Sharma H C (2012) Mechanisms of plant defense against insect herbviores. Plant Signalling & Behaviour 7: 1306-1320.

International Search Report, PCT/EP2017/075849, dated Dec. 11, 2017.

Extended European Search Report, 16306334.0, dated Feb. 17, 2017.

Akhunov, et al., WHE2063_C10_E19ZS Wheat salt-stressed sheath cDNA library Triticum aestivum cDNA clone WHE2063_C10_E19, mRNA sequence, BG313458, Feb. 26, 2001.

Pozniak, et al., "CDC Carbide durum wheat," Can. J. Plant Sci. (2015) 95: 1007-1012 doi:10.4141/CJPS-2015-045.

* cited by examiner

SEQUENCE LISTING

```
<160> NUMBER OF SEQ ID NOS: 37

<210> SEQ ID NO 1
<211> LENGTH: 8139
<212> TYPE: DNA
<213> ORGANISM: Triticum aestivum

<400> SEQUENCE: 1
atgccggcag cagcggcggc gggtcaagtt ttccagtttc cagtttctta gcagcggcac      60
catacggatc ccacctgaca atatggcccc acgatcaaat accacattga cttcatccac     120
gtcagcaaac cacctttttt tattttgacg ggaaggtata ctttattagg tcaaataacg     180
gttacgtcag caaaccacct aagtgaaccc atctaggacc atttctaacc ggacgagata     240
gataaggagg ttaagagagc agaaaaaatg atcaggggt tatgtgaacc atccattttg      300
ttcaggcttc gggggtggta ttggtaaaat ggactttttt ttttcaggaa aaaaaaagac     360
caacgatctc cttttttccta cacaaatctc ccttctgcct cgtccaatgc tcagctttcc    420
cttcttgctc cgtcaaccga actctccccc tctccaacat ttgtacccc accagatctt      480 gccccaaatc tcttcttctc cacaactcat gcccggaacc tctcttccct gctccaaggc    540
ccaaagcttg cagcaaggct tcgcggttgg aaatctgtga tggcttcccc aaccccaact    600
ccaatctaga tcttgctggt cttccccgag ctcgtgttac cccgccggtg acggtcgtcc   660
gtgcggtact gagctccatc ctctagcagt gcatctcgga gtggcggtca caccaaaagc    720
ataagttaat ttgaggagcg agcgggtcac cgaggtatgg aggtggtggt gggagtggcg    780
agcgctgcgg cgagcagcct ggttccgaag ctgctcacag tcttacagaa caagtggcga    840
gggtcggagg acattgaaga ggacgtctgc tccttgcatc gagaggttga catgatttat    900
gcttctagca aggatcagat ctcgcacaag gggcagccca gtgaccaaga gatcttgtct    960
ttgaaagaat tctgtgattt ggctcataac atcgaggact gcctagacca gttcattcct  1020
tgcgctgaat gcggcaaggg aaaactgaag atcctggatc caagcaagtt ccgtgatgag  1080
atcaagagac tcaagcggga gctggatgcg gcacaacagc ggagggacag acacgtcgtt  1140
gccgaatcca acgtcaacaa cagcagcagc accgctgtcg tggaggatac gggcaaaaaa  1200
tatgaggctt gtcctgcagt gggcatcgag caagcaaagg gggagcttag ggcgttgtta  1260
gttggcggcg aagcaagcaa gctgagggtg gtctccatcc tcggatttgg gggctccgga  1320
aaaacagcac tcgcctggga agtgtacaaa tgccctcaag tcgccaagga attcagttgt  1380
cgtgcctggg cgaccatggc gtccgagcag aaacacgaca tctctggcaa ggaggcactc  1440
ttgaaggcta tacaaaaggg gcttcttgga gaaaaaacac cggagcccgt gcaacagaca  1500
cccctggagc tcgaaaacaa tatcagtcat cttctccgga ttaataggtg aggattaatc  1560
```

```
ctaaactgtc actcggaata ttcacaactt gataccgtga agaaatataa gagcgtttag   1620
atcaccaaag tagtagtgat ctaaacactc ttatatttct ttacagatat cttatcacca   1680
gtttagatct gcttaattgt aggattcagt ttgtatctaa gattcaaagg aatttgatag   1740
gattttggga tgatttagat cattaggaat ttctctatgc ttgttgtttg attcatagtt   1800
ttggaatcct taggattcat ttgtactcta tttttggtgg tacatttcca tccgttgaaa   1860
cctcttgta gatttcattt gttttttctg tgttgtaaaa cacttttggt ccaaatttct   1920
tcagttttat aatcctatat gagattcaag aggacatggc actccaatct tgtcattttc   1980
ttattcccgc atttgggaa tcctaagatt aacatgtgac cgaggtcttg caagtgtcca   2040
agtacaagta tagttgtatc atcaggtttt cactgacagt attaatatct cagttcaata   2100
tgaaacccaa cgatcatagt gggtggcatt gcccttaggc tatttctggt gtcgttggtc   2160
actagttaat tccagggga aaatctgcac atggatttac taaaaaataa agaactttc   2220
gtattttag agttattcat tagttatgca accagtaatt gtaaaggctg aaaaaatgg   2280
taacgataag caagaatttt cgtccaaata ctggacagat tagctgatca agtcattggt   2340
tcgtatttcc agtagaatgc ttgcatacca aatatattct gaagatactt tatcctctaa   2400
tatagagttc agtagtctga aacatttacc gatttggctg acaggtgttt aattgtaatt   2460
gataacatca agatggagct ctggcacgca ataaaaccta tcttcccaga tgaaacggag   2520
agcagaatcc tagtgaccac aactgtgacc tcagtagcta atgcctgcag cttgcataac   2580
ggttatgcgt acagtataag atctcttagt gcaaacagt ccaaggatta tctagacaag   2640
aagcttttcg tcgatggatg ctcattggat gtggagtggg gtaccgcaat cgtgaacaaa   2700
tgtgatggtc acccacttgc tcttgttagt gttgccgaag cttttgcaagg ttgcggtgtg   2760
gtgacaggag atcactgtga agcaataagc gagaacctgg gtttccgtat ggaggagaac   2820
tggaatggtc acttcacaaa actgcaacaa gttctaatga atgattacag cagtctgcct   2880
gacaattctt caagaacctg cttactatac acaagtatat cccaaatag tcgccccttc   2940
aacacgaaca gtcttacgag gcgattgtca gccgaagggt acatacaggg tgatgataaa   3000
cgcagtgccc agcaggttgc atatgaccac ttggataaat tgattgaccg gaatatcatc   3060
cggcctatcg acgcacacaa caattcaaaa gtgaagacgt gcagaacaca tggaatcatg   3120
aatcagttaa tgttgtataa gtccaggtct tcgaatttca tttctacatc tattaatgat   3180
aataaccgaa gtaattaccg tcacctggtt atccagaata acagaaacgg taaaagcttc   3240
agtccagaaa caagtgtcaa gggcaagcag ctgcgtcccc ggtctctaac agtctttggg   3300
agtgcagaag aagccgttcc agatttgaag agttgtgagc tgctgagagt gttggatctg   3360
aaagaatgca atgatttgag ggaccaacat ctcgagcaca tatacaagct gttgcatcta   3420
aaatatctgg ccctcgggga ttctagtagc aaatatctgg atagaatggg aaagctacat   3480
tgtttagaga cactcgactt gaggaagagg aaaatcgaga tactgccagt ggaagtcatc   3540
agtttgcccc acctagcaca tctgttggga aagttcaagc taaacaagtt gggtaagagg   3600
aagcttaaag agttccggtc aaacaaatgc aacttggaga ctgtagcagg agttattgtt   3660
gacagcgact ctggattcct ggaattgatg gttcatttga agcaacttag aaaggtcaag   3720
atatggtgcg agctcactag cacagattgc aagaacatac tgggttcact ttcaaaggcc   3780
attcaaaagt ttgctaagga tggcatagat actccagtag gtgaccgtgg tcgcctatca   3840
ctccatttca acaattattc tgaaggtctg ttgcactgtg aagatgaccc cacatttctt   3900
ggttatctta actcgctgaa actgcaaggc agcctgagtc agttccctaa gtttgctaag   3960
```

```
tccctcgatg gtctgcaaga actgtgcctt acatatacta atctgacggg ggctgatctt    4020
ctactaggtc tgtgtaggct acgacgcttg gtttatctca aactgatcga agtccatctt    4080
gcggatttag acttagaaga tgggatctc ccaaaactgc aacgtctatg cctcgtggtg     4140
caacagccca gattccccag tatccgaaca ggcgctctgc cgaaactaac ttcaattcag    4200
ttgctctgtg gtggtctgga agatcttggt ggcatcgaaa tggaattgtt caaggacctc    4260
cgggaaatcg ctcttgattc tacggtcaac ccaaaaacca taaagctctg gaagatgaa     4320 gctaagaagc accccaagag gccaacggtt atcttgctcg ataaggttgt tgctccagcc    4380
gaagctacgg cttcggtgaa atatgtcgcc tcctgcaaag cctacaacaa ttgctacgcc    4440
gacgctctgg agcggaagtt gcagaggtca tgtcaagtaa caccttcgcg cgagcaatcc    4500
ccgccacctc gctctcagcc tgatcatcaa gctcaagttc gcaatggatt aggtttgcat    4560
atttctcatg ccaatcattg ctctgctaac atagcaaaat aatgttgcat gtttagttgt    4620
caataacgtt ctacacgttc tggataacta gaaatagtct catttctatt ttgtgtattc    4680
cagctttgcc atcttgtttt ggagcaccag aagccggtga agccgacggc gcacgtgatg    4740
ctggactcga tccattgcat ttgcattcgt cgtccgttga gcaggcgaac aagacagtgc    4800
catcgatcat gcccaacggg agcaaggagg tgtgagtgac acgggggcct ggaaatctct    4860
tttctaggtc gtccagtcta tttagttttct gaataaattc cggccatgta ccagcattgg   4920
cagatgcttc tgtctggatg ctgcatggca accgggaaaa gacttactat tttctattca    4980
tgtatcggtc acctttaaa tttcgtattt atgggtctg cacccccgaat ctgtgttgga     5040 ggataaatgt attatgtcag tcttatcaac gatttctcat aaattcactt ggatctgttt    5100
atttcgtgcg atttttttgt ggtaggaatg cttttgttga atttttcttt gaaaaaagc    5160 atgccgcaaa attcagaata ggggaagggg gtctttctgg gcaagtccaa gattatacgc    5220
aagaacagag catttttccct ttttgcggga agcgggaaca gagcatgtgc tctgctttga   5280
gcagagccgg ggccattctc ctcctcttgg gctcgactaa aaggttgtgg cccagcccgg    5340
cccgctcctc ttgggttgga ccaaaagggg cccgcccgac tcatcgggga gtatgcagcg    5400
gcggcggcgc aggtgcttct ccaagccgac ccagtatttt gagggtgaac ggaatggtga    5460
ttgcaagtcc acgcatccgc accgcgcgct agaatttgtt agctggttac cccctcttcc    5520
accgaattgt agtgtaggca gcaatatata tatttgcttc ccccgtggtt agtattttt    5580 tttgaggata actttcaatt tattcatcgg ctgtcaaagt agtacaaaga acaccagaag    5640
taaaatatac atctagctaa cagaaaagat tagttttctg catcaaatta atcagtatag    5700
ttctcccccg tggtcaatag gctgtcaatt agcccatcca acttgcttct cgtggagcct    5760
catgaagagg aaaagcgtgt tttttttttc tttcgcgttc aggcaaggat gtgcttccac    5820
aagagatgct tctcgaatga gaaaaaaaat catgcttccg tccagggcct gccctgaggg    5880
ggtggcaggg gggcggccgc ccaggccccc cgaaatctag gcccccctc cagggttcgc     5940 aaggagccca tggcccaaac cataaggagg cgtcgaccta gacgcacgga gaaatccctg    6000
tttcccttct tcccccttgcg agttcgccgc ttcgcgacga tcgtattccc ccgagggccc    6060
cggtcgcgag tcgcaacgcc gatgtagatc gctctccgcc atgcggccgg ctggtcttcc    6120
tccaggtccc cggtcccgtc gtgttatccc ccgttcgtga gttttctctc atgtgcaaga    6180
cgaaaccacc ccacttataa agtcatccct aacctcctct ttctagttgg tcagatctta    6240
gaaggtctcg catatgatgc agcagcagtc agcagtacaa aattgtagat ggtgtttaca    6300
```

-continued

```
atagcccttt tgttcatatg gtgctaccgt acaaaattta caattgtatt gcatcatatc    6360
ccccgcttgt ctaattaagt aaaggaatac actatttaca tttttcattt tattttggaa    6420
caatagacaa taataagtta ggtaaaggaa tgaatctaaa aagaaacgag attattattt    6480
tgatctttat agtaggggcc ccgggttgta atttcgccct ggctcctgaa atatcaggac    6540
cggccctgct tccgtcttag gttttcttct tccggttttt ttgtggaaaa aatttccatc    6600
gaaacctatg aacaagggat ctagattcga aaatctctat gggaaatcga acggtgaaaa    6660
cgcttcgcga tttagatgca cggtttaaga gataaaccat tttaaaatga tttatgtaaa    6720
ttgtttttgt aatatattta tttataatat ttggaagtat agattgaagt taaaaagaa    6780 gtataaacga ggttgtggtc tcccatgcgt ctgggccggc ccatctcgcg cgctgcttga    6840
tgtgaggctt ccctcggtct cactacaagc aaggtatagc tgcgctcgag cagaacccgc    6900
atcgcaacct atcggcttac cctcgcggga gctcctatct gccgctaact acggcaaatg    6960
tccaaggaac gcacaggcgg gtctcccgac tgggccgggc catgtggctc tcccgttccg    7020
gctagccaag aaactacatc gctcgctcgc aaaaaagaat gccctagcag gattcgaaca    7080
caataccacg tcgtgcttca caagtattac tcctaccact tgagctagcg agctaggtgt    7140
tttcacggac agcgcaaata cttaagaacc aaaccaagcg cggatatgaa cgtatttcaa    7200
atttcaacac gaaatattat tttggagaaa aagtgaattc tgtatgaaac cgcgaacact    7260
tttcgaaatt gtgtatattt taaaaactca aacatttcaa aaaacacaaa caatttctgg    7320
aaactgaaac aatttttaaa ctcccccaa gaaattgcaa acatttttgt acaaaactag    7380
aacatttttt gaatggaaaa acaattttta gttacacaaa cattttttgaa aaatgggaaa    7440 aaattgaatc tcccgaaatt ttttttgagaa caccaacatt ttctgaaact cctgaacaga    7500
gttcaatgca caaactattt ttaaaaattg cgaacaaatt ttgaaaacat gaacattact    7560
taaaaaatca tgaacatttt ttatactcct gaacaaaaat tgtaaaccca aatgctattg    7620
taaatttgag acaattttcg taatactgaa caaaatttga gaagttgcga aatgctgaac    7680
aatttgtgat aaatcaaaca attttttaaat ttatgaacat ttttccaata acataaaaag    7740
gaaaaacaaa gaaaaagaa cacgaaaaaa gagagaaaat aataaacaaa caggaaaaaa    7800
agaaaaagaa aaaatgaaaa gaaaaaacag gttcaggaac ctactaagtc ccaaaaccgg    7860
gaacacccgg ctggaaccttt ccagcaaatt attattagct agtgttggtg gtgattagat    7920
agctaccgca gctagtgttt ttgtgatta gctagctaga atgagtttaa aaatgatgat    7980
gtgctacact atgattatga tgattaaata actactgttg gtggtaatga ctatgatgat    8040
gattacatag cttgtgctgg cggattagat tcaagtggag gcaacatgtg gtgcacatca    8100
aaaatactac tagtccaaac tagatcaagt ttggattag                          8139
```

<210> SEQ ID NO 2
<211> LENGTH: 4308
<212> TYPE: DNA
<213> ORGANISM: Triticum aestivum

<400> SEQUENCE: 2

```
atgccggcag cagcggcggc gggtcaagaa aaaaaaagac caacgatctc cttttcccta     60
cacaaatctc ccttctgcct cgtccaatgc tcagctttcc cttcttgctc cgtcaaccga    120
actctccccc tctccaacat ttgtacccca accagatctt gccccaaatc tcttcttctc    180
cacaactcat gcccggaacc tctcttccct gctccaaggc ccaaagcttg cagcaaggct    240
tcgcggttgg aaatctgtga tggcttcccc aaccccaact ccaatctaga tcttgctggt    300
```

```
cttccccgag ctcgtgttac cccgccggtg acggtcgtcc gtgcggtggt ggtgggagtg    360
gcgagcgctg cggcgagcag cctggttccg aagctgctca cagtcttaca gaacaagtgg    420
cgagggtcgg aggacattga agaggacgtc tgctccttgc atcgagaggt tgacatgatt    480
tatgcttcta gcaaggatca gatctcgcac aaggggcagc ccagtgacca agagatcttg    540
tctttgaaag aattctgtga tttggctcat aacatcgagg actgcctaga ccagttcatt    600
ccttgcgctg aatgcggcaa gggaaaactg aagatcctgg atccaagcaa gttccgtgat    660
gagatcaaga gactcaagcg ggagctggat gcggcacaac agcggaggga cagacacgtc    720
gttgccgaat ccaacgtcaa caacagcagc agcaccgctg tcgtggagga tacgggcaaa    780
aaatatgagg cttgtcctgc agtgggcatc gagcaagcaa aggggagct tagggcgttg     840 ttagttggcg gcgaagcaag caagctgagg gtggtctcca tcctcggatt tggggggctcc   900 ggaaaaacag cactcgccct ggaagtgtac aaatgccctc aagtcgccaa ggaattcagt    960
tgtcgtgcct gggcgaccat ggcgtccgag cagaaacacg acatctctgg caaggaggca   1020
ctcttgaagg ctatacaaaa ggggcttctt ggagaaaaaa caccggagcc cgtgcaacag   1080
acacccctgg agctcgaaaa caatatcagt catcttctcc ggattaatag gtgtttaatt   1140
gtaattgata acatcaagat ggagctctgg cacgcaataa aacctatctt cccagatgaa   1200
acggagagca gaatcctagt gaccacaact gtgacctcag tagctaatgc ctgcagcttg   1260
cataacggtt atgcgtacag tataagatct cttagtgcaa aacagtccaa ggattatcta   1320
gacaagaagc ttttcgtcga tggatgctca ttggatgtgg agtggggtac cgcaatcgtg   1380
aacaaatgtg atggtcaccc acttgctctt gttagtgttg ccgaagcttt gcaaggttgc   1440
ggtgtggtga caggagatca ctgtgaagca ataagcgaga acctgggttt ccgtatggag   1500
gagaactgga atggtcactt cacaaaactg caacaagttc taatgaatga ttacagcagt   1560
ctgcctgaca attcttcaag aacctgctta ctatacacaa gtatattccc aaatagtcgc   1620
cccttcaaca cgaacagtct tacgaggcga ttgtcagccg aagggtacat acagggtgat   1680
gataaacgca gtgcccagca ggttgcatat gaccacttgg ataaattgat tgaccggaat   1740
atcatccggc ctatcgacgc acacaacaat tcaaaagtga agacgtgcag aacacatgga   1800
atcatgaatc agttaatgtt gtataagtcc aggtcttcga atttcatttc tacatctatt   1860
aatgataata accgaagtaa ttaccgtcac ctggttatcc agaataacag aaacggtaaa   1920
agcttcagtc cagaaacaag tgtcaagggc aagcagctgc gtccccggtc tctaacagtc   1980
tttgggagtg cagaagaagc cgttccagat ttgaagagtt gtgagctgct gagagtgttg   2040
gatctgaaag aatgcaatga tttgagggac caacatctcg agcacatata caagctgttg   2100
catctaaaat atctggccct cggggattct agtagcaaat atctggatag aatgggaaag   2160
ctacattgtt tagagacact cgacttgagg aagaggaaaa tcgagatact gccagtggaa   2220
gtcatcagtt tgccccacct agcacatctg ttgggaaagt tcaagctaaa caagtttggt   2280
aagaggaagc ttaaagagtt ccggtcaaac aaatgcaact tggagactgt agcaggagtt   2340
attgttgaca gcgactctgg attcctggaa ttgatggttc atttgaagca acttagaaag   2400
gtcaagatat ggtgcgagct cactagcaca gattgcaaga acatactggg ttcactttca   2460
aaggccattc aaaagtttgc taaggatggc atagatactc cagtaggtga ccgtggtcgc   2520
ctatcactcc atttcaacaa ttattctgaa ggtctgttgc actgtgaaga tgaccccaca   2580
tttcttggtt atcttaactc gctgaaactg caaggcagcc tgagtcagtt ccctaagttt   2640
```

-continued

```
gctaagtccc tcgatggtct gcaagaactg tgccttacat atactaatct gacgggggct    2700
gatcttctac taggtctgtg taggctacga cgcttggttt atctcaaact gatcgaagtc    2760
catcttgcgg atttagactt agaagatggg gatctcccaa aactgcaacg tctatgcctc    2820
gtggtgcaac agcccagatt ccccagtatc gaacaggcg ctctgccgaa actaacttca     2880
attcagttgc tctgtggtgg tctggaagat cttggtggca tcgaaatgga attgttcaag    2940
gacctccggg aaatcgctct tgattctacg gtcaacccaa aaaccataaa gctctgggaa    3000
gatgaagcta agaagcaccc caagaggcca acggttatct tgctcgataa ggttgttgct    3060
ccagccgaag ctacggcttc ggtgaaatat gtcgcctcct gcaaagccta caacaattgc    3120
tacgccgacg ctctggagcg gaagttgcag aggtcatgtc aagtaacacc ttcgcgcgag    3180
caatccccgc cacctcgctc tcagcctgat catcaagctc aagttcgcaa tggattagct    3240
ttgccatctt gttttggagc accagaagcc ggtgaagccg acggcgcacg tgatgctgga    3300
ctcgatccat tgcatttgca ttcgtcgtcc gttgagcagg cgaacaagac agtgccatcg    3360
atcatgccca acgggagcaa ggaggtgaat gcttttgttg aattttcttt tgaaaaaaag    3420
catgccgcaa aattcagaat aggggaaggg ggtctttctg ggcaagtcca agattatacg    3480
caagaacaga gcattttccc tttttgcggg aagcgggaac agagcatgtg ctctgctttg    3540
agcagagccg gggccattct cctcctcttg ggctcgacta aaaggttgtg gcccagcccg    3600
gcccgctcct cttgggttgg accaaaaggg gcccgcccga ctcatcgggg agtatgcagc    3660
ggcggcggcg caggggtgg caggggggcg gccgcccagg gccccgaaa tctagggccc      3720 ccctccaggg ttcgcaagga gcccatggcc caaaccataa ggaggcgtcg acctagacgc    3780
acggagaaat ccctgttttc cttcttcccc ttgcgagttc gccgcttcgc gacgatcgta    3840 ttccccccgag ggccccggtc gcgagtcgca acgccgatat tgaagttaaa aaagaagtat   3900
aaacgaggtt gtggtctccc atgcgtctgg gccggcccat ctcgcgcgct gcttgatgtg    3960
aggcttccct cggtctcact acaagcaagg tatagctgcg ctcgagcaga acccgcatcg    4020
caacctatcg gcttacccctc gcgggagctc ctatctgccg ctaactacgg caaatgtcca   4080
aggaacgcac aggcgggtct cccgactggg ccgggccatg tggctctccc gttccggcta    4140
gccaagaaac tacatcgctc gctcgcaaaa aagaatgccc tagcaggatt cgaacacaat    4200
accacgtcgt gcttcacaac ttgtgctggc ggattagatt caagtggagg caacatgtgg    4260
tgcacatcaa aaatactact agtccaaact agatcaagtt tggattag                4308
```

<210> SEQ ID NO 3
<211> LENGTH: 1435
<212> TYPE: PRT
<213> ORGANISM: Triticum aestivum

<400> SEQUENCE: 3

```
Met Pro Ala Ala Ala Ala Gly Gln Glu Lys Lys Arg Pro Thr Ile
1               5                   10                  15

Ser Phe Phe Leu His Lys Ser Pro Phe Cys Leu Val Gln Cys Ser Ala
                20                  25                  30

Phe Pro Ser Cys Ser Val Asn Arg Thr Leu Pro Leu Ser Asn Ile Cys
            35                  40                  45

Thr Pro Thr Arg Ser Cys Pro Lys Ser Leu Leu Leu His Asn Ser Cys
        50                  55                  60

Pro Glu Pro Leu Phe Pro Ala Pro Arg Pro Lys Ala Cys Ser Lys Ala
65                  70                  75                  80
```

```
Ser Arg Leu Glu Ile Cys Asp Gly Phe Pro Asn Pro Asn Ser Asn Leu
                85                  90                  95

Asp Leu Ala Gly Leu Pro Arg Ala Arg Val Thr Pro Pro Val Thr Val
            100                 105                 110

Val Arg Ala Val Val Gly Val Ala Ser Ala Ala Ser Ser Leu
        115                 120                 125

Val Pro Lys Leu Leu Thr Val Leu Gln Asn Lys Trp Arg Gly Ser Glu
        130                 135                 140

Asp Ile Glu Glu Asp Val Cys Ser Leu His Arg Glu Val Asp Met Ile
145                 150                 155                 160

Tyr Ala Ser Ser Lys Asp Gln Ile Ser His Lys Gly Gln Pro Ser Asp
                165                 170                 175

Gln Glu Ile Leu Ser Leu Lys Glu Phe Cys Asp Leu Ala His Asn Ile
            180                 185                 190

Glu Asp Cys Leu Asp Gln Phe Ile Pro Cys Ala Glu Cys Gly Lys Gly
        195                 200                 205

Lys Leu Lys Ile Leu Asp Pro Ser Lys Phe Arg Asp Glu Ile Lys Arg
    210                 215                 220

Leu Lys Arg Glu Leu Asp Ala Ala Gln Gln Arg Arg Asp Arg His Val
225                 230                 235                 240

Val Ala Glu Ser Asn Val Asn Asn Ser Ser Thr Ala Val Val Glu
                245                 250                 255

Asp Thr Gly Lys Lys Tyr Glu Ala Cys Pro Ala Val Gly Ile Glu Gln
            260                 265                 270

Ala Lys Gly Glu Leu Arg Ala Leu Val Gly Gly Glu Ala Ser Lys
        275                 280                 285

Leu Arg Val Val Ser Ile Leu Gly Phe Gly Gly Ser Gly Lys Thr Ala
    290                 295                 300

Leu Ala Trp Glu Val Tyr Lys Cys Pro Gln Val Ala Lys Glu Phe Ser
305                 310                 315                 320

Cys Arg Ala Trp Ala Thr Met Ala Ser Glu Gln Lys His Asp Ile Ser
                325                 330                 335

Gly Lys Glu Ala Leu Leu Lys Ala Ile Gln Lys Gly Leu Leu Gly Glu
            340                 345                 350

Lys Thr Pro Glu Pro Val Gln Gln Thr Pro Leu Glu Leu Glu Asn Asn
        355                 360                 365

Ile Ser His Leu Leu Arg Ile Asn Arg Cys Leu Ile Val Ile Asp Asn
    370                 375                 380

Ile Lys Met Glu Leu Trp His Ala Ile Lys Pro Ile Phe Pro Asp Glu
385                 390                 395                 400

Thr Glu Ser Arg Ile Leu Val Thr Thr Val Thr Ser Val Ala Asn
                405                 410                 415

Ala Cys Ser Leu His Asn Gly Tyr Ala Tyr Ser Ile Arg Ser Leu Ser
            420                 425                 430

Ala Lys Gln Ser Lys Asp Tyr Leu Asp Lys Lys Leu Phe Val Asp Gly
        435                 440                 445

Cys Ser Leu Asp Val Glu Trp Gly Thr Ala Ile Val Asn Lys Cys Asp
    450                 455                 460

Gly His Pro Leu Ala Leu Val Ser Val Ala Glu Ala Leu Gln Gly Cys
465                 470                 475                 480

Gly Val Val Thr Gly Asp His Cys Glu Ala Ile Ser Glu Asn Leu Gly
                485                 490                 495

Phe Arg Met Glu Glu Asn Trp Asn Gly His Phe Thr Lys Leu Gln Gln
```

```
            500             505             510
Val Leu Met Asn Asp Tyr Ser Ser Leu Pro Asp Asn Ser Ser Arg Thr
            515             520             525
Cys Leu Leu Tyr Thr Ser Ile Phe Pro Asn Ser Arg Pro Phe Asn Thr
            530             535             540
Asn Ser Leu Thr Arg Arg Leu Ser Ala Glu Gly Tyr Ile Gln Gly Asp
545             550             555             560
Asp Lys Arg Ser Ala Gln Gln Val Ala Tyr Asp His Leu Asp Lys Leu
            565             570             575
Ile Asp Arg Asn Ile Ile Arg Pro Ile Asp Ala His Asn Asn Ser Lys
            580             585             590
Val Lys Thr Cys Arg Thr His Gly Ile Met Asn Gln Leu Met Leu Tyr
            595             600             605
Lys Ser Arg Ser Ser Asn Phe Ile Ser Thr Ser Ile Asn Asp Asn Asn
            610             615             620
Arg Ser Asn Tyr Arg His Leu Val Ile Gln Asn Asn Arg Asn Gly Lys
625             630             635             640
Ser Phe Ser Pro Glu Thr Ser Val Lys Gly Lys Gln Leu Arg Pro Arg
            645             650             655
Ser Leu Thr Val Phe Gly Ser Ala Glu Ala Val Pro Asp Leu Lys
            660             665             670
Ser Cys Glu Leu Leu Arg Val Leu Asp Leu Lys Glu Cys Asn Asp Leu
            675             680             685
Arg Asp Gln His Leu Glu His Ile Tyr Lys Leu Leu His Leu Lys Tyr
            690             695             700
Leu Ala Leu Gly Asp Ser Ser Lys Tyr Leu Asp Arg Met Gly Lys
705             710             715             720
Leu His Cys Leu Glu Thr Leu Asp Leu Arg Lys Arg Lys Ile Glu Ile
            725             730             735
Leu Pro Val Glu Val Ile Ser Leu Pro His Leu Ala His Leu Leu Gly
            740             745             750
Lys Phe Lys Leu Asn Lys Leu Gly Lys Arg Lys Leu Lys Glu Phe Arg
            755             760             765
Ser Asn Lys Cys Asn Leu Glu Thr Val Ala Gly Val Ile Val Asp Ser
770             775             780
Asp Ser Gly Phe Leu Glu Leu Met Val His Leu Lys Gln Leu Arg Lys
785             790             795             800
Val Lys Ile Trp Cys Glu Leu Thr Ser Thr Asp Cys Lys Asn Ile Leu
            805             810             815
Gly Ser Leu Ser Lys Ala Ile Gln Lys Phe Ala Lys Asp Gly Ile Asp
            820             825             830
Thr Pro Val Gly Asp Arg Gly Arg Leu Ser Leu His Phe Asn Asn Tyr
            835             840             845
Ser Glu Gly Leu Leu His Cys Glu Asp Asp Pro Thr Phe Leu Gly Tyr
            850             855             860
Leu Asn Ser Leu Lys Leu Gln Gly Ser Leu Ser Gln Phe Pro Lys Phe
865             870             875             880
Ala Lys Ser Leu Asp Gly Leu Gln Glu Leu Cys Leu Thr Tyr Thr Asn
            885             890             895
Leu Thr Gly Ala Asp Leu Leu Leu Gly Leu Cys Arg Leu Arg Arg Leu
            900             905             910
Val Tyr Leu Lys Leu Ile Glu Val His Leu Ala Asp Leu Asp Leu Glu
            915             920             925
```

```
Asp Gly Asp Leu Pro Lys Leu Gln Arg Leu Cys Leu Val Val Gln Gln
            930                 935                 940

Pro Arg Phe Pro Ser Ile Arg Thr Gly Ala Leu Pro Lys Leu Thr Ser
945                 950                 955                 960

Ile Gln Leu Leu Cys Gly Gly Leu Glu Asp Leu Gly Gly Ile Glu Met
                965                 970                 975

Glu Leu Phe Lys Asp Leu Arg Glu Ile Ala Leu Asp Ser Thr Val Asn
            980                 985                 990

Pro Lys Thr Ile Lys Leu Trp Glu Asp Glu Ala Lys Lys His Pro Lys
            995                 1000                1005

Arg Pro Thr Val Ile Leu Leu Asp Lys Val Val Ala Pro Ala Glu
    1010                1015                1020

Ala Thr Ala Ser Val Lys Tyr Val Ala Ser Cys Lys Ala Tyr Asn
    1025                1030                1035

Asn Cys Tyr Ala Asp Ala Leu Glu Arg Lys Leu Gln Arg Ser Cys
    1040                1045                1050

Gln Val Thr Pro Ser Arg Glu Gln Ser Pro Pro Arg Ser Gln
    1055                1060                1065

Pro Asp His Gln Ala Gln Val Arg Asn Gly Leu Ala Leu Pro Ser
    1070                1075                1080

Cys Phe Gly Ala Pro Glu Gly Glu Ala Asp Gly Ala Arg Asp
    1085                1090                1095

Ala Gly Leu Asp Pro Leu His Leu His Ser Ser Val Glu Gln
    1100                1105                1110

Ala Asn Lys Thr Val Pro Ser Ile Met Pro Asn Gly Ser Lys Glu
    1115                1120                1125

Val Asn Ala Phe Val Glu Phe Ser Phe Glu Lys Lys His Ala Ala
    1130                1135                1140

Lys Phe Arg Ile Gly Glu Gly Gly Leu Ser Gly Gln Val Gln Asp
    1145                1150                1155

Tyr Thr Gln Glu Gln Ser Ile Phe Pro Phe Cys Gly Lys Arg Glu
    1160                1165                1170

Gln Ser Met Cys Ser Ala Leu Ser Arg Ala Gly Ala Ile Leu Leu
    1175                1180                1185

Leu Leu Gly Ser Thr Lys Arg Leu Trp Pro Ser Pro Ala Arg Ser
    1190                1195                1200

Ser Trp Val Gly Pro Lys Gly Ala Arg Pro Thr His Arg Gly Val
    1205                1210                1215

Cys Ser Gly Gly Gly Ala Gly Gly Gly Arg Gly Ala Ala Ala Gln
    1220                1225                1230

Gly Pro Arg Asn Leu Gly Pro Pro Ser Arg Val Arg Lys Glu Pro
    1235                1240                1245

Met Ala Gln Thr Ile Arg Arg Arg Pro Arg Arg Thr Glu Lys
    1250                1255                1260

Ser Leu Phe Ser Phe Phe Pro Leu Arg Val Arg Arg Phe Ala Thr
    1265                1270                1275

Ile Val Phe Pro Arg Gly Pro Arg Ser Arg Val Ala Thr Pro Ile
    1280                1285                1290

Leu Lys Leu Lys Lys Lys Tyr Lys Arg Gly Cys Gly Leu Pro Cys
    1295                1300                1305

Val Trp Ala Gly Pro Ser Arg Ala Leu Leu Asp Val Arg Leu Pro
    1310                1315                1320
```

```
Ser Val Ser Leu Gln Ala Arg Tyr Ser Cys Ala Arg Ala Glu Pro
    1325                1330                1335

Ala Ser Gln Pro Ile Gly Leu Pro Ser Arg Glu Leu Leu Ser Ala
    1340                1345                1350

Ala Asn Tyr Gly Lys Cys Pro Arg Asn Ala Gln Ala Gly Leu Pro
    1355                1360                1365

Thr Gly Pro Gly His Val Ala Leu Pro Phe Arg Leu Ala Lys Lys
    1370                1375                1380

Leu His Arg Ser Leu Ala Lys Lys Asn Ala Leu Ala Gly Phe Glu
    1385                1390                1395

His Asn Thr Thr Ser Cys Phe Thr Thr Cys Ala Gly Gly Leu Asp
    1400                1405                1410

Ser Ser Gly Gly Asn Met Trp Cys Thr Ser Lys Ile Leu Leu Val
    1415                1420                1425

Gln Thr Arg Ser Ser Leu Asp
    1430                1435

<210> SEQ ID NO 4
<211> LENGTH: 10607
<212> TYPE: DNA
<213> ORGANISM: Triticum aestivum

<400> SEQUENCE: 4
atgcggatgg gcgggacacg cgcgcttgtc cgtccctggc ccgcatgtca gcgacacaaa      60
gtaaaacccc tctgcggccc ctttggcgcc atcctccccc cccaaaccct cccacatccc     120
gcccgtccca ctcccttccc cgtccatggc cgacgcccag ccgaactcct gcgggctggc     180
cgtcgacccc ccccccccg aatggccaag aagaagaagg acaaggcgcc aaggaagccg      240
cggtcggagt gcacgccgga ggagatcgcc aagttggacg cggaatcggt gaagaggagg     300
ggccggaggg cggtcgccaa accaacatc gccgcggcca agagagttgc cgagcgcgct      360
gcgattgagg ccgcacggca caaggccgag gtcgaggaga aggaggccat cgtcagcaaa     420
gcgcgcgccc ttctcatggc tggcatttgt cgtccgcccg gtttctctgg aagggccgtc     480
ggtccggcga gcacaaggtc gtcggtcgcc cggcctccgc actgccagtc gccgacatcg     540
cggaccacgc ccttgtcgcc cggctttcct ccaccaaggc acgacggcca gacccgtttc     600 gggggggtcgc cggatgtgag catgatcgcg ccgtccacac cacgcccctc ggccgtcatc    660
gacctcaacg tcacccttgg gtccagcagc ggcggccggc cgtcggtcga gatgcaaaga     720
aagcaagcac ggctgccgtt taccggcacc atgccgtccc ccgcgtcttg gttcgatgga    780
atgccaacac caacgatacc agtcgacgac ccctagtatg ccagttcat ggaggaagtg     840 atctacgagg gttggcacgt ccctgtctat gatcccgagg agacccaaag tcaggatggc    900
tgcggccagt tcactgccga tgaagaggcc aacgaccgtg ctgactacga tcatggtgac    960
tcgtggcatg aagacgatga catttatgtc gaaggtgatg gtgatgaaga agaaagaaat    1020
gacgttgaca ttagtgttga gccattgttc atcgacgagc tgacacaaag agcggaagca    1080 caaagaaga ggaagagcat tcgcacgagt tcatacacac aagatgagga caagttgatt    1140
tgccaagctt ggatggagat tagccaagat ccaggaccg gcgcgcaaca aaagggtatt    1200
gttttttgga cgagagtcca caaacattc catgaaagga agttgtttga gccctaccaa    1260
tttgaaagca accgtggcat cggctcgatt caaaagagat ggttgttcat ccaacaagag    1320
tgcaacaagt atcaagccgc atttgagagc gttcaagcac ggcccgtgag tggtctcggc    1380
gttggggaca tggtatgctc ttcttccttg ccctttcctt gctacggcca tgagacttcg    1440
```

```
gccttgtaca tgtttgcatg ttcacttgtt gttgatcata tgttgtaggc atttcaatct    1500
ttggaggcat tcaaggcccg gcacaatgac acgccgttca ctcttacgca ttgttggact    1560
atgatcaaca tttgccctaa gttcaaggac caataccgtg aactccaaag gaagagaggc    1620
ctgaagacgg ccaagtacgc cggaggtgga gatggcgagg cgttcaagag gccgaggggc    1680
aagaccaact ccaaggttga cgacatacgt gatgcctcat ccatggcatt gcatgacact    1740
ttgcatgaca tgatgtcgca aaaggatgtg aggaacgaga agaagcggca aagcaatggc    1800
aagcaaatga agcaatacct agagcttcaa acgaagaagc ttgagatgga ggaggcggct    1860
aagagaagga agatcggcat ggaggaggag gtccggcaga ggcagctcga catcgaggcc    1920
atcaatgccg ccaccaaagc gaaggaggtg gccctcgcga tcatgagcgt ggacttgtcg    1980
aagatgagtg agaagacgag ggcctggttc gaggccaggc agaaggagat gctcgacgcc    2040
gacggcctga actaggtcgt ccgatcggcc gtggccgttc ttttttggag gctggcatgg    2100
gtaccgcgcg cccgctgggc cgctggccat gtgccggcga gaaaaacatt tattttgaag    2160
gtcggctgtg ttgccggccg ctggctgtgt tgccgacgag gacgtccatt cattttggag    2220
gctggctgtg ttagcggccg ctggcgtgat ggacgtgtat gtcgctggct ttgttgccgg    2280
cgtgcgtgat gaactggggc cgtagggctt ggcatttgaa atgttgcttt ttttaaata    2340 gacgcggaca tggggctgga cgcacggcca ccgcatctca gaccaggccc ggacacgacc    2400
ccatctcctg accaaacgga cagaatccgg acaaatcgaa catccgggtc gcgcggtgga    2460
gttggcctta ggcccgcgta agaggcgttc aacgtactac taaacgtcca caaaaaaaaa    2520
cgtactacta acgtctacc agcggactcg acacctcgta tatgttgggc agtgcgagga    2580
gaacaaagaa gacgttgacg cgttgacgct gctcaagggc gcagctgagg gcgctgcaga    2640
gttcaagcgc gcggcgcggc gcagatctct accgtcgggc aggaggagaa gcccgaggaa    2700
ccaatgaagc ctgagcccga cccggggcgtc gccgtctggc agcccgacgg cgacgggtga    2760
ggatttttcg tgtttcctcc ctcctccgct ccgggatttg gccttcttgt tagttacttt    2820
ggtgctcgct cttgtgtttc tgttgcagag agatcgacat ggatctgctg cctccgatta    2880
gcgcgtctct gggcgccatg gcctcccttt ccgggaagct ggatgcgctc caggataccg    2940
aactcaagga tgagatccgg aaacttggat cccggctgct gaagctctcc gagccacatg    3000
aaccccgtca tgcggcgagg atctggatga atgaggcgcg cgaactatcc tatgacatgg    3060
taaactgtgt cgacgcggat gcagactgga tcgacaagat gtcaagaata ttcaagccac    3120
gcgtgaagga ggccaatggg cggtaccaca gatacaagct tgagagcgtc cccagccgtg    3180
cagctgtctt agcgatccca atggtggtcg gcgacgccgg ccggaagcca gatctactcg    3240
tcggccttca cgccaatggt ggcgccttcg aaacgctccg caaaaatctg attgaccggg    3300
acgagcagct caaggcgcta ttcgttgttg gtgttggagg aatcggcaag accacgcttg    3360
ccaaagagct atggcgtgag cacaaacccg ggcaccactt ctgctgccgg gctttcgtgc    3420
ggaccgccaa gaaacctgac atgaggagga tcctgaggag catactcgca caagttcgtc    3480
cggatcaacc accccgtcgct aatgaggtgc acgagctcat tcacgacctc accgagcatc    3540
taaaggataa aaggtacttg agctgttgag cacctttctt ctttaatata tatatatgat    3600
atgtacgctc ttgcatattc aagaaaaaaa tgtacttgag aaatgtatat agaactttca    3660
tcattctgat aagactactt gaatagcgag tggttttttct acaccacgc tagatgcagc    3720 catttcttaa ttcattataa ggtgttttaa tcttgaacaa tgaagtattt tctaaatccc    3780
```

```
tgcaaacaaa ttatttcta agtgtttata ttggtacacc attttcactc aaataaggtt    3840
ttggtgggtc ttactgtcac accaactgca aacagaataa cttgcctctg acaatagaaa    3900
tgcactcagc caaaagactt acaaagttca ttctgcaaca tagcagtcta agtgtggagg    3960
agaaaattac tagggtggag aagtgacaat ctatagtctg caccttgata aaaaagtat     4020
atttcccaca aaataagagt agaaagtaca atatgcaaaa acggcatttt cctcttgtga    4080
aaacagagtg gtcttcttgt gaaaacagag tctgtctact ttgtggtgtt gtcttcaatg    4140
ccctagtgac acaacagtgc attgattttt ctatgtgttt ttccttcttt gctgacttgt    4200
gtgtggatgg tctcgtgatc ttctgttctt gaccgtccca tcatcttgag cttgcgagga    4260
ttggtgactc actagggcct agggtgtgcc atggcgtgcc tcctgagagg gagatgtgcg    4320
tacttgtctt agcatcagtc caattagcac tttcatgtca aaccgagact tttctcgtgc    4380
tacgtgtggt cggcacggca gggtcggagc agcggaggcg tgcgcagcca tctctctcct    4440
aacgcgcggc cggagaataa ccacacacgg aggctggtcg tctcggccgg cgcgccgttg    4500
cggagaagga gtggacctcc gtctctcgcg gcccgggccg aagcctcgac gacggagcgg    4560
atgtgctgcg gtcgcggtcc gggagcgcca tcgccgctcg atctgggtag caagagaagg    4620
tgagggcgcg gcggcgtggg gagaagaagg cggagggaga cggcgtcgcc ggtgggagag    4680
aaggtgaggg gagcggcggc gttgcagac gaggtcgccg gtgggagaga aggtgagggg    4740
agcggcggcg gcgtgttga gtcgggagag gaggagagcg ggcgagggtt gggtttgtgt    4800
tcgttttttc ttttttttc cttttgtga gctgggctcg gtgaattatc tccctccctc    4860
cctctctcct tttttctct ttttcattt gaaatctagt agcgggagca attaaggcct    4920
caacattatt tcgaggcgac taaaataaat atttggcgg gagctttcag gttgattggt    4980
tgggcagcgc accgtctcaa aattcaagga cgcccttgat atatgatccg aaattcatgg    5040
ctattagaaa actaaaaaca aattagcagt taactgacct tttgattggc tattcgtgct    5100
acgtggcata agccagcggg cgcccagcgt ttcgttgata atgggtttga tggtttcaga    5160
gctgataccc atgatgacac tcctaattag ttgcactcag caatctgtga agcaacaata    5220
agccagttaa taggatgttg gacaatctct tttccttctt tattccatgg cacgtatcca    5280
ttaattttgc cttttatttg catgaaagtg ttatgggtat gcaagggtgg cactgacctg    5340
atgtgtaagg ttaggtactc gaacttatga gtgtagcact gaaataactg tgtgcttgtt    5400
ttaggagtat ttgtggtatt ccatttacat ttaattatac tatatacttt gtttatcagg    5460
tacttcatta taattgatga cttatgggat acatcagtat gggatgttgc agcccgtgct    5520
ttcccaaagg gtaaccaagg cagcaggata gtaacaacaa cggaaattga ggatgttgct    5580
cttgcatgtt gttatcagtc aaagtacgtg cttaagatgg aacatcttag cgagagtcac    5640
tcaagagagt tgttcaccag tgcagtgttt cgctctggag aacaacactc tcaccacgta    5700
ggtgaagtgc cagatgagat tataagaaga tgtgctggtt taccacaggc aattatcagc    5760
atatccagtg ttctagcaag ccatggagaa gcaaatacag taaagaactg ggagcaaata    5820
caaaacagtt tgccaacaaa tacaacttct gacgagatac tgaaagaagt actgattttt    5880
tgctataata gtcttcccag ttgtgttcag acatgtctgt tgcatcttag tatatacccg    5940
gagaactatg ttatcttgaa ggaagatata acgaagcaat gggttgctga aggtctcatc    6000
agtgcaccaa cagagaaaga aaaaatggaa attgccagga gctattttga tatgcttgtc    6060
agtatgggca tgatccaaca tatagacgta gactatggca atgatgtttt gtactatgcg    6120
gtgcatcaca tggtacatga tatcattaca tccaagtcca tagaagagaa ttttgttaaa    6180
```

```
gtaatagatt attctcaaag ggcggtacgg ttttctaaca aggttagtcg tctgtccctc    6240
cagtttggcg gtgcaacata tgcaactaca ccagcacgta tcgaactgtc gcaagtgcga    6300
tctcttgctt atactggact gaagagctgc ttgccttcca tctcagagtt taagcttctc    6360
cgggtactga ttctccatat ttgggctgat caaccaagca catgtgtcac tcgcaaaaaa    6420
aagaaccaag cacaggtgtc cacctcgagt gtatctctcg attgcttcta ttaatatatt    6480
tgcaggtgac atgcaacggc accgtgcatc ttccaaaaca gatgcgatgt ctgaaacact    6540
tggaaacact tgaaataaat gcaacagtag cagccattcc atcggatatt gttcatcttc    6600
ggagcttgtt gcatctccgt ctaggaggtg ggacagaact gcctgatgtg acaggtgtcc    6660
tcacaaatgt taccctgaat cttcctagtg ctgccacttt attggatgat tcgagcagtt    6720
ctcccgattc actgaacaca atggagctat tgccacccat ttgcagaatc cccaactgga    6780
ttggacagct tactgaccct tgcattctga aagttgtcgt cagagaactg ctaagggatg    6840
atatcagtaa cctggaaaga ttgccagcac tcactgttct ctccttgtac gtccagcaaa    6900
gaaatacaga actaatcatt ttcgaagccg gagcattttc tgctctcgag tgttttgagt    6960
tcaggtgtgg tgaactgcag ctgatgtttc aggaaggagc aatgcccaat cttcacagaa    7020
tcaagctagg tttcaatgct cacaaaggag aacagtatga tcgtcttctt agcggcattg    7080
agaacctgtc tgacgtccag gaaatttctg gaataattgg ggcagcccct ggtgccgatg    7140
agcatgactt tcaggctgca gaatctgcat tcatgaaagc tgttagcaag ctctctagta    7200
aagtcagtgt aaaaagagca gatatggttg aggaagaggg tggcctggca gaaaaacagg    7260
atgtgatccg agagaaagat gcatcaagac atgtaataag tgaacagcct gcaattctga    7320
aacaagagtc tgaggaagat ataaagcaaa atgctggtgg cagtttgcct agcggcatta    7380
agaacctgtc aaacgtccag gaaatttctg gaataactgg ggtagccaca ggtgctgagg    7440
aacatgaaat tcaggctgca gaatctgcat tgatgaaatc cgtcagtgag caacctagta    7500
aggtcactat aaaaggagca gatatggttg agcaagggta tggtccggca gacaaacaac    7560
atgtgagccg agagaaagat gtatcaagcc atttaagaag tgaacaacct gcaattgtga    7620
aacaagagtc cggtggcaac tctcagttca ttcaatggta cggttctttg tcctgttatg    7680
tccattattt cacactttct ctttctttgg tgaacttcca ttacactctt ctgcctcaca    7740
cagtaatagc taaacatagg tcatcaccaa ctttgaactt tattttgcac tgacgttgca    7800
ctcttttaaa tgggtgtgat ttgtgcaaag ctccattgct caagtaacag aggtcaagga    7860
gaagaacgaa taaattggtc atatatgttt aaagcttgct ctagatgtaa aaatatatcc    7920
ataaaatttc gcaaatgtgg aacatcctta ttttcttagc aggagaagca atagcaagga    7980
aacttcaaac gtggtgcaag gtttgtcagg gaaccgagaa cttcgtggcg gtgctgttgg    8040
agaagttaac aaggtatggt tttgttttgt aagggaacat ggtacgattt aagacataca    8100
tagtacttac atacttctga aaccatcgct caagtcccat gatttcaaat gtgcatgatt    8160
atctaacacc atatttgatc atgttttttg caagttttac ttcttggata tatgcacaga    8220
tgtgacaatc caaatgtact agtagtacat aactttgaaa atatcagcca aattcagtga    8280
tttcagggta ttagatcaca tacactgaaa tcagtgtatg ctgcatacct aaattcagga    8340
caggttatcc aaaactaacc caaaattctt tttaactttt tgtgattttt ttcatacgta    8400
tgtggtacat tttgattttt atgactaggt aaagaaacta atgttgacaa aaagccaggc    8460
ttgcttttaa tttccgtatt tgattttaa atcatggagc tagctatcat agattccaca    8520
```

| | |
|---|---|
| tttaccaggg agctagctgg agagccaaaa agtggattaa gaatgatcat tgtggatgtt | 8580 |
| gaacatattc tctcctctta ggtgaaatat ttttctctct ttctcaggaa gaagaacgtc | 8640 |
| agaatagcct ggcgagaggc aaaagcagca tggatattaa actcgtggag atcgaagcca | 8700 |
| tcacaaacaa ttttgcagag aacagaaagt cggcagcgg tgggtacgga gatgtttaca | 8760 |
| gggtatgttc ttttactact gatcattgta ttttctgtct gtatttctca catttacaat | 8820 |
| caagatctgt actatgacaa gtcgtcgatt ttatcaggcc actcacaaag gagaggaagt | 8880 |
| tgccgtgaag aagctccatc aactgcaggg actcgatgat aagcaattcg acagcgagtt | 8940 |
| ccgtaacctt cgtaatatac gccaccaaaa tgttgtgcgg ctaattggct actgccacga | 9000 |
| gtctcgcaag aaatacatgg agcacaaggg ggagctcatc ttcgccaaag agatggagcg | 9060 |
| cgtgctctgc ttcgaatata tgcacggcgg aagcctcgat aaacatatta caggtcatta | 9120 |
| actctcttct gtgacctgca tccaagatat atgaatgatt cagcatcata tatctgacaa | 9180 |
| atacgctgct gtgtttactt gtaattgcag atgaatcttg tgagcttgat tggccgacgt | 9240 |
| gttacaaaat catcaaaggg acttgtgagg gcttaaatca ccttcacacc tcgcagggga | 9300 |
| agcctatttt acatctagac ataaaaccag ccaacatatt gctggataag agcatgacgc | 9360 |
| ctaaaatcgc cgatcttggt ttgtccaaac ttgtttcttc gacattaaca cataaaacag | 9420 |
| agattgtcaa agggacacag taagttgatg catagtttag gcttgcttcg ttcttgtatg | 9480 |
| acttgaaact gagcctttgt ttctcttgca ataaccatat ctattatgct tttgatgata | 9540 |
| tcttgcagag ggtacatgcc gccagagtat gtagacaatg ccagatatc gaacaagttt | 9600 |
| gacgtgttta gttttggcgt agtaattata aaaatgatgg ccgtaacgt gggctacttc | 9660 |
| cgttgtgctg aaatgtctca caaagagttt attgagctgg taagaaaaat accccctgtt | 9720 |
| gattccatga atatataatt atacatacat ctcagcctct ctcttttttgg gggtgtctct | 9780 |
| tccaagtgtt agtatactct aggaagctttt atgcgccaac tttgcatgta ggtaactaaa | 9840 |
| aactgggtga aaaggttgct gacagagcct ggatattcct cgcacgaaac cgacatgcta | 9900 |
| ggagtcacta gatgtgttga aattgcatta agatgtgtgg acaaggaccg aaacaaaagg | 9960 |
| ccctgtatta aggatgttgt ccatgagctg gaggaactag aagctgagat caagaaaatg | 10020 |
| tccctatctt ccgaccagtc aaaaggccta agtctgcagg caagcatcct tgtcactctt | 10080 |
| tgtactaggt tttgcaactc tctgtttttt cacagtagca ttcagccctg acaaacttct | 10140 |
| gtcaaatttg tatcaacgta gcgatgtttg tacgaccgga tgcagtaact gacgccttat | 10200 |
| tttcttttca gagaagctgt gacaccaaca ttctctcggt ggatccgacc ctcgagctgc | 10260 |
| ggttcgtctt tgagccaagg aaggagacgt cgtgctgtct gcagatgacc aacaagacgg | 10320 |
| gtggcttcat cgcattcaac atattgatga acaagaacaa gtatagtgtg cggccaagcc | 10380 |
| aagggaccat gccaccgtgc tccaggcgtt atgttgtcgt gacactgtca gcgcaagagg | 10440 |
| cggcgccgcc atacatgcgg tgtgacgaca tgctcctagt gcagagcacc agcatcaccc | 10500 |
| aagatcttgg tgagatcaat tatcaagaat tgttcgacgt ggccagggcg gataaggtgg | 10560 |
| ttgatgtggt gcatctgcca atcgcatatg tcacgttaga agagtag | 10607 |

<210> SEQ ID NO 5
<211> LENGTH: 6912
<212> TYPE: DNA
<213> ORGANISM: Triticum aestivum

<400> SEQUENCE: 5

| | |
|---|---|
| atgcggatgg gcgggacacg cgcgcttgtc cgtccctggc ccgcatgtca gcgacacaaa | 60 |

```
gtaaaacccc tctgcggccc ctttggcgcc atcctccccc cccaaaccct cccacatccc   120
gcccgtccca ctcccttccc cgtccatggc cgacgcccag ccgaactcct gcgggctggc   180
cgtcgacccc ccccccccg aatggccaag aagaagaagg acaaggcgcc aaggaagccg   240
cggtcggagt gcacgccgga ggagatcgcc aagttggacg cggaatcggt gaagaggagg   300
ggccggaggg cggtcgccaa accaacatc gccgcggcca agagagttgc cgagcgcgct   360
gcgattgagg ccgcacggca caaggccgag gtcgaggaga aggaggccat cgtcagcaaa   420
gcgcgcgccc ttctcatggc tggcatttgt cgtccgcccg gtttctctgg aagggccgtc   480
ggtccggcga gcacaaggtc gtcggtcgcc cggcctccgc actgccagtc gccgacatcg   540
cggaccacgc ccttgtcgcc cggctttcct ccaccaaggc acgacggcca gacccgtttc   600
gggggtcgc cggatgtgag catgatcgcg ccgtccacac cacgcccctc ggccgtcatc   660
gacctcaacg tcacccttgg gtccagcagc ggcggccggc cgtcggtcga gatgcaaaga   720
aagcaagcac ggctgccgtt taccggcacc atgccgtccc ccgcgtcttt gttcgatgga   780
atgccaacac caacgatacc agtcgacgac ccctatcagg atggctgcgg ccagttcact   840
gccgatgaag aggccaacga ccgtgctgac tacgatcatg gtgactcgtg gcatgaagac   900
gatgacattt atgtcgaagg tgatggtgat gaagaagaaa gaaatgacgt tgacattagt   960
gttgagccat tgttcatcga cgagctgaca caaagagcgg aagcacaaaa gaagaggaag  1020
agcattcgca cgagttcata cacacaagat gaggacaagt tgatttgcca agcttggatg  1080
gagattagcc aagatccaag gaccggcgcg caacaaaagg gtattgtttt ttggacgaga  1140
gtccacaaaa cattccatga aggaagttg tttgagccct accaatttga agcaaccgt   1200
ggcatcggct cgattcaaaa gagatggttg ttcatccaac aagagtgcaa caagtatcaa  1260
gccgcatttg agagcgttca agcacggccc gtgagtggtc tcggcgttgg ggacatggca  1320
tttcaatctt tggaggcatt caaggcccgg cacaatgaca cgccgttcac tcttacgcat  1380
tgttggacta tgatcaacat ttgccctaag ttcaaggacc aataccgtga actccaaagg  1440
aagagaggcc tgaagacggc caagtacgcg ggaggtggag atggcgaggc gttcaagagg  1500
ccgaggggca agaccaactc caaggttgac gacatacgtg atgcctcatc catggcattg  1560
catgacactt tgcatgacat gatgtcgcaa aaggatgtga ggaacgagaa gaagcggcaa  1620
agcaatggca agcaaatgaa gcaataccta gagcttcaaa cgaagaagct tgagatggag  1680
gaggcggcta agagaaggaa gatcggcatg gaggaggagg tccggcagag gcagctcgac  1740
atcgaggcca tcaatgccgc caccaaagcg aaggaggtgg ccctcgcgat catgagcgtg  1800
gacttgtcga agatgagtga aagacgagg gcctggctgg catgggtacc gcgcgcccgc  1860
tgggccgctg gccatgtgcc ggcgagaaaa acatttattt tgaaggtcgg ctgtgttgcc  1920
ggccgctggc tgtgttgccg acgaggacgt ccattcattt tggaggctgg ctgtgttagc  1980
ggccgctggc gtgatggacg tgtatgtcgc tggctttgtt gccggcacgc ggacatgggg  2040
ctggacgcac ggccaccgca tctcagacca ggcccggaca cgaccccatc tcctgaccaa  2100
acggacagaa tccggacaaa tcgaacatcc gggtcgcgcg gtggagttgg ccttaggccc  2160
gcagttcaag cgcgcggcgc ggcgcagatc tctaccgtcg ggcaggagga aagcccgag   2220
gaaccaatga agcctgagcc cgacccgggc gtcgccgtct ggcagcccga cggcgacgga  2280
gagatcgaca tggatctgct gcctccgatt agcgcgtctc tgggcgccat ggcctccctt  2340
tccgggaagc tggatgcgct ccaggatacc gaactcaagg atgagatccg gaaacttgga  2400
```

```
tcccggctgc tgaagctctc cgagccacat gaaccccgtc atgcggcgag gatctggatg    2460
aatgaggcgc gcgaactatc ctatgacatg gtaaactgtg tcgacgcgga tgcagactgg    2520
atcgacaaga tgtcaagaat attcaagcca cgcgtgaagg aggccaatgg gcggtaccac    2580
agatacaagc ttgagagcgt ccccagccgt gcagctgtct tagcgatccc aatggtggtc    2640
ggcgacgccg gccggaagcc agatctactc gtcggccttc acgccaatgg tggcgccttc    2700
gaaacgctcc gcaaaaatct gattgaccgg gacgagcagc tcaaggcgct attcgttgtt    2760
ggtgttggag gaatcggcaa gaccacgctt gccaagagc tatggcgtga gcacaaaccc    2820
gggcaccact tctgctgccg ggctttcgtg cggaccgcca agaaacctga catgaggagg    2880
atcctgagga gcatactcgc acaagttcgt ccggatcaac cacccgtcgc taatgaggtg    2940
cacgagctca ttcacgacct caccgagcat ctaaaggata aagggtcgg agcagcggag    3000 gcgtgcgcag ccatctctct cctaacgcgc ggccggagaa taaccacaca cggaggctgg    3060
tcgtctcggc cggcgcgccg ttgcggagaa ggagtggacc tccgtctctc gcggcccggg    3120
ccgaagcctc gacgacggag cggatgtgct gcggtcgcgg tccgggagcg ccatcgccgc    3180
tcgatctggg tagcaagaga aggtgagggc gcggcggcgt ggggagaaga aggcggaggg    3240
agacggcgtc gccggtggga gagaaggtac ttcattataa ttgatgactt atgggataca    3300
tcagtatggg atgttgcagc ccgtgctttc ccaaagggta accaaggcag caggatagta    3360
acaacaacgg aaattgagga tgttgctctt gcatgttgtt atcagtcaaa gtacgtgctt    3420
aagatggaac atcttagcga gagtcactca agagagttgt tcaccagtgc agtgtttcgc    3480
tctggagaac aacactctca ccacgtaggt gaagtgccag atgagattat aagaagatgt    3540
gctggtttac cacaggcaat tatcagcata tccagtgttc tagcaagcca tggagaagca    3600
aatacagtaa agaactggga gcaaatacaa aacagtttgc caacaaatac aacttctgac    3660
gagatactga aagaagtact gattttttgc tataatagtc ttcccagttg tgttcagaca    3720
tgtctgttgc atcttagtat atacccggag aactatgtta tcttgaagga agatataacg    3780
aagcaatggg ttgctgaagg tctcatcagt gcaccaacag agaaagaaaa aatggaaatt    3840
gccaggagct attttgatat gcttgtcagt atgggcatga tccaacatat agacgtagac    3900
tatggcaatg atgttttgta ctatgcggtg catcacatgg tacatgatat cattacatcc    3960
aagtccatag aagagaattt tgttaaagta atagattatt ctcaaagggc ggtacggttt    4020
tctaacaagg ttagtcgtct gtccctccag tttggcggtg caacatatgc aactacacca    4080
gcacgtatcg aactgtcgca agtgcgatct cttgcttata ctggactgaa gagctgcttg    4140
ccttccatct cagagtttaa gcttctccgg gtactgattc tccatatttg ggctgatcaa    4200
ccaagcacat gtgtcactcg caaaaaaaag aaccaagcac aggtgacatg caacggcacc    4260
gtgcatcttc caaaacagat gcgatgtctg aaacacttgg aaacacttga ataaatgca    4320 acagtagcag ccattccatc ggatattgtt catcttcgga gcttgttgca tctccgtcta    4380
ggaggtggga cagaactgcc tgatgtgaca ggtgtcctca caaatgttac cctgaatctt    4440
cctagtgctg ccactttatt ggatgattcg agcagttctc ccgattcact gaacacaatg    4500
gagctattgc cacccatttg cagaatcccc aactggattg gacagcttac tgacctctgc    4560
attctgaaag ttgtcgtcag agaactgcta agggatgata tcagtaacct ggaaagattg    4620
ccagcactca ctgttctctc cttgtacgtc cagcaaagaa atacagaact aatcattttc    4680
gaagccggag cattttctgc tctcgagtgt tttgagttca ggtgtggtga actgcagctg    4740
atgtttcagg aaggagcaat gcccaatctt cacagaatca agctaggttt caatgctcac    4800
```

-continued

```
aaaggagaac agtatgatcg tcttcttagc ggcattgaga acctgtctga cgtccaggaa    4860
atttctggaa taattgggc agcccctggt gccgatgagc atgactttca ggctgcagaa    4920
tctgcattca tgaaagctgt tagcaagctc tctagtaaag tcagtgtaaa agagcagat    4980 atggttgagg aagagggtgg cctggcagaa aacaggatg tgatccgaga gaaagatgca    5040
tcaagacatg taataagtga acagcctgca attctgaaac aagagtctga ggaagatata    5100
aagcaaaatg ctggtggcag tttgcctagc ggcattaaga acctgtcaaa cgtccaggaa    5160
atttctggaa taactggggt agccacaggt gctgaggaac atgaaattca ggctgcagaa    5220
tctgcattga tgaaatccgt cagtgagcaa cctagtaagg tcactataaa aggagcagat    5280
atggttgagc aagggtatgg tccggcagac aaacaacatg tgagccgaga gaaagatgta    5340
tcaagccatt taagaagtga acaacctgca attgtgaaac aagagtccgg tggcaactct    5400
cagttcattc aatggagaag caatagcaag gaaacttcaa acgtggtgca aggtttgtca    5460
gggaaccgag aacttcgtgg cggtgctgtt ggagaagtta acaaggaaga gaacgtcag    5520 aatagcctgg cgagaggcaa agcagcatg gatattaaac tcgtggagat cgaagccatc    5580
acaaacaatt ttgcagagga acagaaagtc ggcagcggtg ggtacggaga tgtttacagg    5640
gccactcaca aaggagagga agttgccgtg aagaagctcc atcaactgca gggactcgat    5700
gataagcaat tcgacagcga gttccgtaac cttcgtaata tacgccacca aaatgttgtg    5760
cggctaattg gctactgcca cgagtctcgc aagaaataca tggagcacaa gggggagctc    5820
atcttcgcca aagagatgga gcgcgtgctc tgcttcgaat atatgcacgg cggaagcctc    5880
gataaacata ttacagatga atcttgtgag cttgattggc cgacgtgtta caaaatcatc    5940
aaagggactt gtgagggctt aaatcacctt cacacctcgc agggaagcc tattttacat    6000 ctagacataa aaccagccaa catattgctg gataagagca tgacgcctaa aatcgccgat    6060
cttggtttgt ccaaacttgt ttcttcgaca ttaacacata aaacagagat tgtcaaaggg    6120
acacaagggt acatgccgcc agagtatgta gacaatggcc agatatcgaa caagtttgac    6180
gtgtttagtt ttggcgtagt aattataaaa atgatggccg gtaacgtggg ctacttccgt    6240
tgtgctgaaa tgtctcacaa agagtttatt gagctggtaa ctaaaaactg ggtgaaaagg    6300
ttgctgacag agcctggata ttcctcgcac gaaaccgaca tgctaggagt cactagatgt    6360
gttgaaattg cattaagatg tgtggacaag gaccgaaaca aaaggccctg tattaaggat    6420
gttgtccatg agctggagga actagaagct gagatcaaga aaatgtccct atcttccgac    6480
cagtcaaaag gcctaagtct gcaggcaagc atccttagaa gctgtgacac caacattctc    6540
tcggtggatc cgaccctcga gctgcggttc gtctttgagc caaggaagga gacgtcgtgc    6600
tgtctgcaga tgaccaacaa gacgggtggc ttcatcgcat tcaacatatt gatgaacaag    6660
aacaagtata gtgtgcggcc aagccaaggg accatgccac cgtgctccag gcgttatgtt    6720
gtcgtgacac tgtcagcgca agaggcggcg ccgccataca tgcggtgtga cgacatgctc    6780
ctagtgcaga gcaccagcat cacccaagat cttggtgaga tcaattatca agaattgttc    6840
gacgtggcca gggcggataa ggtggttgat gtggtgcatc tgccaatcgc atatgtcacg    6900
ttagaagagt ag                                                        6912
```

<210> SEQ ID NO 6
<211> LENGTH: 2303
<212> TYPE: PRT
<213> ORGANISM: Triticum aestivum

```
<400> SEQUENCE: 6

Met Arg Met Gly Gly Thr Arg Ala Leu Val Arg Pro Trp Pro Ala Cys
1               5                   10                  15

Gln Arg His Lys Val Lys Pro Leu Cys Gly Pro Phe Gly Ala Ile Leu
            20                  25                  30

Pro Pro Gln Thr Leu Pro His Pro Ala Arg Pro Thr Pro Phe Pro Val
        35                  40                  45

His Gly Arg Arg Pro Ala Glu Leu Leu Arg Ala Gly Arg Arg Pro Pro
    50                  55                  60

Pro Pro Arg Met Ala Lys Lys Lys Asp Lys Ala Pro Arg Lys Pro
65                  70                  75                  80

Arg Ser Glu Cys Thr Pro Glu Ile Ala Lys Leu Asp Ala Glu Ser
                85                  90                  95

Val Lys Arg Arg Gly Arg Ala Val Ala Lys Thr Asn Ile Ala Ala
                100                 105                 110

Ala Lys Arg Val Ala Glu Arg Ala Ala Ile Glu Ala Ala Arg His Lys
            115                 120                 125

Ala Glu Val Glu Glu Lys Glu Ala Ile Val Ser Lys Ala Arg Ala Leu
        130                 135                 140

Leu Met Ala Gly Ile Cys Arg Pro Pro Gly Phe Ser Gly Arg Ala Val
145                 150                 155                 160

Gly Pro Ala Ser Thr Arg Ser Ser Val Ala Arg Pro Pro His Cys Gln
                165                 170                 175

Ser Pro Thr Ser Arg Thr Thr Pro Leu Ser Pro Gly Phe Pro Pro Pro
                180                 185                 190

Arg His Asp Gly Gln Thr Arg Phe Gly Gly Ser Pro Asp Val Ser Met
            195                 200                 205

Ile Ala Pro Ser Thr Pro Arg Pro Ser Ala Val Ile Asp Leu Asn Val
        210                 215                 220

Thr Leu Gly Ser Ser Gly Gly Arg Pro Ser Val Glu Met Gln Arg
225                 230                 235                 240

Lys Gln Ala Arg Leu Pro Phe Thr Gly Thr Met Pro Ser Pro Arg Val
                245                 250                 255

Leu Phe Asp Gly Met Pro Thr Pro Thr Ile Pro Val Asp Asp Pro Tyr
                260                 265                 270

Gln Asp Gly Cys Gly Gln Phe Thr Ala Asp Glu Glu Ala Asn Asp Arg
            275                 280                 285

Ala Asp Tyr Asp His Gly Asp Ser Trp His Glu Asp Asp Ile Tyr
        290                 295                 300

Val Glu Gly Asp Gly Asp Glu Glu Arg Asn Asp Val Asp Ile Ser
305                 310                 315                 320

Val Glu Pro Leu Phe Ile Asp Glu Leu Thr Gln Arg Ala Glu Ala Gln
                325                 330                 335

Lys Lys Arg Lys Ser Ile Arg Thr Ser Ser Tyr Thr Gln Asp Glu Asp
            340                 345                 350

Lys Leu Ile Cys Gln Ala Trp Met Glu Ile Ser Gln Asp Pro Arg Thr
        355                 360                 365

Gly Ala Gln Gln Lys Gly Ile Val Phe Trp Thr Arg Val His Lys Thr
    370                 375                 380

Phe His Glu Arg Lys Leu Phe Glu Pro Tyr Gln Phe Glu Ser Asn Arg
385                 390                 395                 400

Gly Ile Gly Ser Ile Gln Lys Arg Trp Leu Phe Ile Gln Gln Glu Cys
                405                 410                 415
```

```
Asn Lys Tyr Gln Ala Ala Phe Glu Ser Val Gln Ala Arg Pro Val Ser
            420                 425                 430

Gly Leu Gly Val Gly Asp Met Ala Phe Gln Ser Leu Glu Ala Phe Lys
        435                 440                 445

Ala Arg His Asn Asp Thr Pro Phe Thr Leu Thr His Cys Trp Thr Met
450                 455                 460

Ile Asn Ile Cys Pro Lys Phe Lys Asp Gln Tyr Arg Glu Leu Gln Arg
465                 470                 475                 480

Lys Arg Gly Leu Lys Thr Ala Lys Tyr Ala Gly Gly Asp Gly Glu
                485                 490                 495

Ala Phe Lys Arg Pro Arg Gly Lys Thr Asn Ser Lys Val Asp Asp Ile
                500                 505                 510

Arg Asp Ala Ser Ser Met Ala Leu His Asp Thr Leu His Asp Met Met
            515                 520                 525

Ser Gln Lys Asp Val Arg Asn Glu Lys Lys Arg Gln Ser Asn Gly Lys
530                 535                 540

Gln Met Lys Gln Tyr Leu Glu Leu Gln Thr Lys Lys Leu Glu Met Glu
545                 550                 555                 560

Glu Ala Ala Lys Arg Arg Lys Ile Gly Met Glu Glu Val Arg Gln
                565                 570                 575

Arg Gln Leu Asp Ile Glu Ala Ile Asn Ala Ala Thr Lys Ala Lys Glu
            580                 585                 590

Val Ala Leu Ala Ile Met Ser Val Asp Leu Ser Lys Met Ser Glu Lys
            595                 600                 605

Thr Arg Ala Trp Leu Ala Trp Val Pro Arg Ala Arg Trp Ala Ala Gly
            610                 615                 620

His Val Pro Ala Arg Lys Thr Phe Ile Leu Lys Val Gly Cys Val Ala
625                 630                 635                 640

Gly Arg Trp Leu Cys Cys Arg Arg Gly Arg Pro Phe Ile Leu Glu Ala
                645                 650                 655

Gly Cys Val Ser Gly Arg Trp Arg Asp Gly Arg Val Cys Arg Trp Leu
                660                 665                 670

Cys Cys Arg His Ala Asp Met Gly Leu Asp Ala Arg Pro Pro His Leu
            675                 680                 685

Arg Pro Gly Pro Asp Thr Thr Pro Ser Pro Asp Gln Thr Asp Arg Ile
690                 695                 700

Arg Thr Asn Arg Thr Ser Gly Ser Arg Gly Gly Val Gly Leu Arg Pro
705                 710                 715                 720

Ala Val Gln Ala Arg Gly Ala Ala Gln Ile Ser Thr Val Gly Gln Glu
                725                 730                 735

Glu Lys Pro Glu Glu Pro Met Lys Pro Glu Pro Asp Pro Gly Val Ala
            740                 745                 750

Val Trp Gln Pro Asp Gly Asp Gly Glu Ile Asp Met Asp Leu Leu Pro
            755                 760                 765

Pro Ile Ser Ala Ser Leu Gly Ala Met Ala Ser Ser Gly Lys Leu
            770                 775                 780

Asp Ala Leu Gln Asp Thr Glu Leu Lys Asp Glu Ile Arg Lys Leu Gly
785                 790                 795                 800

Ser Arg Leu Leu Lys Leu Ser Glu Pro His Glu Pro Arg His Ala Ala
                805                 810                 815

Arg Ile Trp Met Asn Glu Ala Arg Glu Leu Ser Tyr Asp Met Val Asn
            820                 825                 830
```

-continued

```
Cys Val Asp Ala Asp Ala Asp Trp Ile Asp Lys Met Ser Arg Ile Phe
            835                 840                 845

Lys Pro Arg Val Lys Glu Ala Asn Gly Arg Tyr His Arg Tyr Lys Leu
850                 855                 860

Glu Ser Val Pro Ser Arg Ala Ala Val Leu Ala Ile Pro Met Val Val
865                 870                 875                 880

Gly Asp Ala Gly Arg Lys Pro Asp Leu Leu Val Gly Leu His Ala Asn
                885                 890                 895

Gly Gly Ala Phe Glu Thr Leu Arg Lys Asn Leu Ile Asp Arg Asp Glu
            900                 905                 910

Gln Leu Lys Ala Leu Phe Val Val Gly Val Gly Gly Ile Gly Lys Thr
            915                 920                 925

Thr Leu Ala Lys Glu Leu Trp Arg Glu His Lys Pro Gly His His Phe
        930                 935                 940

Cys Cys Arg Ala Phe Val Arg Thr Ala Lys Lys Pro Asp Met Arg Arg
945                 950                 955                 960

Ile Leu Arg Ser Ile Leu Ala Gln Val Arg Pro Asp Gln Pro Pro Val
                965                 970                 975

Ala Asn Glu Val His Glu Leu Ile His Asp Leu Thr Glu His Leu Lys
            980                 985                 990

Asp Lys Arg Val Gly Ala Ala Glu  Ala Cys Ala Ala Ile  Ser Leu Leu
        995                 1000                1005

Thr Arg  Gly Arg Arg Ile Thr  Thr His Gly Gly Trp  Ser Ser Arg
    1010                1015                1020

Pro Ala  Arg Arg Cys Gly Glu  Gly Val Asp Leu Arg  Leu Ser Arg
    1025                1030                1035

Pro Gly  Pro Lys Pro Arg Arg  Arg Ser Gly Cys Ala  Ala Val Ala
    1040                1045                1050

Val Arg  Glu Arg His Arg Arg  Ser Ile Trp Val Ala  Arg Glu Gly
    1055                1060                1065

Glu Gly  Ala Ala Ala Trp Gly  Glu Glu Gly Gly  Arg Arg Arg
    1070                1075                1080

Arg Arg  Trp Glu Arg Arg Tyr  Phe Ile Ile Ile Asp  Asp Leu Trp
    1085                1090                1095

Asp Thr  Ser Val Trp Asp Val  Ala Ala Arg Ala Phe  Pro Lys Gly
    1100                1105                1110

Asn Gln  Gly Ser Arg Ile Val  Thr Thr Thr Glu Ile  Glu Asp Val
    1115                1120                1125

Ala Leu  Ala Cys Cys Tyr Gln  Ser Lys Tyr Val Leu  Lys Met Glu
    1130                1135                1140

His Leu  Ser Glu Ser His Ser  Arg Glu Leu Phe Thr  Ser Ala Val
    1145                1150                1155

Phe Arg  Ser Gly Glu Gln His  Ser His His Val Gly  Glu Val Pro
    1160                1165                1170

Asp Glu  Ile Ile Arg Arg Cys  Ala Gly Leu Pro Gln  Ala Ile Ile
    1175                1180                1185

Ser Ile  Ser Ser Val Leu Ala  Ser His Gly Glu Ala  Asn Thr Val
    1190                1195                1200

Lys Asn  Trp Glu Gln Ile Gln  Asn Ser Leu Pro Thr  Asn Thr Thr
    1205                1210                1215

Ser Asp  Glu Ile Leu Lys Glu  Val Leu Ile Phe Cys  Tyr Asn Ser
    1220                1225                1230

Leu Pro  Ser Cys Val Gln Thr  Cys Leu Leu His Leu  Ser Ile Tyr
```

-continued

```
              1235               1240                1245
Pro Glu  Asn Tyr  Val Ile  Leu Lys  Glu Asp  Ile Thr  Lys Gln  Trp
         1250              1255               1260

Val Ala  Glu Gly  Leu Ile  Ser Ala  Pro Thr  Glu Lys  Glu Lys  Met
         1265              1270               1275

Glu Ile  Ala Arg  Ser Tyr  Phe Asp  Met Leu  Val Ser  Met Gly  Met
         1280              1285               1290

Ile Gln  His Ile  Asp Val  Asp Tyr  Gly Asn  Asp Val  Leu Tyr  Tyr
         1295              1300               1305

Ala Val  His His  Met Val  His Asp  Ile Ile  Thr Ser  Lys Ser  Ile
         1310              1315               1320

Glu Glu  Asn Phe  Val Lys  Val Ile  Asp Tyr  Ser Gln  Arg Ala  Val
         1325              1330               1335

Arg Phe  Ser Asn  Lys Val  Ser Arg  Leu Ser  Leu Gln  Phe Gly  Gly
         1340              1345               1350

Ala Thr  Tyr Ala  Thr Thr  Pro Ala  Arg Ile  Glu Leu  Ser Gln  Val
         1355              1360               1365

Arg Ser  Leu Ala  Tyr Thr  Gly Leu  Lys Ser  Cys Leu  Pro Ser  Ile
         1370              1375               1380

Ser Glu  Phe Lys  Leu Leu  Arg Val  Leu Ile  Leu His  Ile Trp  Ala
         1385              1390               1395

Asp Gln  Pro Ser  Thr Cys  Val Thr  Arg Lys  Lys Asn  Gln Ala
         1400              1405               1410

Gln Val  Thr Cys  Asn Gly  Thr Val  His Leu  Pro Lys  Gln Met  Arg
         1415              1420               1425

Cys Leu  Lys His  Leu Glu  Thr Leu  Glu Ile  Asn Ala  Thr Val  Ala
         1430              1435               1440

Ala Ile  Pro Ser  Asp Ile  Val His  Leu Arg  Ser Leu  Leu His  Leu
         1445              1450               1455

Arg Leu  Gly Gly  Gly Thr  Glu Leu  Pro Asp  Val Thr  Gly Val  Leu
         1460              1465               1470

Thr Asn  Val Thr  Leu Asn  Leu Pro  Ser Ala  Ala Thr  Leu Leu  Asp
         1475              1480               1485

Asp Ser  Ser Ser  Ser Pro  Asp Ser  Leu Asn  Thr Met  Glu Leu  Leu
         1490              1495               1500

Pro Pro  Ile Cys  Arg Ile  Pro Asn  Trp Ile  Gly Gln  Leu Thr  Asp
         1505              1510               1515

Leu Cys  Ile Leu  Lys Val  Val Arg  Glu Leu  Leu Arg  Asp Asp
         1520              1525               1530

Ile Ser  Asn Leu  Glu Arg  Leu Pro  Ala Leu  Thr Val  Leu Ser  Leu
         1535              1540               1545

Tyr Val  Gln Gln  Arg Asn  Thr Glu  Leu Ile  Ile Phe  Glu Ala  Gly
         1550              1555               1560

Ala Phe  Ser Ala  Leu Glu  Cys Phe  Glu Phe  Arg Cys  Gly Glu  Leu
         1565              1570               1575

Gln Leu  Met Phe  Gln Glu  Gly Ala  Met Pro  Asn Leu  His Arg  Ile
         1580              1585               1590

Lys Leu  Gly Phe  Asn Ala  His Lys  Gly Glu  Gln Tyr  Asp Arg  Leu
         1595              1600               1605

Leu Ser  Gly Ile  Glu Asn  Leu Ser  Asp Val  Gln Glu  Ile Ser  Gly
         1610              1615               1620

Ile Ile  Gly Ala  Ala Pro  Gly Ala  Asp Glu  His Asp  Phe Gln  Ala
         1625              1630               1635
```

```
Ala Glu Ser Ala Phe Met Lys Ala Val Ser Lys Leu Ser Ser Lys
    1640                1645                1650

Val Ser Val Lys Arg Ala Asp Met Val Glu Glu Glu Gly Gly Leu
    1655                1660                1665

Ala Glu Lys Gln Asp Val Ile Arg Glu Lys Asp Ala Ser Arg His
    1670                1675                1680

Val Ile Ser Glu Gln Pro Ala Ile Leu Lys Gln Glu Ser Glu Glu
    1685                1690                1695

Asp Ile Lys Gln Asn Ala Gly Gly Ser Leu Pro Ser Gly Ile Lys
    1700                1705                1710

Asn Leu Ser Asn Val Gln Glu Ile Ser Gly Ile Thr Gly Val Ala
    1715                1720                1725

Thr Gly Ala Glu Glu His Glu Ile Gln Ala Ala Glu Ser Ala Leu
    1730                1735                1740

Met Lys Ser Val Ser Glu Gln Pro Ser Lys Val Thr Ile Lys Gly
    1745                1750                1755

Ala Asp Met Val Glu Gln Gly Tyr Gly Pro Ala Asp Lys Gln His
    1760                1765                1770

Val Ser Arg Glu Lys Asp Val Ser Ser His Leu Arg Ser Glu Gln
    1775                1780                1785

Pro Ala Ile Val Lys Gln Glu Ser Gly Gly Asn Ser Gln Phe Ile
    1790                1795                1800

Gln Trp Arg Ser Asn Ser Lys Glu Thr Ser Asn Val Val Gln Gly
    1805                1810                1815

Leu Ser Gly Asn Arg Glu Leu Arg Gly Gly Ala Val Gly Glu Val
    1820                1825                1830

Asn Lys Glu Glu Glu Arg Gln Asn Ser Leu Ala Arg Gly Lys Ser
    1835                1840                1845

Ser Met Asp Ile Lys Leu Val Glu Ile Glu Ala Ile Thr Asn Asn
    1850                1855                1860

Phe Ala Glu Glu Gln Lys Val Gly Ser Gly Gly Tyr Gly Asp Val
    1865                1870                1875

Tyr Arg Ala Thr His Lys Gly Glu Glu Val Ala Val Lys Lys Leu
    1880                1885                1890

His Gln Leu Gln Gly Leu Asp Asp Lys Gln Phe Asp Ser Glu Phe
    1895                1900                1905

Arg Asn Leu Arg Asn Ile Arg His Gln Asn Val Val Arg Leu Ile
    1910                1915                1920

Gly Tyr Cys His Glu Ser Arg Lys Lys Tyr Met Glu His Lys Gly
    1925                1930                1935

Glu Leu Ile Phe Ala Lys Glu Met Glu Arg Val Leu Cys Phe Glu
    1940                1945                1950

Tyr Met His Gly Gly Ser Leu Asp Lys His Ile Thr Asp Glu Ser
    1955                1960                1965

Cys Glu Leu Asp Trp Pro Thr Cys Tyr Lys Ile Ile Lys Gly Thr
    1970                1975                1980

Cys Glu Gly Leu Asn His Leu His Thr Ser Gln Gly Lys Pro Ile
    1985                1990                1995

Leu His Leu Asp Ile Lys Pro Ala Asn Ile Leu Leu Asp Lys Ser
    2000                2005                2010

Met Thr Pro Lys Ile Ala Asp Leu Gly Leu Ser Lys Leu Val Ser
    2015                2020                2025
```

| | | | | | | | | | | |
|---|---|---|---|---|---|---|---|---|---|---|
| Ser | Thr | Leu | Thr | His | Lys | Thr | Glu | Ile | Val | Lys | Gly | Thr | Gln | Gly |
| | 2030 | | | | 2035 | | | | 2040 | |

Ser Thr Leu Thr His Lys Thr Glu Ile Val Lys Gly Thr Gln Gly
    2030                2035                2040

Tyr Met Pro Pro Glu Tyr Val Asp Asn Gly Gln Ile Ser Asn Lys
    2045                2050                2055

Phe Asp Val Phe Ser Phe Gly Val Val Ile Ile Lys Met Met Ala
    2060                2065                2070

Gly Asn Val Gly Tyr Phe Arg Cys Ala Glu Met Ser His Lys Glu
    2075                2080                2085

Phe Ile Glu Leu Val Thr Lys Asn Trp Val Lys Arg Leu Leu Thr
    2090                2095                2100

Glu Pro Gly Tyr Ser Ser His Glu Thr Asp Met Leu Gly Val Thr
    2105                2110                2115

Arg Cys Val Glu Ile Ala Leu Arg Cys Val Asp Lys Asp Arg Asn
    2120                2125                2130

Lys Arg Pro Cys Ile Lys Asp Val Val His Glu Leu Glu Glu Leu
    2135                2140                2145

Glu Ala Glu Ile Lys Lys Met Ser Leu Ser Ser Asp Gln Ser Lys
    2150                2155                2160

Gly Leu Ser Leu Gln Ala Ser Ile Leu Arg Ser Cys Asp Thr Asn
    2165                2170                2175

Ile Leu Ser Val Asp Pro Thr Leu Glu Leu Arg Phe Val Phe Glu
    2180                2185                2190

Pro Arg Lys Glu Thr Ser Cys Cys Leu Gln Met Thr Asn Lys Thr
    2195                2200                2205

Gly Gly Phe Ile Ala Phe Asn Ile Leu Met Asn Lys Asn Lys Tyr
    2210                2215                2220

Ser Val Arg Pro Ser Gln Gly Thr Met Pro Pro Cys Ser Arg Arg
    2225                2230                2235

Tyr Val Val Val Thr Leu Ser Ala Gln Glu Ala Ala Pro Pro Tyr
    2240                2245                2250

Met Arg Cys Asp Asp Met Leu Leu Val Gln Ser Thr Ser Ile Thr
    2255                2260                2265

Gln Asp Leu Gly Glu Ile Asn Tyr Gln Glu Leu Phe Asp Val Ala
    2270                2275                2280

Arg Ala Asp Lys Val Val Asp Val Val His Leu Pro Ile Ala Tyr
    2285                2290                2295

Val Thr Leu Glu Glu
    2300

<210> SEQ ID NO 7
<211> LENGTH: 1173
<212> TYPE: DNA
<213> ORGANISM: Artificial Sequence
<220> FEATURE:
<223> OTHER INFORMATION: Probe LRR RGA 1

<400> SEQUENCE: 7

```
catggaatca tgaatcagtt aatgttgtat aagtccaggt cttcgaattt catttctaca    60
tctattaatg ataataaccg aagtaattac cgtcacctgg ttatccagaa taacagaaac   120
ggtaaaagct tcagtccaga aacaagtgtc aagggcaagc agctgcgtcc ccggtctcta   180
acagtctttg ggagtgcaga agaagccgtt ccagatttga agagttgtga gctgctgaga   240
gtgttggatc tgaaagaatg caatgatttg agggaccaac atctcgagca catatacaag   300
ctgttgcatc taaatatatct ggccctcggg gattctagta gcaaatatct ggatagaatg   360
```

| | |
|---|---|
| ggaaagctac attgtttaga dacactcgac ttgaggaaga ggaaaatcga gatactgcca | 420 |
| gtggaagtca tcagtttgcc ccacctagca catctgttgg gaaagttcaa gctaaacaag | 480 |
| ttgggtaaga ggaagcttaa agagttccgg tcaaacaaat gcaacttgga gactgtagca | 540 |
| ggagttattg ttgacagcga ctctggattc ctggaattga tggttcattt gaagcaactt | 600 |
| agaaaggtca agatatggtg cgagctcact agcacagatt gcaagaacat actgggttca | 660 |
| ctttcaaagg ccattcaaaa gtttgctaag gatggcatag atactccagt aggtgaccgt | 720 |
| ggtcgcctat cactccattt caacaattat tctgaaggtc tgttgcactg tgaagatgac | 780 |
| cccacatttc ttggttatct taactcgctg aaactgcaag gcagcctgag tcagttccct | 840 |
| aagtttgcta agtccctcga tggtctgcaa gaactgtgcc ttacatatac taatctgacg | 900 |
| ggggctgatc ttctactagg tctgtgtagg ctacgacgct tggtttatct caaactgatc | 960 |
| gaagtccatc ttgcggattt agacttagaa gatggggatc tcccaaaact gcaacgtcta | 1020 |
| tgcctcgtgg tgcaacagcc cagattcccc agtatccgaa caggcgctct gccgaaacta | 1080 |
| acttcaattc agttgctctg tggtggtctg gaagatcttg gtggcatcga aatggaattg | 1140 |
| ttcaaggacc tccgggaaat cgctcttgat tct | 1173 |

<210> SEQ ID NO 8
<211> LENGTH: 968
<212> TYPE: DNA
<213> ORGANISM: Artificial Sequence
<220> FEATURE:
<223> OTHER INFORMATION: Probe LRR RGA 2

<400> SEQUENCE: 8

| | |
|---|---|
| gtgcatcaca tggtacatga tatcattaca tccaagtcca tagaagagaa ttttgttaaa | 60 |
| gtaatagatt attctcaaag ggcggtacgg ttttctaaca aggttagtcg tctgtccctc | 120 |
| cagtttggcg gtgcaacata tgcaactaca ccagcacgta tcgaactgtc gcaagtgcga | 180 |
| tctcttgctt atactggact gaagagctgc ttgccttcca tctcagagtt taagcttctc | 240 |
| cgggtactga ttctccatat ttgggctgat caaccaagca catgtgtcac tcgcaaaaaa | 300 |
| aagaaccaag cacaggtgtc cacctcgagt gtatctctcg attgcttcta ttaatatatt | 360 |
| tgcaggtgac atgcaacggc accgtgcatc ttccaaaaca gatgcgatgt ctgaaacact | 420 |
| tggaaacact tgaaataaat gcaacagtag cagccattcc atcggatatt gttcatcttc | 480 |
| ggagcttgtt gcatctccgt ctaggaggtg ggacagaact gcctgatgtg acaggtgtcc | 540 |
| tcacaaatgt taccctgaat cttcctagtg ctgccacttt attggatgat tcgagcagtt | 600 |
| ctcccgattc actgaacaca atggagctat tgccacccat ttgcagaatc cccaactgga | 660 |
| ttggacagct tactgacctc tgcattctga aagttgtcgt cagagaactg ctaagggatg | 720 |
| atatcagtaa cctggaaaga ttgccagcac tcactgttct ctccttgtac gtccagcaaa | 780 |
| gaaatacaga actaatcatt ttcgaagccg gagcattttc tgctctcgag tgttttgagt | 840 |
| tcaggtgtgg tgaactgcag ctgatgtttc aggaaggagc aatgcccaat cttcacagaa | 900 |
| tcaagctagg tttcaatgct cacaaaggag aacagtatga tcgtcttctt agcggcattg | 960 |
| agaacctg | 968 |

<210> SEQ ID NO 9
<211> LENGTH: 92
<212> TYPE: DNA
<213> ORGANISM: Artificial Sequence
<220> FEATURE:
<223> OTHER INFORMATION: Marker Wa_c6957_32R

<400> SEQUENCE: 9
cgggacagcc aagagaaatt ccatttggcg atcgttcaaa tgtgcactgc attctcgtac    60
tgccgtcgcc gtcgtctgtc tcttgactgt cg                                 92

<210> SEQ ID NO 10
<211> LENGTH: 92
<212> TYPE: DNA
<213> ORGANISM: Artificial Sequence
<220> FEATURE:
<223> OTHER INFORMATION: Marker Wa_c6957_32S

<400> SEQUENCE: 10
cgggacagcc aagagaaatt ccatttggcg accgttcaaa tgtgcactgc attctcgtac    60
tgccgtcgcc gtcgtctgtc tcttgactgt cg                                 92

<210> SEQ ID NO 11
<211> LENGTH: 215
<212> TYPE: DNA
<213> ORGANISM: Artificial Sequence
<220> FEATURE:
<223> OTHER INFORMATION: Marker Excalibur_c1787R

<400> SEQUENCE: 11
catattgatg aacaagaaca agtatagtgt gcggccaagc caagggacca tgccaccgtg    60
ctccaggcgt tatgttgtcg tgacgctgtc agcgcaagag gcggcgccgc catacatgcg   120
gtgtgacgac atgctcctag tgcagagcac cagcatcacc caagatcttg gtgagatcaa   180
ttatcaagaa ttgttcgacg tggccagggc ggata                              215

<210> SEQ ID NO 12
<211> LENGTH: 215
<212> TYPE: DNA
<213> ORGANISM: Artificial Sequence
<220> FEATURE:
<223> OTHER INFORMATION: Marker Excalibur_c1787_1301S

<400> SEQUENCE: 12
catattgatg aacaagaaca agtatagtgt gcggccaagc caagggacca tgccaccgtg    60
ctccaggcgt tatgttgtcg tgacactgtc agcgcaagag gcggcgccgc catacatgcg   120
gtgtgacgac atgctcctag tgcagagcac cagcatcacc caagatcttg gtgagatcaa   180
ttatcaagaa ttgttcgacg tggccagggc ggata                              215

<210> SEQ ID NO 13
<211> LENGTH: 94
<212> TYPE: DNA
<213> ORGANISM: Artificial Sequence
<220> FEATURE:
<223> OTHER INFORMATION: Marker 1R

<400> SEQUENCE: 13
gtatgaaaag tatgaaaata gcacttgctt gtatgtagac ctacggtttt ctaactatag    60
acttagtaaa cataccacat gaaataacat acca                               94

<210> SEQ ID NO 14
<211> LENGTH: 96
<212> TYPE: DNA
<213> ORGANISM: Artificial Sequence
<220> FEATURE:
<223> OTHER INFORMATION: Marker 1S

```
<400> SEQUENCE: 14
tatcaaaagt atgaaaatag cacttgcttg tatgtagacc tacggtttac taactataga    60
cttagtaata aacataccac atgaaataac atacca                              96

<210> SEQ ID NO 15
<211> LENGTH: 176
<212> TYPE: DNA
<213> ORGANISM: Artificial Sequence
<220> FEATURE:
<223> OTHER INFORMATION: Marker 2R

<400> SEQUENCE: 15
tgctcaacag ctcaagtacc ttttatcctt tagatgctcg gtgaggtcgt gaatgagctc    60
gtgcacctca ttagcgacgg gtggttgatc cggacgaact tgtgcgagta tgctcctcag   120
gatcctcctc atgtcaggtt tcttggcggt ccgcacgaaa gcccggcagc agaagt       176

<210> SEQ ID NO 16
<211> LENGTH: 160
<212> TYPE: DNA
<213> ORGANISM: Artificial Sequence
<220> FEATURE:
<223> OTHER INFORMATION: Marker 2S

<400> SEQUENCE: 16 tacctttat ccttcagatg ctcggtgagg tcatgaatga ggtcgtgcac ctcattagcg     60
tcgggtggtt ggtgcggacg aacttgtgcg agtatgctcc tcaggatcct cctcatgtca   120
ggtttcttgg ccgtccgcac aaaagctcgg cagtcgaagt                         160

<210> SEQ ID NO 17
<211> LENGTH: 176
<212> TYPE: DNA
<213> ORGANISM: Artificial Sequence
<220> FEATURE:
<223> OTHER INFORMATION: Marker 3R

<400> SEQUENCE: 17
tgctcaacag ctcaagtacc ttttatcctt tagatgctcg gtgaggtcgt gaatgagctc    60
gtgcacctca ttagcgacgg gtggttgatc cggacgaact tgtgcgagta tgctcctcag   120
gatcctcctc atgtcaggtt tcttggcggt ccgcacgaaa gcccggcagc agaagt       176

<210> SEQ ID NO 18
<211> LENGTH: 160
<212> TYPE: DNA
<213> ORGANISM: Artificial Sequence
<220> FEATURE:
<223> OTHER INFORMATION: Marker 3S

<400> SEQUENCE: 18 tacctttat ccttcagatg ctcggtgagg tcatgaatga ggtcgtgcac ctcattagcg     60
tcgggtggtt ggtgcggacg aacttgtgcg agtatgctcc tcaggatcct cctcatgtca   120
ggtttcttgg ccgtccgcac aaaagctcgg cagtcgaagt                         160

<210> SEQ ID NO 19
<211> LENGTH: 176
<212> TYPE: DNA
<213> ORGANISM: Artificial Sequence
<220> FEATURE:
<223> OTHER INFORMATION: Marker 4R

<400> SEQUENCE: 19
```

```
tgctcaacag ctcaagtacc ttttatcctt tagatgctcg gtgaggtcgt gaatgagctc    60
gtgcacctca ttagcgacgg gtggttgatc cggacgaact tgtgcgagta tgctcctcag   120
gatcctcctc atgtcaggtt tcttggcggt ccgcacgaaa gcccggcagc agaagt       176

<210> SEQ ID NO 20
<211> LENGTH: 160
<212> TYPE: DNA
<213> ORGANISM: Artificial Sequence
<220> FEATURE:
<223> OTHER INFORMATION: Marker 4S

<400> SEQUENCE: 20 tacctttat ccttcagatg ctcggtgagg tcatgaatga ggtcgtgcac ctcattagcg     60
tcgggtggtt ggtgcggacg aacttgtgcg agtatgctcc tcaggatcct cctcatgtca   120
ggtttcttgg ccgtccgcac aaaagctcgg cagtcgaagt                         160

<210> SEQ ID NO 21
<211> LENGTH: 144
<212> TYPE: DNA
<213> ORGANISM: Artificial Sequence
<220> FEATURE:
<223> OTHER INFORMATION: Marker 5R

<400> SEQUENCE: 21
ccaagtgtta gtatactcta ggaagcttta tgcgccaact ttgcatgtag gtaactaaaa    60
actgggtgaa aaggttgctg acagagcctg gatattcctc gcacgaaacc gacatgctag   120
gagtcactag atgtgttgaa attg                                          144

<210> SEQ ID NO 22
<211> LENGTH: 144
<212> TYPE: DNA
<213> ORGANISM: Artificial Sequence
<220> FEATURE:
<223> OTHER INFORMATION: Marker 5S

<400> SEQUENCE: 22
ccaagtgtta gtatactcta ggaagcttta tgcgccaact ttgcatgtag gtaactaaaa    60
actgggcgaa aaggttgctg acagagcctg gatattcctc gcacgaaacc gacatgctag   120
gagtcactag atgtgttgaa attg                                          144

<210> SEQ ID NO 23
<211> LENGTH: 16
<212> TYPE: DNA
<213> ORGANISM: Artificial Sequence
<220> FEATURE:
<223> OTHER INFORMATION: NBS1 8000 Primer F

<400> SEQUENCE: 23
cgacggcgca cgtgat                                                    16

<210> SEQ ID NO 24
<211> LENGTH: 20
<212> TYPE: DNA
<213> ORGANISM: Artificial Sequence
<220> FEATURE:
<223> OTHER INFORMATION: NBS1 8000 Primer R

<400> SEQUENCE: 24
aacggacgac gaatgcaaat                                                20
```

<210> SEQ ID NO 25
<211> LENGTH: 16
<212> TYPE: DNA
<213> ORGANISM: Artificial Sequence
<220> FEATURE:
<223> OTHER INFORMATION: NBS1 8000 Probe MGB

<400> SEQUENCE: 25
tggactcgat ccattg                                           16

<210> SEQ ID NO 26
<211> LENGTH: 55
<212> TYPE: DNA
<213> ORGANISM: Artificial Sequence
<220> FEATURE:
<223> OTHER INFORMATION: NBS1 8000 Amplicon or marker sequence

<400> SEQUENCE: 26
cgacggcgca cgtgatgctg gactcgatcc attgcatttg cattcgtcgt ccgtt    55

<210> SEQ ID NO 27
<211> LENGTH: 19
<212> TYPE: DNA
<213> ORGANISM: Artificial Sequence
<220> FEATURE:
<223> OTHER INFORMATION: NBS4 4000 Primer F

<400> SEQUENCE: 27
acgctccgca aaaatctga                                        19

<210> SEQ ID NO 28
<211> LENGTH: 21
<212> TYPE: DNA
<213> ORGANISM: Artificial Sequence
<220> FEATURE:
<223> OTHER INFORMATION: NBS4 4000 Primer R

<400> SEQUENCE: 28
aacaacgaat agcgccttga g                                     21

<210> SEQ ID NO 29
<211> LENGTH: 15
<212> TYPE: DNA
<213> ORGANISM: Artificial Sequence
<220> FEATURE:
<223> OTHER INFORMATION: NBS4 4000 Probe MGB

<400> SEQUENCE: 29
tgaccgggac gagca                                            15

<210> SEQ ID NO 30
<211> LENGTH: 57
<212> TYPE: DNA
<213> ORGANISM: Artificial Sequence
<220> FEATURE:
<223> OTHER INFORMATION: NBS4 4000 Amplicon or marker sequence

<400> SEQUENCE: 30
acgctccgca aaaatctgat tgaccgggac gagcagctca aggcgctatt cgttgtt    57

<210> SEQ ID NO 31
<211> LENGTH: 3000
<212> TYPE: DNA
<213> ORGANISM: Triticum aestivum

<400> SEQUENCE: 31

```
gtcctacgga ctaaactctc cggtttatat agacatcgga ggaggctagt gagggagtcc      60
tggattaggg ggtatccgga cagccggact gtatacatct tccggtctat tgaagcgtga     120
agatacaaga ctcaagactt cggcccgtgt ccggatggga ctctcctttg tgtggaagac     180
aagcttggcg atccggatat tatatttcct tccttgtaac cgactccatg taaaccttag     240
ccctctccgg tgtctatata aaccggagag gatggttctt agaaggccga tcacagttac     300
aatcatacca tcataggcta gctcctaggg tttagcctct acgatctcgt ggtagatcaa     360
ctcttgtact acacatatct tcaatattaa tcaagcatga agtagggttt tacctcaatc     420
gagagggctc gaacctgagt aaacattgtg tcccttgctt actgttacca tcagcctaag     480
acgcacaaat cgggaccccc tacccgagat ccgccggttt tgacaccgac attggtgctt     540
tcattgagag tttctctgtg tcgtcgcttt gaggcttgat ggcgtcttca atcgccaaca     600
acaccgtcca gggcgagact tttctccccg gacagatctt tgtgttcggc ggcttcgcac     660
tgcgggccaa ttcgcttggt catctggagc agatcgacag ctacgcccct ggccaccaga     720
tcaggttcgg aaacttgaac tacacggcgg atatttgcgg agacttgatc ttcgacggat     780
tcggccctgt gccaggagcg ccggacaatc acgacgagca cggcctagac ctgttgtcgg     840
acaattctca gaacatcatc cctgaaatag ccccggatct aaatccggaa caggttgtgt     900
tgcccaagga cggagggata gaccccgtcc cgcaggccac atactcatcg gcggtggagc     960
cgaacacagg tctcacctct gtggaagcca gtaacccgg ccccccggac tcatatccgg    1020
ttgttggttc cggtctgcac accccgagc cagtcgaacc aggctaggct ccggtaatgg    1080
agcttaccgc tgcggacatc tttcaacact cgcccctttgg cgacatgttg aattcattaa    1140
agtctctctc tttgttagga ggctctgggc cgaactatgt ccggcctgag tgggaagcag    1200
gcgacgaagg aattcgttgc ccacccagca cccacttcat tgccacggtc gacgatttaa    1260
ccgacgtgct taactttgac tccaaagata tcgacggtat ggacgacgat gcaggagacg    1320
tacaggagcc accgctcata gggcggtgga cggccacctc ctcatacgat atatacacgg    1380
tggacactcc gaaggaaacc aatggcgacg aggcagcgga ggataacccc tcgggaggaa    1440
aagcaaaaca tgggcgtctt cggcgtcgct ccaagccccg ccacatcaat accgtccccg    1500
gagatgatcc ggacagtgcc gaagaggaat acagccctga tcaggccacc ttcaagcagg    1560
ccggacaggc cacgttggga tacttggaaa gggacaacta tacagccccc tccaaagatg    1620
aggtaagcct cagcaatgac gaattcggtg tgcctgaaga tccagtggaa cagttcgctt    1680
caagcgacgg ctcatggcca cggcaaggtg cctgcacagg aagcaagagc agcttaaagc    1740
caaccaggat ttgctaatgg acaggtggac caagatcctg gccaccgaaa agtacggact    1800
cgaccacccc agcaaaggc atacgcggca caactggcta cctcaaccta gcaggagaa     1860 ccaaaagcac acaacccgac gtccgcacac cactacggtc caagacagca agaagaatac    1920
atgaagaggc atcctcaagc ctcggcgcaa tggtcataaa cgtcaagtca gggacgctgg    1980
tgccaagtcc agcaactccc agtctgatca acggacaaag agcagctcaa gcctattcgg    2040
cccaagccac aaactcgatc aaccgtgtga attaacggt actcccagaa ggacggcaaa    2100
acataccaat agagaatgcc ggatcttcaa acaaagcgac cggtcgtgtg ccggaaacaa    2160
tgaagggagg cgtctagtca agagaccccc cccagagca caacagtacg gccgatcgcc    2220
cctaccatac aaaccacagc aattaaattt tcgtacccc agacccagta gtccaggggc    2280
tccataacac ataaagcctc cgcgggtatg aatctacaaa taacacccttc tacaaaatgt    2340
```

| | |
|---|---|
| caggtgcaaa ggccaagttc attggcccac cgctctaacg gttgctttca gataaccaaa | 2400 |
| aaatgtcacg tcatcggtgc attccctca tacggtaacc caccgtctgc taacgggatg | 2460 |
| aaccacgttg actagattcc acgtggtaaa ccattaggcc aacaccagtg atatactcac | 2520 |
| gcctacgtac aaggccgaac ccctcccta gagcggaaat catacagctg ccggagtagc | 2580 |
| aagtcatgca tgcctatcaa tattttgata tgacatccaa ctattcggac accaactgag | 2640 |
| gagtccgcgc tgcttctcgg tatatcggct agggtcacca gggtccgatc aggaaccttt | 2700 |
| agcccaactg tcggtgtcaa aaccggcgga tctcgggtag agggtcccga actgtgcgtc | 2760 |
| taggcggatg gtaacaggag acaagggaca cgatgttttt acccaggttc gggccctctc | 2820 |
| gatggaggta aaccctact cctgcttgat taatattgat gatatggata gtacaagagt | 2880 |
| agatctacca cgagatcaga gaggctaaac cctagaagct agcctatgtt atgattgttg | 2940 |
| tttgtcctac ggactaaaac cctccggttt ataggcac cgaatagggt tagggttaca | 3000 |

<210> SEQ ID NO 32
<211> LENGTH: 3000
<212> TYPE: DNA
<213> ORGANISM: Triticum aestivum

<400> SEQUENCE: 32

| | |
|---|---|
| tcttttcatt taattttata tcctttagca gtagcgagtt tagattaaaa cgcgctgcta | 60 |
| caaataaagt accggtagcg cggttcgtta taggtcgcta ctactatgtg tagcctatcg | 120 |
| gctaagccgt gggaattta gtagtaacgt gtttagagca agacgcgcta ctgctagaac | 180 |
| tttatctgca gcgcggtttg ctcaggcgcg ctactgctac ttagcaccag cgtgcttttt | 240 |
| tgaccctcgc tactgctaaa gttctgtgta taaggttttc cctagtagtg ttactacgga | 300 |
| agaccatagc tctcactttc cataaaagtg ttctatctaa aacgtttatg atgaatagct | 360 |
| gcacaaatcc tgctcggcac attttcctt ggcttactgg ggaagctgtc ggtttatata | 420 |
| cggatgttct atctaaaacg tttgcgatca agagctgcac aactcgtcac attttcgcta | 480 |
| ggcttcccgg ggaagctgtt ggtttgcata cgggtgttct aactaaaact tttgcaatga | 540 |
| gtgttttata tttaaaaatt gtattaaact gcggcatggg cgccattaat gtagaggatg | 600 |
| cgagcaaggc ggccggccat ggaagtcaaa gggctcactt cccagtgagc ttgcgcggca | 660 |
| tacagctcac acgctttccg gtgagcctgc acattggagt acagctcgca cacctcccgt | 720 |
| ttagtcaagc acctgtttgc atgacacctc ctagccatta aaagagtgag gcgtgacatc | 780 |
| acgtgaatgg ttaagataac acacgtttt taaattattt aaaatgtttg agatgttaca | 840 |
| gtggcagcaa tttgtttcaa aatgcctttg ttggctgtta tttgagtgcg ccttctctca | 900 |
| aaatggacac aaaaaatacc acaacatgtc gggtgccatt tcatgatagc atgccaagtt | 960 |
| tcatgaattt tcgacgagtt ttggatttac tagaatttaa aaacagagta tttcaacatt | 1020 |
| ttgtcggcaa tcaatagtgc cctggtgttt gaaattcatt ctaatttctt gcatgagact | 1080 |
| taagcatgca cccaaggaca catatttgat tttccaacca atttatatgc actggagcat | 1140 |
| gtgcatgtag ttcaaatttg aattatgcac ataaaatgcc tagaaaaccc agttaatgta | 1200 |
| taaaaatgac caaacgagcc ctattttttt ttcaaaattt aacacaacac tcctgttatt | 1260 |
| ctatgttgac actagaaatt ttttgaaagc aataagaggc aacggatatc attttgtccc | 1320 |
| taaagtggca cgttccctac cgaagacatc aggcttgttg tgagaagctc cggtttgtga | 1380 |
| gaagcttata cccaaacctg ccccaaatgg gacaaaaatt ttaccacggc atgttgatgc | 1440 |
| cgctccatga tagtatgcga agtttcatga atttcagaca agttatggat ttactaaaat | 1500 |

```
ttaaaaacca tgtatctcaa tgtttgcggc cgagtgacga tggcagggtg tttgacatcc    1560
attcccattt cttgcatggg acctaagcat gcaaccaatg acacatattt gaattttcaa    1620
ccaatttata tgcactaaag catgtgcctg tagttcaaat ttgtgagaac gttaacgtca    1680
ttgtgagaac ccgacattcc aaaaaaagca tgccaaatct ataagtcatg tgatgccgct    1740
gcttctatag tatgatggtg gcctctttga tgtgccctcg atacattctc cgcaaagcct    1800
tgtggcagtt cttccattgc caatgcatgc aatcaattga tgcgagcatc catgaaaatt    1860
ctcaggcctc tcaagtagcc aacaactcct ctctgtcgtg tgcatttggt tctctcagat    1920
actctgctcc aaacacctgc accatggcac gggcaaactt gacagtagtc ttcaggcatg    1980
cgctctcccc catactgaca atctcaccaa tgagagtacc tagtgtaagc atcctcagag    2040
cagctgcgca cttctgttta gcagagaaag aaagttggct gcaacaatcc ctcgtgagct    2100
tgaagtagtc atcatgtgcc ttcattccct ccattatgcg caaaacaatg gttttcgcat    2160
gcgaaaaccg cgaagaaacc atggatcatc taggaaagtt ggatttcgag caaagtagtc    2220
cttctgtagt aggcatgctc cggactccct gcccgattga ccactcttct ccctttgatt    2280
gagtccttga agttgagaat atgctccact tgccggtcca tttcttcttg catgctcatc    2340
ggcatgatca tgtccacttc ttctccgaat acgaggaatc gaagaactca tcttgaacca    2400
tttgatcaag cttcgtcggt ccatactcgg tgtgcgacga agcatcagga tccattgttt    2460
tctctataaa aatcacaaaa aaaactaggt tgaggaatgt gtcgaacaca tagagtgtaa    2520
ggggtgcctg ggagttgcca gacgtaccgc ggtggcgtcc ggactggcga tgacatcccc    2580
gtcagcgagg atagaaggga ggagtgttgt gccagttctg gaggcgcaga ggctctaaac    2640
agcggtggat ctgcgagacg gacatcgtga aggaggaaga agagataaga gaccaaatga    2700
atccggtagg tcaaggggat ggatttggtg caatttgagt taggataaag ctgtcgggtc    2760
tgacatggca gatgcgcctg gacgcgccca tatctgcccc atatttgggc aacatatgag    2820
gggtgtcggt cagtcggggc ggttgagacc gtttgaggtg cccgtctgag tcggattttg    2880
gtgaccgatc aataaccatg ccgttcgctc ggtcgtttaa ggtgggtttg aacgtccag    2940 ctgcagatgc tcttatatga atttaggtgc gggaatatga cgagtactat tattgcggac    3000
```

<210> SEQ ID NO 33
<211> LENGTH: 2750
<212> TYPE: DNA
<213> ORGANISM: Triticum aestivum

<400> SEQUENCE: 33

```
tgtctatata aaccggagag gatggttctt agaaggccga tcacagttac aatcatacca     60
tcataggcta gctcctaggg tttagcctct acgatctcgt ggtagatcaa ctcttgtact    120
acacatatct tcaatattaa tcaagcatga agtagggttt tacctcaatc gagagggctc    180
gaacctgagt aaacattgtg tcccttgctt actgttacca tcagcctaag acgcacaaat    240
cgggaccccc tacccgagat ccgccggttt tgacaccgac attggtgctt tcattgagag    300
tttctctgtg tcgtcgcttt gaggcttgat ggcgtcttca atcgccaaca acaccgtcca    360
gggcgagact tttctccccg acagatcttt gtgttcggc ggcttcgcac tgcgggccaa    420
ttcgcttggt catctggagc agatcgacag ctacgcccct ggccaccaga tcaggttcgg    480
aaacttgaac tacacggcgg atatttgcgg agacttgatc ttcgacggat tcggccctgt    540
gccaggagcg ccggacaatc acgacgagca cggcctagac ctgttgtcgg acaattctca    600
```

```
gaacatcatc cctgaaatag ccccggatct aaatccggaa caggttgtgt tgcccaagga    660
cggagggata gaccccgtcc cgcaggccac atactcatcg gcggtggagc cgaacacagg    720
tctcacctct gtggaagcca gtaaccccgg ccccccggac tcatatccgg ttgttggttc    780
cggtctgcac accccgagc cagtcgaacc aggctaggct ccggtaatgg agcttaccgc    840
tgccggacatc tttcaacact cgcccctttgg cgacatgttg aattcattaa agtctctctc    900
tttgttagga ggctctgggc cgaactatgt ccggcctgag tgggaagcag gcgacgaagg    960
aattcgttgc ccacccagca cccacttcat tgccacggtc gacgatttaa ccgacgtgct   1020
taactttgac tccaaagata tcgacggtat ggacgacgat gcaggagacg tacaggagcc   1080
accgctcata gggcggtgga cggccacctc ctcatacgat atatacacgg tggacactcc   1140
gaaggaaacc aatggcgacg aggcagcgga ggataacccc tcgggaggaa aagcaaaaca   1200
tgggcgtctt cggcgtcgct ccaagccccg ccacatcaat accgtccccg gagatgatcc   1260
ggacagtgcc gaagaggaat acagcccctga tcaggccacc ttcaagcagg ccggacaggc   1320
cacgttggga tacttggaaa gggacaacta tacagccccc tccaaagatg aggtaagcct   1380
cagcaatgac gaattcggtg tgcctgaaga tccagtggaa cagttcgctt caagcgacgg   1440
ctcatggcca cggcaaggtg cctgcacagg aagcaagagc agcttaaagc caaccaggat   1500
ttgctaatgg acaggtggac caagatcctg gccaccgaaa agtacggact cgaccacccc   1560
agcaaagggc atacgcggca caactggcta cctcaaccta agcaggagaa ccaaaagcac   1620
acaacccgac gtccgcacac cactacggtc caagacagca agaagaatac atgaagaggc   1680
atcctcaagc ctcggcgcaa tggtcataaa cgtcaagtca gggacgctgg tgccaagtcc   1740
agcaactccc agtctgatca acggacaaag agcagctcaa gcctattcgg cccaagccac   1800
aaactcgatc aaccgtgtga aattaacggt actcccagaa ggacggcaaa acataccaat   1860
agagaatgcc ggatcttcaa acaaagcgac cggtcgtgtg ccggaaacaa tgaagggagg   1920
cgtctagtca agagaccccc ccccagagca caacagtacg gccgatcgcc cctaccatac   1980
aaaccacagc aattaaattt tcgtaccccc agacccagta gtccagggc tccataacac   2040
ataaagcctc cgcgggtatg aatctacaaa taacaccttc tacaaaatgt caggtgcaaa   2100
ggccaagttc attggcccac cgctctaacg gttgcttttca gataaccaaa aaatgtcacg   2160
tcatcggtgc attcccctca tacggtaacc caccgtctgc taacgggatg aaccacgttg   2220
actagattcc acgtggtaaa ccattaggcc aacaccagtg atatactcac gcctacgtac   2280
aaggccgaac ccctccccta gagcggaaat catacagctg ccggagtagc aagtcatgca   2340
tgcctatcaa tattttgata tgacatccaa ctattcggac accaactgag gagtccgcgc   2400
tgcttctcgg tatatcggct agggtcacca gggtccgatc aggaaccttt agcccaactg   2460
tcggtgtcaa aaccggcgga tctcgggtag agggtcccga actgtgcgtc taggcggatg   2520
gtaacaggag acaagggaca cgatgttttt acccaggttc gggccctctc gatggaggta   2580
aaaccctact cctgcttgat taatattgat gatatggata gtacaagagt agatctacca   2640
cgagatcaga gaggctaaac cctagaagct agcctatgtt atgattgttg tttgtcctac   2700
ggactaaaac cctccggttt atataggcac cgaataggg tagggttaca   2750
```

<210> SEQ ID NO 34
<211> LENGTH: 1637
<212> TYPE: DNA
<213> ORGANISM: Triticum aestivum

<400> SEQUENCE: 34

```
atacgatata tacacggtgg acactccgaa ggaaaccaat ggcgacgagg cagcggagga    60
taacccctcg ggaggaaaag caaaacatgg gcgtcttcgg cgtcgctcca agccccgcca   120
catcaatacc gtccccggag atgatccgga cagtgccgaa gaggaataca gccctgatca   180
ggccaccttc aagcaggccg acaggccac gttgggatac ttggaaaggg acaactatac   240
agcccctcc aaagatgagg taagcctcag caatgacgaa ttcggtgtgc ctgaagatcc   300
agtggaacag ttcgcttcaa gcgacggctc atggccacgg caaggtgcct gcacaggaag   360
caagagcagc ttaaagccaa ccaggatttg ctaatggaca ggtggaccaa gatcctggcc   420
accgaaaagt acggactcga ccaccccagc aaagggcata cgcggcacaa ctggctacct   480
caacctaagc aggagaacca aaagcacaca acccgacgtc cgcacaccac tacggtccaa   540
gacagcaaga agaatacatg aagaggcatc ctcaagcctc ggcgcaatgg tcataaacgt   600
caagtcaggg acgctggtgc caagtccagc aactcccagt ctgatcaacg acaaagagc   660
agctcaagcc tattcggccc aagccacaaa ctcgatcaac cgtgtgaaat taacggtact   720
cccagaagga cggcaaaaca taccaataga gaatgccgga tcttcaaaca aagcgaccgg   780
tcgtgtgccg gaaacaatga agggaggcgt ctagtcaaga accccccccc cagagcacaa   840
cagtacggcc gatcgcccct accatacaaa ccacagcaat taaattttcg taccccccaga  900
cccagtagtc caggggctcc ataacacata aagcctccgc gggtatgaat ctacaaataa   960
caccttctac aaaatgtcag gtgcaaaggc caagttcatt ggcccaccgc tctaacggtt  1020
gctttcagat aaccaaaaaa tgtcacgtca tcggtgcatt cccctcatac ggtaacccac  1080
cgtctgctaa cgggatgaac cacgttgact agattccacg tggtaaacca ttaggccaac  1140
accagtgata tactcacgcc tacgtacaag gccgaacccc tcccctagag cggaaatcat  1200
acagctgccg gagtagcaag tcatgcatgc ctatcaatat tttgatatga catccaacta  1260
ttcggacacc aactgaggag tccgcgctgc ttctcggtat atcggctagg gtcaccaggg  1320
tccgatcagg aacctttagc ccaactgtcg gtgtcaaaac cggcggatct cgggtagagg  1380
gtcccgaact gtgcgtctag gcggatggta acaggagaca agggacacga tgttttttacc  1440
caggttcggg ccctctcgat ggaggtaaaa ccctactcct gcttgattaa tattgatgat  1500
atggatagta caagagtaga tctaccacga gatcagagag gctaaaccct agaagctagc  1560
ctatgttatg attgttgttt gtcctacgga ctaaaaccct ccggtttata taggcaccga  1620
atagggttag ggttaca                                                  1637

<210> SEQ ID NO 35
<211> LENGTH: 410
<212> TYPE: DNA
<213> ORGANISM: Triticum aestivum

<400> SEQUENCE: 35
tgcctatcaa tattttgata tgacatccaa ctattcggac caactgagag gagtccgcgc    60
tgcttctcgg tatatcggct agggtcacca gggtccgatc aggaaccttt agcccaactg   120
tcggtgtcaa aaccggcgga tctcgggtag agggtcccga actgtgcgtc taggcggatg   180
gtaacaggag acaagggaca cgatgttttt acccaggttc gggccctctc gatggaggta   240
aaaccctact cctgcttgat taatattgat gatatggata gtacaagagt agatctacca   300
cgagatcaga gaggctaaac cctagaagct agcctatgtt atgattgttg tttgtcctac   360
ggactaaaac cctccggttt atataggcac cgaatagggt tagggttaca               410
```

<210> SEQ ID NO 36
<211> LENGTH: 2094
<212> TYPE: DNA
<213> ORGANISM: Triticum aestivum

<400> SEQUENCE: 36

| | | | | | |
|---|---|---|---|---|---|
| acacaaaaaa | taccacaaca | tgtcgggtgc | catttcatga | tagcatgcca | agtttcatga | 60 |
| attttcgacg | agttttggat | ttactagaat | ttaaaaacag | agtatttcaa | cattttgtcg | 120 |
| gcaatcaata | gtgccctggt | gtttgaaatt | cattctaatt | tcttgcatga | gacttaagca | 180 |
| tgcacccaag | gacacatatt | tgattttcca | accaatttat | atgcactgga | gcatgtgcat | 240 |
| gtagttcaaa | tttgaattat | gcacataaaa | tgcctagaaa | acccagttaa | tgtataaaaa | 300 |
| tgaccaaacg | agccctattt | ttttttcaaa | atttaacaca | acactcctgt | tattctatgt | 360 |
| tgacactaga | aatttttga | aagcaataag | aggcaacgga | tatcattttg | tccctaaagt | 420 |
| ggcacgttcc | ctaccgaaga | catcaggctt | gttgtgagaa | gctccggttt | gtgagaagct | 480 |
| tatacccaaa | cctgcccccaa | atgggacaaa | aattttacca | cggcatgttg | atgccgctcc | 540 |
| atgatagtat | gcgaagtttc | atgaatttca | gacaagttat | ggatttacta | aaatttaaaa | 600 |
| accatgtatc | tcaatgtttg | cggccgagtg | acgatgcag | ggtgtttgac | atccattccc | 660 |
| atttcttgca | tgggacctaa | gcatgcaacc | aatgacacat | atttgaattt | tcaaccaatt | 720 |
| tatatgcact | aaagcatgtg | cctgtagttc | aaatttgtga | gaacgttaac | gtcattgtga | 780 |
| gaacccgaca | ttccaaaaaa | agcatgccaa | atctataagt | catgtgatgc | cgctgcttct | 840 |
| atagtatgat | ggtggcctct | ttgatgtgcc | ctcgatacat | tctccgcaaa | gccttgtggc | 900 |
| agttcttcca | ttgccaatgc | atgcaatcaa | ttgatgcgag | catccatgga | aattctcagg | 960 |
| cctctcaagt | agccaacaac | tcctctctgt | cgtgtgcatt | tggttctctc | agatactctg | 1020 |
| ctccaaacac | ctgcaccatg | gcacgggcaa | acttgacagt | agtcttcagg | catgcgctct | 1080 |
| cccccatact | gacaatctca | ccaatgagag | tacctagtgt | aagcatcctc | agagcagctg | 1140 |
| cgcacttctg | tttagcagag | aaagaaagtt | ggctgcaaca | atccctcgtg | agcttgaagt | 1200 |
| agtcatcatg | tgccttcatt | ccctccatta | tgcgcaaaac | aatggttttc | gcatgcgaaa | 1260 |
| accgcgaaga | aaccatggat | catctaggaa | agttggattt | cgagcaaagt | agtccttctg | 1320 |
| tagtaggcat | gctccggact | ccctgcccga | ttgaccactc | ttctcccttt | gattgagtcc | 1380 |
| ttgaagttga | gaatatgctc | cacttgccgg | tccatttctt | cttgcatgct | catcggcatg | 1440 |
| atcatgtcca | cttcttctcc | gaatacgagg | aatcgaagaa | ctcatcttga | accatttgat | 1500 |
| caagcttcgt | cggtccatac | tcggtgtgcg | acgaagcatc | aggatccatt | gttttctcta | 1560 |
| taaaaatcac | aaaaaaaact | aggttgagga | atgtgtcgaa | cacatagagt | gtaagggggtg | 1620 |
| cctgggagtt | gccagacgta | ccgcggtggc | gtccggactg | gcgatgacat | ccccgtcagc | 1680 |
| gaggatagaa | gggaggagtg | ttgtgccagt | tctggaggcg | cagaggctct | aaacagcggt | 1740 |
| ggatctgcga | gacggacatc | gtgaaggagg | aagaagagat | aagagaccaa | atgaatccgg | 1800 |
| taggtcaagg | ggatggattt | ggtgcaattt | gagttaggat | aaagctgtcg | ggtctgacat | 1860 |
| ggcagatgcg | cctggacgcg | cccatatctg | ccccatattt | gggcaacata | tgagggtgt | 1920 |
| cggtcagtcg | gggcggttga | gaccgtttga | ggtgcccgtc | tgagtcggat | tttggtgacc | 1980 |
| gatcaataac | catgccgttc | gctcggtcgt | ttaaggtggg | tttggaacgt | ccagctgcag | 2040 |
| atgctcttat | atgaatttag | gtgcgggaat | atgacgagta | ctattattgc | ggac | 2094 |

```
<210> SEQ ID NO 37
<211> LENGTH: 540
<212> TYPE: DNA
<213> ORGANISM: Triticum aestivum

<400> SEQUENCE: 37
tctctataaa aatcacaaaa aaaactaggt tgaggaatgt gtcgaacaca tagagtgtaa        60
ggggtgcctg ggagttgcca gacgtaccgc ggtggcgtcc ggactggcga tgacatcccc       120
gtcagcgagg atagaaggga ggagtgttgt gccagttctg gaggcgcaga ggctctaaac       180
agcggtggat ctgcgagacg gacatcgtga aggaggaaga agagataaga gaccaaatga       240
atccggtagg tcaaggggat ggatttggtg caatttgagt taggataaag ctgtcgggtc       300
tgacatggca gatgcgcctg gacgcgccca tatctgcccc atatttgggc aacatatgag       360
gggtgtcggt cagtcggggc ggttgagacc gtttgaggtg cccgtctgag tcggattttg       420
gtgaccgatc aataaccatg ccgttcgctc ggtcgtttaa ggtgggtttg gaacgtccag       480
ctgcagatgc tcttatatga atttaggtgc gggaatatga cgagtactat tattgcggac       540
```

NUCLEIC ACID ENCODING SM1 RESISTANCE TO ORANGE WHEAT BLOSSOM MIDGE AND METHOD OF USE

BACKGROUND

Economic importance of orange wheat blossom midge

Orange wheat blossom midge (OWBM; *Sitodiplosis mosellana* Géhin) is a serious, economic insect pest of both bread (*Triticum aestivum*) and durum wheats (*Triticum durum*) in all the main temperate cereal-growing regions of the world, including North America, Canada, Europe and Asia (Harris et al, 2003). Apart from *T. aestivum*, OWBM has been shown to oviposit and survive on accessions of sixteen other *Triticum* species (Wise et al, 2001), as well as rye, barley, and a number of wild grasses (Zheng, 1965). The feeding damage caused by the OWBM larvae not only results in significant yield losses through the abortion of flowers, grain deformation and reduced specific weight, but it also makes the grain more vulnerable to fungal infection (Oakley, 1994) and reduces quality by lowering the Hagberg Falling Number (Miller and Halton, 1960). In the United Kingdom, crop losses exceeded £30 million in 1993 (Oakley, 1994) and £60 million in 2004, in spite of spraying more than 500,000 hectares of wheat with insecticides (Oakley et al, 2005). Chavalle et al (2015) demonstrated that the relationship between yield and the number of larvae was logarithmic, suggesting that the reduction in yield was caused either by the damage inflicted by young larvae that died at the start of their development or by the activation of costly resistant reactions in the plant.

Life cycle of OWBM (Anon, 2016)

OWBM larvae over-winter in the soil as cocoons until diapause is broken (70 days of less than 10° C.) and then the activated larvae move towards the soil surface. The larvae pupate once rainfall wets the soil to a depth of 10 mm and the soil temperature rises above 13° C. The duration of the pupal stage varies according to temperature, but typically lasts between 2 to 4 weeks. Increasing temperatures, following rainfall, stimulate the hatch of the adults from pupae. Shortly after emergence, females emit a sexual pheromone that attracts the males, which has been identified as (2S,7S)-2,7-nonanediyl dibutyrate (Gries et al. 2000). After mating at the emergence site, the female midge fly off in search of a host plant. Wheat only becomes infested by OWBM if it is exposed to ovipositing females at the time the heads emerge from the flag leaves until anthesis—about 7 days (Elliot and Mann, 1996).

Females are active at dusk, preferring warm, calm, humid evenings, but they only live for 3 to 7 days. Eggs are laid singly or in small groups (normally 1 to 6 eggs) underneath the glumes, but females tend to lay eggs where others have already oviposited. Pre-anthesis heads receive nine times more eggs than post anthesis heads (Ding and Lamb, 1999) as the female midge are attracted by volatile compounds released from pre-anthesis wheat spikes (Birkett et al. 2004). Eggs hatch after 4 to 7 days and the larvae crawl into the florets and feed on the surface of the developing kernels. The larvae will continue feeding for about 2 to 3 weeks and then, following heavy rainfall, they drop out of the spikes back into the soil to form new cocoons, which can remain viable in the ground for 10 years or more.

Chemical Control of OWBM

Control of OWBM in wheat crops can be achieved by spraying chlorpyrifos (IUPAC name: O,O-diethyl O-3,5,6-trichloropyridin-2-yl phosphorothioate), which is an organophosphorus pesticide acting on the nervous system of insects via the inhibition of acetylcholinesterase. Unfortunately this insecticide only kills the adult midge and eggs, but not the larvae within the wheat florets and so the timing of the spray application is critical. The development of pheromone traps, using (2S,7S)-2,7-nonanediyl dibutyrate, (Bruce et al. 2007) has enabled farmers to readily assess the level of midge infestation within their fields. Midge counts can be used as part of a grower's risk assessment to determine whether or not to spray (uk.dowagro.com/wp-content/uploads/2014/05/Wheat-Blossom-Midge-Risk-Assessment-Chart .pdf); however the use of chlorpyrifos has now been banned in the UK, as of April the $1^{ST}$ 2016 (cereals.ahdb.org.uk/chlorpyrifos). The EU has also recently lowered the maximum residue levels for chlorpyrifos on all food crops (Commission Regulation (EU) 2016/60).

Biological control of OWBM There are a number of natural predators of OWBM, but data is limited on their effectiveness (Doane et al, 2013), apart from the parasitic wasp *Macroglenes penetrans*, which plays an important role in reducing OWBM infestations in Western Canada (Olfert et al, 2009).

Plant Resistance Mechanisms to Insect Pests

Many different mechanisms for increased resistance to insect herbivory have been identified in plants (War et al, 2012), but these generally fall into three categories:

1) Tolerance—a polygenic trait enabling the plant to withstand or recover from insect damage, but it does not adversely affect the growth or survival of the insect 2) Antixenosis—a non-preference reaction of insects to a resistant plant caused by plant morphology (e.g. trichomes) or chemical factors that adversely affect insect behavior, often resulting in delayed acceptance or outright rejection.

3) Antibiosis (90% of all described insect resistances)—a resistant plant adversely affects the life cycle of the insect either through its survival rate, development or fecundity.

Many insect resistance QTL have been genetically mapped in different crop plant species (Smith and Clement, 2012), but to date, only a handful of the underlying genes have been successfully cloned. These include: Mi-1.2 from tomato (Rossi et al, 1998), Bph14 from rice (Du et al, 2009) and Vat from melon (Dogimont et al. 2014), all of which have been identified as coiled coil-nucleotide binding site-leucine rich repeats (CC-NBS-LRRs), also known as CNL or non-TIR NBS-LRR's (Meyers et al, 1999).

Genetic Resistance to OWBM

Antixenosis:

For the female wheat midge, there are at least three points, in its behavioral sequence leading to oviposition, that are subject to deterrence: 1) locating and landing on the plant, 2) accepting the plant and initiating probing and 3) finally initiating the oviposition event itself (Gharalari et al, 2011). Oviposition deterrence has been demonstrated by Lamb et al, (2001, 2002, 2003), but its multi-genic nature and environmentally influenced expression make it difficult to incorporate this type of trait into breeding programs (Gharalari et al. 2009a). It is thought that the female midge uses fine-scale features and surface chemicals, including volatiles, to select oviposition sites on the wheat spike (Gharalari et al. 2011). Volatile compounds produced by deterrent genotypes, or at less preferred growth stages (e.g. post-anthesis), do reduce oviposition on preferred genotypes and may cause the females to lay their eggs further from potential larval feeding sites (Lamb et al. 2003; Gharalari et al, 2011). There are no known morphological traits that account for oviposition preferences, apart from a small effect of inter-spikelet distance (Gharalari et al. 2009b).

Antibiosis:

Wheat defends itself in at least two ways against the feeding larvae, both of which appear to be associated with increased production of phenolic acids in the developing seed coat (Ding et al, 2000):

1) The feeding site is suitable for larvae only at an early stage of seed development (Ding and Lamb, 1999). Ten days post-anthesis all seeds become antibiotic to newly hatched larvae. Consequently wheat midge larvae feed on susceptible, young seeds for 10 to 12 days beginning about the time that pollination occurs (Ding and Lamb, 1999).

2) Some wheat genotypes appear to exhibit a hypersensitive reaction on the seed surface that kills the feeding larvae (Lamb et al. 2000) leaving so-called "wound-plugs". This hypersensitive reaction is rapidly induced by larval feeding (Ding et al. 2000) and decreases the survival of the first larval instar by 99% (Lamb et al. 2000). McKenzie et al (2002) demonstrated that this hypersensitive response was controlled by a single, partially dominant gene, which the authors named Sm1. To date, very few alternative genetic resistances to Sm1 have been genetically mapped. One example, published by Blake et al, (2011), identified a QTL (QSm.mst-1A) in the spring wheat variety Reeder, which reduced OWBM infestation by 42% in near isogenic lines with and without the QTL region.

Sm1 Antibiotic Resistance Locus:

Lamb et al (2015) have shown that the expression of the Sm1 locus can vary between wheat varieties and the authors suggest that this may be related to the rate of production and/or the types of phenolic acids produced at the seed surface once resistance has been induced (Ding et al. 2000). Lamb et al (2015) also noted that the inheritance of Sm1 was independent of other resistance mechanisms such as oviposition deterrence.

Thomas et al (2005) mapped the Sm1 locus to the short-arm of chromosome 2B in wheat and developed a linked, dominant SCAR marker (WM1) for use in marker-assisted selection (MAS). More recently, Kassa et al (2016) have refined the map position of the Sm1 locus and discovered that this genomic region in wheat is inverted when to compared to the rice and Brachypodium genomes. They also speculated that Sm1 might be a traditional resistance gene of the CC-NBS-LRR type, but they were only able identify one candidate resistance gene of the NB-ARC type in *B. distachyon* and none were found in the syntenic region in rice. Kassa et al (2016) also identified two SNP markers (kwm707 and kwm693) that could be used to predict the presence of Sm1 locus in diverse panels of wheat varieties, suggesting a single origin for Sm1; however these markers were not 100% diagnostic.

Therefore there is an urgent need to identify perfect markers for Sm1 via the cloning and sequencing of this locus.

DETAILED DESCRIPTION OF THE INVENTION

Figure 1:
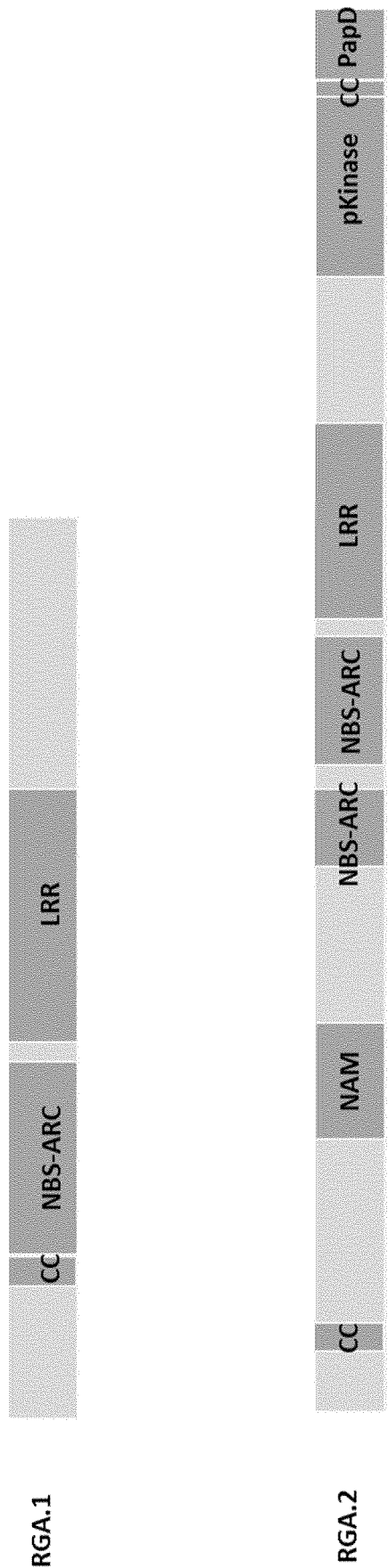
FIG. 1: RGA 1 and RGA 2 representation showing the relative positions of the functional domains identified with InterProScan: (1) Coiled coil; (2) NBS-ARC; (3) LRR; (4) NAM; (5) pKinase; (6) PapD-like (also called Major Sperm Protein (MSP) domain).

The applicant has identified the genetic determinism driving OWBM resistance and is providing different means to improve or newly confer resistance to OWBM in plants. In particular the applicant is providing the nucleic acid encoding for protein correlated with the resistance of the Sm1 locus in wheat and uses of these nucleic acids.

The invention also relates to constructs which can be used as a transgene for obtaining transgenic plants that have improve or newly confer resistance with regards to isogenic plants that do not contain said transgene. The invention also relates to transgenic plants containing such constructs and the method for obtaining such plants.

Finally, markers, methods for introgressing Sm1 resistance locus and method for identifying said locus in plants are also provided.

In the context of the present invention a plant shall mean a monocotyledon and more preferentially a cereal, in particular from *Triticum* species (wheat), maize, rice, barley, sorghum, millet, oats, rye.

Wheat is the preferred cereal according to the invention.

As intended herein, two plants are said to be "isogenic" with regards to a transgene when they differ at very few loci (less than 20, more preferably less than 10), and when one does carry the transgene, while the other does not.

One embodiment of the invention is the nucleic acid encoding for a protein conferring orange wheat blossom midge resistance, wherein the nucleic acid comprises at least one of the group consisting of:
 a) Group 1:
  i. A nucleic acid comprising SEQ ID NO:4 or 5, or
  ii. A nucleic acid encoding an amino acid sequence comprising SEQ ID NO:6, or
  iii. A nucleic acid encoding an amino-acid sequence comprising at least one CC motif, one NBS-ARC motif and one LRR motif and wherein the sequence of the LRR motif is having at least 82% identity with the nucleic acid fragment as depicted in SEQ ID NO:8, or
  iv. A fragment of any of the nucleic acid of i), ii) or iii) or
  v. A nucleic acid fragment of b) iv as depicted in SEQ ID NO: 8, and
 b) Group 2:
  i. A nucleic acid comprising SEQ ID NO:1 or 2, or
  ii. A nucleic acid encoding an amino acid sequence comprising SEQ ID NO:3, or
  iii. A nucleic acid encoding an amino-acid sequence comprising at least one CC motif, one NBS-ARC motif and one LRR motif and wherein the sequence of the LRR motif is having at least 78% identity with the nucleic acid fragment as depicted in SEQ ID NO:7, or
  iv. A fragment of any of the nucleic acid of i), ii) or iii), or
  v. A nucleic acid fragment of a) iv. as depicted in SEQ ID NO: 7

The nucleic acids encoding the Resistance Gene Analogs RGA 1 and RGA 2 are both perfectly correlated to OWBM resistance in plants and more specifically in wheat. Each nucleic acid could be used alone or in combination for improving or conferring a new resistance in a plant.

As disclosed herein, SEQ ID NO:3 provides a wheat RGA 1 protein, SEQ ID NO:1 provides the wheat genomic sequence encoding for RGA 1 and SEQ ID NO:2 provides the wheat coding sequence (from a spliced RNA or a cDNA) encoding for RGA 1.

Similarly, SEQ ID NO:6 provides a wheat RGA 2 protein, SEQ ID NO:4 provides a wheat genomic sequence encoding for RGA 2 and SEQ ID NO:5 provides a wheat coding sequence encoding for RGA 2.

The invention also relates to the protein encoded by the nucleic acid of the invention comprising the group 1 and/or the group 2 as defined above. In a preferred embodiment, the invention relates to the sequences SEQ ID NO: 3 and SEQ ID NO: 6.

Both RGA proteins are comprising CC (coiled-coil), nucleotide-binding site (NBS-ARC) and leucine-rich repeat (LRR) domains, as well as variable amino- and carboxy-terminal domain (Sekhwal et al, 2015). FIG. 1 provides the relative position of these different domains onto RGA 1 and RGA 2 proteins.

Interestingly, RGA 2 protein also comprises a NAM domain, a pkinase domain and a PadD-like domain which could be involved in defense systems in plants.

Different RGAs have been characterized by genome-wide identification and genetic mapping. Hundreds of NBS-LRR containing RGAs have been identified in different plants like *Arabidopsis*, barley, rice, maize and sorghum.

For the characterization of these proteins, many different software packages are publicly available to predict the position of the different motifs (i.e. CC, NBS, LRR and kinase domain) in a polypeptide such as, but not limited to, InterProScan (ebi.ac.uk/interpro/search/sequence-search), MEME (meme-suite-.org, Bailey and Elkan (1994)) or pfam_scan.pl (bit.ly/1M41KRu). Common software used for RGA domain and motif identification are also listed in Sekhwal et al, (2015).

More specifically, the LRR motif of RGA 1 SEQ ID NO: 3 is corresponding to the fragment defined by the amino acid position 599 to the amino acid position 989 while SEQ ID NO:3 is 1435 amino acids long.

The LRR motif of RGA 2 SEQ ID NO: 6 is corresponding to the fragment defined by the amino acid position 1310 to the amino acid position 1615 while SEQ ID NO:6 is 2303 amino acids long.

The invention also encompasses variant nucleic acid sequences encoding for variant proteins of RGA 1 or RGA 2 having one or more deletion/addition or one or more substitution compared to respectively SEQ ID NO:3 or SEQ ID NO: 6 and still possessing the function of improving or conferring a new OWBM resistance. Variant protein of RGA 1 will comprise at least one CC, one NBS-ARC, and one LRR motifs that are encoded by a nucleic acid having at least 78, 79, 80, 85, 90, 95, 96, 97, 98 or 99% identity with the SEQ ID NO:7.

Variant protein of RGA 2 will comprise at least one CC, one NBS-ARC and one LRR-motifs and are encoded by a nucleic acid having at least 82, 83, 84, 85, 90, 95, 96, 97, 98 or 99% identity with SEQ ID NO:8. Variant protein of RGA 2 are further comprising a kinase domain.

Variant nucleic acids is intended to mean natural variants identified in different cultivars or orthologous sequences identified in different species. Variants can also correspond to modifications introduced by mutagenesis in the nucleic acid sequence. These modifications can be made randomly or at specific sites. Different methods are well known to achieve such modification. One method can be based on random mutagenesis such as TILLING (Till et al, 2003), DNA shuffling (Stemmer, 1994) or on a targeted sequence modification provided by double-strand break technologies such as, but not limited to, TALENs (WO2011072246) or CRISPR cas9 (WO2013181440).

The variant nucleic acid can encode a variant protein if the modification at the nucleic acid creates a new codon leading to a new amino acid. It is then possible to screen for modification leading to a protein with altered conformation that promotes a more effective pathogen resistance.

Preferably, using these genome editing tools, it is expected to generate mutants by achieving whole domain modifications, for example via the "domain swapping" method, for further improving the resistance function.

The nucleic acid sequences may be identified from databases, by applying the BLASTN program (especially the BLASTN 2.2.30 program; Altschul et al, 1997; Altschul et al, 2005) preferably to SEQ ID NO: 1, 2, 4 or 5 using the following algorithm parameters:

Expected threshold: 10
Word size: 11
Max matches in a query range: 0
Gap Costs: Existence 5, Extension 2.
No filter for low complexity regions Fragments of the nucleic acid are also disclosed herein. Nucleic acid that are fragments of the invention comprises at least 20, 50, 100, 200, 300, 500 to 1,000 bp of the nucleic acid of the invention.

The nucleic acid can then be used in a construct under an operably linked heterologous promoter, which is also an aspect of the present invention.

As used herein, heterologous promoter means a promoter which does not originate from the same species from which the nucleic acid was derived, or the promoter is from the same species from which the nucleic acid was derived but has been modified to obtain a sequence different from the native sequence.

Operably linked means that there is a functional linkage between the regulatory element (the promoter) and the nucleic acid to allow the expression of the nucleic acid. Both elements can be separated by sequence that can enhance the expression of the nucleic acid like introns.

In a preferred embodiment, in the nucleic acid construct of the invention, the nucleic acid is cloned downstream of a heterologous promoter functional in a plant cell.

A promoter "active in plants" is a promoter that is able to drive expression of a gene operably linked thereto in a plant cell.

For being expressed, a sequence coding for RGA 1 or RGA 2 may be present under the control of a constitutive, tissue specific, developmentally regulated, inducible or meiosis promoter.

Although some promoters may have the same pattern of regulation when there are used in different species, it is often preferable to use monocotyledonous promoters in monocotyledons and dicotyledonous promoters in dicotyledonous plants.

In a preferred embodiment, said construct is under the control of a constitutive promoter.

Examples of constitutive promoters useful for expression include the 35S promoter or the 19S promoter (Kay et al, 1987), the rice actin promoter (McElroy et al, 1990), the pCRV promoter (Depigny-This et al, 1992), the CVMV promoter (Verdaquer et al. 1996), the ubiquitin 1 promoter of maize (Christensen and Quail, 1996), the regulatory sequences of the T-DNA of *Agrobacterium tumefaciens*, including mannopine synthase, nopaline synthase, octopine synthase.

More preferably the promoters used in the invention are those expressed during seed development such as the HMWG promoter (High Molecular Weight Glutenin) of wheat (Anderson and Greene 1989; Roberts et al., 1989), the waxy, zein or bronze promoters of maize, or the promoters disclosed in US 20150007360, US 20120011621, US 20100306876, US 20090307795 or US 20070028327.

Other suitable promoters could be used. It could be an inducible promoter, a developmentally regulated promoted or a tissue-specific promoter such as a leaf-specific promoter, a seed-specific, a BETL specific promoter and the like. Numerous tissue-specific promoters are described in the literature and any one of them can be used. One can cite the promoters disclosed in US 20130024998.

The invention also encompasses a vector containing the nucleic acid construct of the invention.

A vector, such as a plasmid, can thus be used for transforming host cells. The construction of vectors for transformation of host cells is within the capability of one skilled in the art following standard techniques.

The decision as to whether to use a vector for transforming a cell, or which vector to use, is guided by the method of transformation selected, and by the host cell selected.

Where a naked nucleic acid introduction method is used, then the vector can be the minimal nucleic acid necessary to confer the desired phenotype, without the need for additional sequences.

Possible vectors include the Ti plasmid vectors, shuttle vectors designed merely to maximally yield high numbers of copies, episomal vectors containing minimal sequences necessary for ultimate replication once transformation has occurred, transposon vectors, including the possibility of RNA forms of the gene sequences. The selection of vectors and methods to construct them are commonly known to persons of ordinary skill in the art and are described in general technical references (Mullis and Faloona, 1987).

For other transformation methods requiring a vector, the selection of an appropriate vector is relatively simple, as the constraints are minimal. The apparent minimal traits of the vector are that the desired nucleic acid be introduced in a relatively intact state. Thus, any vector which produces a plant carrying the introduced DNA sequence should be sufficient. Also, any vector which introduces a substantially intact RNA which can ultimately be converted into a stably maintained DNA sequence should be acceptable.

For transformation methods within a plant cell, one can cite methods of direct transfer of genes such as direct micro-injection into plant embryos, vacuum infiltration or electroporation, direct precipitation by means of PEG or the bombardment by gun of particles covered with the plasmid DNA of interest.

It is preferred to transform the plant cell with a bacterial strain, in particular *Agrobacterium*, in particular *Agrobacterium tumefaciens*. In particular, it is possible to use the method described by Ishida et al, (1996) for the transformation of Monocotyledons.

However, any additional attached vector sequences which confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenic plants.

The vector can exist, for example, in the form of a phage, a plasmid or a cosmid. The construction of such expression vectors for transformation is well known in the art and uses standard techniques. Mention may be made of the methods described by Sambrook et al. (1989).

For transforming bacteria, a vector is generally defined as being a nucleic acid molecule that possesses elements that allows it to be maintained within said host cell (such as an origin of replication that works in this bacterial host cell).

The invention also encompasses a host cell containing at least the nucleic acid construct of the invention comprising group 1 and/or group 2 as described above.

The decision as to whether to use a given host cell, or which host cell to use, is guided by the method of transformation.

The host cell can be any prokaryotic or eukaryotic cell. Any of a large number of available and well-known host cells may be used in the practice of this invention. The selection of a particular host is dependent upon a number of factors recognized by the art. These include, for example, compatibility with the chosen expression vector, bio-safety and costs. Useful hosts include bacteria such as *E. coli* sp. or *Agrobacterium*. A plant host cell, may be also used, notably a Monocotyledon plant cell, particularly a cereal plant cell, selected in particular from the group consisting of maize, wheat, barley rice, and preferentially wheat.

More particularly, the host cell used in carrying out the invention is *Agrobacterium tumefaciens*, or *Agrobacterium rhizogenes*, according to the method described by Jouanin et al, (1987).

In a specific embodiment, said nucleic acid construct is stably integrated within the genome of said host cell. This embodiment is particularly interesting for plant host cells. Stable integration within the genome means that the expression cassette can be transmitted to the progeny of said host cell upon division.

The invention also encompasses a transgenic plant containing at least one cell containing the nucleic acid construct as defined above, preferably stably integrated within its genome.

A part of such a transgenic plant, in particular fruit, seed, grain or pollen, comprising such a cell or generated from such a cell, is also encompassed by the invention.

It is reminded that a whole plant can be regenerated from a single transformed plant cell. Thus, in a further aspect the present invention provides transgenic plants, or parts of them, including the expression cassette according to the invention. The regeneration can proceed by known methods.

The seeds which grow by fertilization from this plant, also contain this transgene in their genome.

Said plant or part of a plant according to the invention can be a plant or a part of it from various species, notably a Monocotyledons. Said plant is preferably a cereal plant.

Said plant is preferably selected from the group consisting of maize, rice, wheat and barley. In a preferred embodiment, said plant is wheat.

The invention thus relates in particular to a transgenic wheat, containing at least one cell comprising, stably integrated in its genome, the nucleic acid construct of the invention.

In a specific embodiment, said plant, in particular said wheat, comprises multiple cells containing, stably integrated in their genome, the nucleic acid construct of the invention. In this embodiment, it is possible that some cells of said plant do not contain the transgene.

In another embodiment, said transgene comprising the nucleic acid construct of the invention is present in all cells of said plant, in particular said wheat.

In another embodiment, the transgene is introduced within the plant cells such as being expressed transiently, or through a genetic construct not integrated in the genome. Thus, agro-infiltration or any other methods, such as injection or spray, are contemplated for transient expression.

Hybrid plants obtained by crossing plants according to the invention also form part of the invention, when they contain at least one cell containing the expression cassette of the invention.

Any plant as described above can contain one or more transgenes in addition to the cassette according to the invention. One may mention transgenes conferring male sterility, male fertility, resistance to a herbicide (notably glyphosate, glufosinate, imidazolinone, sulfonylurea, L-phosphinotricine, triazine, benzonitrile), resistance to insects (notably a transgene coding for a *Bacillus thuringiensis* toxin), tolerance to water stress. These plants can be obtained by crossing said plants of the invention with other plants containing said transgenes. Alternatively, plants can be co-transformed with an expression cassette containing several different transgenes, including the transgene of the invention.

Transgenic plants comprising an expression cassette according to the invention present an increased or improved resistance to OWBM as compared to control plants corresponding to non-transgenic plants not comprising said expression cassette.

In the present invention resistance to OWBM is measured as follows: plants are grown under field conditions and phenotyped in early summer, once the pheromone traps indicate the presence of midge. Phenotyping is carried out by visual inspection of individual florets on at least 10 spikes from 10 independent plants normally four to five weeks after flowering at the milk stage. A plant is noted as resistant if no midge larvae are present within the spikes. Conversely, a plant is susceptible if at least one larva is observed within the sampled spikes.

The invention also relates to various methods of using the plants of the invention. More particularly the invention relates to a method for conferring or improving resistance to OWBM in a plant, comprising the steps consisting of:
c) transforming at least a plant cell or plant tissue with a vector containing, as a transgene, a nucleic acid construct according to the invention.
d) cultivating the cell(s) or plant tissue thus transformed so as to generate a transgenic plant containing at least a cell which contains, in its genome, at least said nucleic acid construct.
wherein said transgenic plant presents a newly conferred or an improved resistance compared to a plant not comprising said nucleic acid construct.

A method for identifying (i.e. screening for, selecting) a transgenic plant that can be used in a selection (i.e. breeding) process for obtaining a plant with improved or newly conferred resistance, which comprises the step of identifying in a population of plants, the plants containing the nucleic acid construct as described above, is also part of the invention.

Such method is thus an in vitro method, intended to identify, in a population of plants, the ones that carry the transgene according to the invention.

A breeding process for obtaining a plant with improved or newly conferred resistance is performed by known methods in the art, by crossing, back-crossing and stabilizing plants which present an improved or newly conferred resistance.

The method for identifying a plant with improved or newly conferred resistance, which comprises the step of identifying, in a population of plants, the plants containing the nucleic acid construct or transgene as described above, is also part of the invention. Improved or newly conferred resistance is determined after comparison with isogenic plants which do not contain the nucleic acid construct or transgene.

A transgenic plant with a newly conferred resistance is intended to mean a plant which is initially susceptible to OWBM and presents a resistant phenotype after acquiring the transgene by transformation or by a breeding process. A transgenic plant with improved resistance is intended to mean a plant which is initially presenting a resistance to OWBM due to the presence of at least one resistant locus to OWBM and presents a more efficient resistance or a more durable resistance after acquiring the transgene by transformation or by breeding process.

In a specific embodiment, the selection or identification is performed through the use of a marker that is specific to the transgene. In this embodiment, the selection step is thus preferably preceded by a step comprising genotyping said population of plants.

In a specific embodiment, the selection step is preceded by a step comprising extracting the RNA from the individuals in said population.

In a specific embodiment, the selection step is preceded by a step comprising extracting proteins from the individuals in said population.

In a specific embodiment, said population is the progeny obtained from crossing a transgenic plant, wherein said transgene comprises the expression cassette as described above, with a plant line which does not contain said transgene (the recipient plant line).

In a preferred embodiment, the methods are applied to a cereal, in particular, rice, maize, wheat, barley. It is preferred when said plant is wheat.

Figure 2:
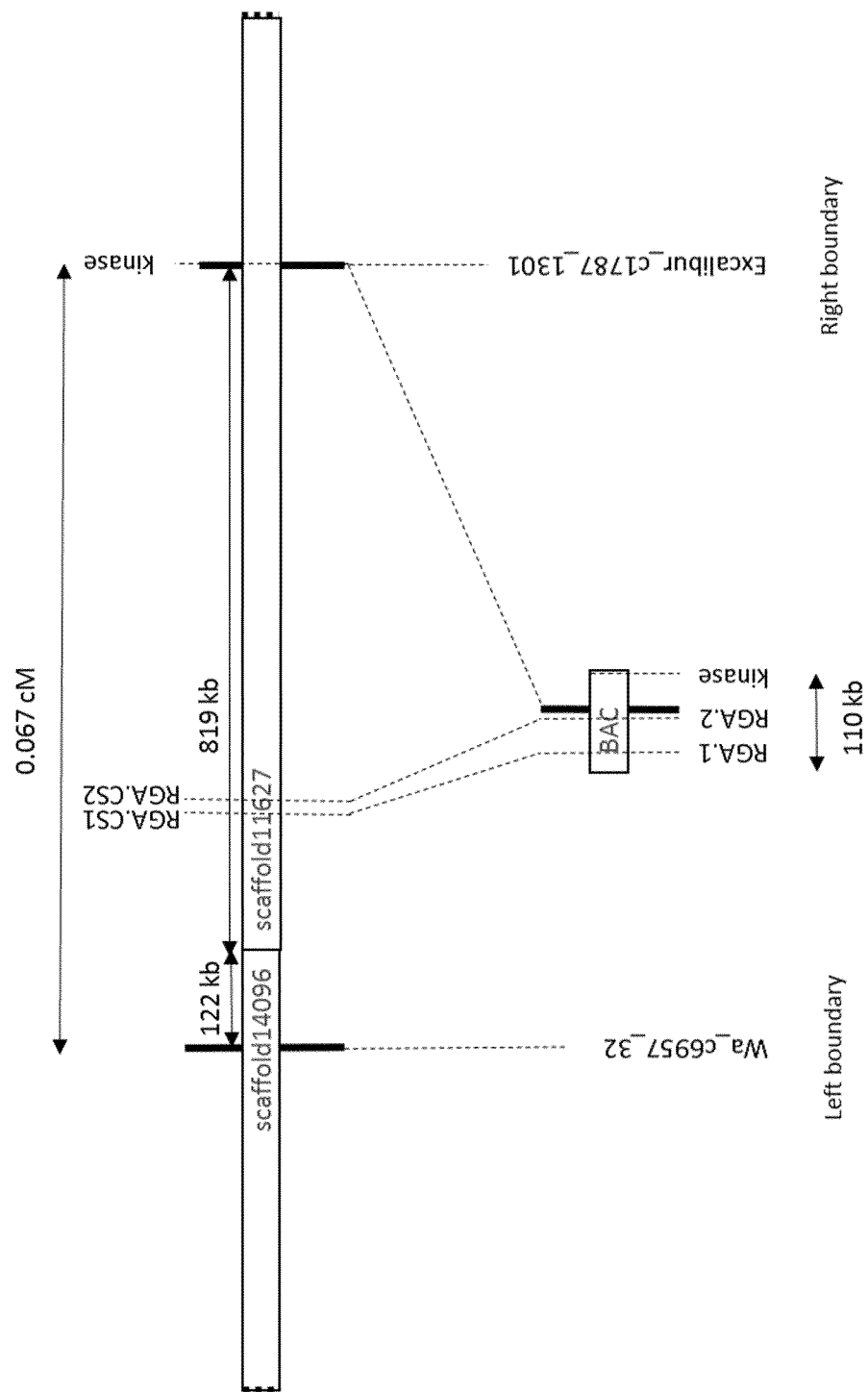
FIG. 2. The physical alignment between BAC 715D09 and the IWGSC WGA scaffolds: IWGSCWGAV02_2BS_scaffold14096 and IWGSCWGAV02_2BS_scaffold11627. RGA.CS refers to the Chinese Spring homologs of the RGA genes annotated in the BAC 715D09.

The invention also encompasses markers used to identify the Sm1 resistance locus in plants. The Sm1 locus is intended to mean a chromosomal region genetically linked to and containing the genes for resistance to OWBM. More specifically, the Sm1 locus comprises the chromosomal interval defined by the SNP markers Wa_c6957_32 and Excalibur_c1787_1301 (FIG. 2). Table 1A and 1B gives details of the DNA sequences used to develop codominant SNP and real-time PCR markers respectively, that were developed by the applicant in the very small genetic interval of 0.067 cM for use in marker-assisted selection for the Sm1 locus.

As used herein a "marker" refers to a specific DNA sequence identified within the genome of a plant and which can be used to determine whether a plant has inherited a particular phenotype or allele of interest from a parent plant.

The marker may include coding or non-coding sequences. In particular, said marker may be a fragment of the genomic sequences SEQ ID NO:1 or SEQ ID NO:4 that allow to detect respectively the presence or absence of the nucleic acid encoding for RGA 1 or the presence of the nucleic acid encoding for RGA 2 in a plant. Said marker may also be a fragment of the respective corresponding coding sequences SEQ ID NO:2 or SEQ ID NO:5.

More specifically the marker used to identify the presence or absence in the genome of a plant of the nucleic acid encoding for RGA 1 is the nucleic acid fragment encoded by the peptide defined by LRR motif of SEQ ID NO:3 said nucleic acid fragment having the sequence as depicted in SEQ ID NO: 7

More specifically the marker used to identify the presence or absence in the genome of a plant of the nucleic acid encoding for RGA 2 is the nucleic acid fragment encoded by the peptide defined by LRR motif of SEQ ID NO:6 said nucleic acid fragment having the sequence as depicted in SEQ ID NO: 8.

In particular the markers of the invention can also be used as a probe to identify and isolate orthologs of genes encoding RGA 1 and RGA 2. Orthologs is intended to mean genes found in different species having a common ancestor and encoding for proteins driving a similar function in the plant that is, in the present invention, resistance to OWBM.

More particularly, the probe to identify and isolate in a plant genome RGA 1 orthologs is depicted in SEQ ID NO:7 and the probe to identify and isolate RGA 2 orthologs is depicted in SEQ ID NO:8.

Any method known in the art may be used in the art to assess the presence or absence of a nucleic acid sequence in the genome of a plant. Some suitable methods include, but are not limited to, sequencing, hybridization assays, polymerase chain reaction (PCR), ligase chain reaction (LCR). Markers of the invention may also include one or more Single Nucleotide Polymorphism or SNP identified between two different susceptible and resistant genomes. It is also possible to identify sequence deletion/insertion (INDEL) polymorphism.

Said marker is preferentially localized within the Sm1 locus comprising both RGA 1 and RGA 2 nucleic acids and bounded by the markers Wa_c6957_32 and Excalibur_c1787 (FIG. 2). More preferentially, it is herein disclosed SNPs within markers (identified by their nucleotide sequence) for determining, in a plant, whether any recombinant chromosomal fragment retains the Sm1 allele conferring OWBM resistance. Table 1 provides the DNA sequences of both the susceptible and the resistant alleles in wheat.

TABLE 1

Marker sequences:

A- Marker showing a single nucleotide polymorphism (SNP) between resistant and susceptible wheat genomes

| Marker sequence of resistance allele | Marker sequence of susceptible allele |
|---|---|
| SEQ ID NO: 9 Marker Wa_c6957_32<br>CGGGACAGCCAAGAGAAATTCCATTTGGCGA[T]CG<br>TTCAAATGTGCACTGCATTCTCGTACTGCCGTCGCC<br>GTCGTCTGTCTCTTGACTGTCG | SEQ ID NO: 10 Marker Wa_c6957_32<br>CGGGACAGCCAAGAGAAATTCCATTTGGCGA[C]CGT<br>TCAAATGTGCACTGCATTCTCGTACTGCCGTCGCCGT<br>CGTCTGTCTCTTGACTGTCG |
| SEQ ID NO: 11 Marker<br>Excalibur_c1787<br>CATATTGATGAACAAGAACAAGTATAGTGTGCGGCC<br>AAGCCAAGGGACCATGCCACCGTGCTCCAGGCGTTA<br>TGTTGTCGTGAC[G]CTGTCAGCGCAAGAGGCGGCG<br>CCGCCATACATGCGGTGTGACGACATGCTCCTAGTG<br>CAGAGCACCAGCATCACCCAAGATCTTGGTGAGATC<br>AATTATCAAGAATTGTTCGACGTGGCCAGGGCGGAT<br>A | SEQ ID NO: 12 Marker<br>Excalibur_c1787_1301<br>CATATTGATGAACAAGAACAAGTATAGTGTGCGGCCA<br>AGCCAAGGGACCATGCCACCGTGCTCCAGGCGTTATG<br>TTGTCGTGAC[A]CTGTCAGCGCAAGAGGCGGCGCCG<br>CCATACATGCGGTGTGACGACATGCTCCTAGTGCAGA<br>GCACCAGCATCACCCAAGATCTTGGTGAGATCAATTA<br>TCAAGAATTGTTCGACGTGGCCAGGGCGGATA |
| SEQ ID NO: 13 Marker 1<br>GTATGAAAAGTATGAAAATAGCACTTGCTTGTATGT<br>AGACCTACGGTTT[T]CTAACTATAGACTTAGTAAA<br>CATACCACATGAAATAACATACCA | SEQ ID NO: 14 Marker 1<br>TATCAAAAGTATGAAAATAGCACTTGCTTGTATGTAG<br>ACCTACGGTTT[A]CTAACTATAGACTTAGTAATAAA<br>CATACCACATGAAATAACATACCA |
| SEQ ID NO: 15 Marker 2<br>TGCTCAACAGCTCAAGTACCTTTTATCCTTTAGATG<br>CTCGGTGAGGTCGTGAATGAG[C]TCGTGCACCTCA<br>TTAGCGACGGGTGGTTGATCCGGACGAACTTGTGCG<br>AGTATGCTCCTCAGGATCCTCCTCATGTCAGGTTTC<br>TTGGCGGTCCGCACGAAAGCCCGGCAGCAGAAGT | SEQ ID NO: 16 Marker 2<br>TACCTTTTATCCTTCAGATGCTCGGTGAGGTCATGAA<br>TGAG[G]TCGTGCACCTCATTAGCGTCGGGTGGTTGG<br>TGCGGACGAACTTGTGCGAGTATGCTCCTCAGGATCC<br>TCCTCATGTCAGGTTTCTTGGCCGTCCGCACAAAAGC<br>TCGGCAGTCGAAGT |
| SEQ ID NO: 17 Marker 3<br>TGCTCAACAGCTCAAGTACCTTTTATCCTTTAGATG<br>CTCGGTGAGGTCGTGAATGAGCTCGTGCACCTCATT<br>AGCGACGGGTGGTTG[A]TCCGGACGAACTTGTGCG<br>AGTATGCTCCTCAGGATCCTCCTCATGTCAGGTTTC<br>TTGGCGGTCCGCACGAAAGCCCGGCAGCAGAAGT | SEQ ID NO: 18 Marker 3<br>TACCTTTTATCCTTCAGATGCTCGGTGAGGTCATGAA<br>TGAGGTCGTGCACCTCATTAGCGTCGGGTGGTTG[G]<br>TGCGGACGAACTTGTGCGAGTATGCTCCTCAGGATCC<br>TCCTCATGTCAGGTTTCTTGGCCGTCCGCACAAAAGC<br>TCGGCAGTCGAAGT |
| SEQ ID NO: 19 Marker 4<br>TGCTCAACAGCTCAAGTACCTTTTATCCTTTAGATG<br>CTCGGTGAGGTCGTGAATGAGCTCGTGCACCTCATT<br>AGCGACGGGTGGTTGAT[C]CGGACGAACTTGTGCG<br>AGTATGCTCCTCAGGATCCTCCTCATGTCAGGTTTC<br>TTGGCGGTCCGCACGAAAGCCCGGCAGCAGAAGT | SEQ ID NO: 20 Marker 4<br>TACCTTTTATCCTTCAGATGCTCGGTGAGGTCATGAA<br>TGAGGTCGTGCACCTCATTAGCGTCGGGTGGTTGGT<br>[G]CGGACGAACTTGTGCGAGTATGCTCCTCAGGATC<br>CTCCTCATGTCAGGTTTCTTGGCCGTCCGCACAAAAG<br>CTCGGCAGTCGAAGT |
| SEQ ID NO: 21 Marker 5<br>CCAAGTGTTAGTATACTCTAGGAAGCTTTATGCGCC<br>AACTTTGCATGTAGGTAACTAAAAACTGGG[T]GAA<br>AAGGTTGCTGACAGAGCCTGGATATTCCTCGCACGA<br>AACCGACATGCTAGGAGTCACTAGATGTGTTGAAAT<br>TG | SEQ ID NO: 22 Marker 5<br>CCAAGTGTTAGTATACTCTAGGAAGCTTTATGCGCCA<br>ACTTTGCATGTAGGTAACTAAAAACTGGG[C]GAAAA<br>GGTTGCTGACAGAGCCTGGATATTCCTCGCACGAAAC<br>CGACATGCTAGGAGTCACTAGATGTGTTGAAATTG |

TABLE 1-continued

Marker sequences:

B- Marker showing a presence or absence in the plant genome (Real-Time PCR marker in the RGA genes)

| | Primer F | Primer R | Probe MGB* | Amplicon or Marker sequence |
|---|---|---|---|---|
| NBS1 8000 | SEQ ID NO: 23 CGACGGCGCACGT GAT | SEQ ID NO: 24 AACGGACGACGAA TGCAAAT | SEQ ID NO: 25 TGGACTCGATCCA TTG | SEQ ID NO: 26 CGACGGCGCACGTGATGC TGGACTCGATCCATTGCA TTTGCATTCGTCGTCCGT T |
| NBS4 4000 | SEQ ID NO: 27 ACGCTCCGCAAAA ATCTGA | SEQ ID NO: 28 AACAACGAATAGC GCCTTGAG | SEQ ID NO: 29 TGACCGGGACGAG CA | SEQ ID NO: 30 ACGCTCCGCAAAAATCTG ATTGACCGGGACGAGCAG CTCAAGGCGCTATTCGTT GTT |

*MGB: Minor Groove Binder

As used herein, the term "allele(s)" means any of one or more alternative forms of a gene at a particular locus. In a diploid (or amphidiploid cell of an organism), alleles of a given gene are located at a specific location or locus on a chromosome. One allele is present on each chromosome of the pair of homologous chromosomes.

Whenever reference to a "plant" or "plants" is made, it is understood that also plant parts (cells, tissues or organs, seed pods, seeds, severed parts such as roots, leaves, flowers, pollen, etc.), progeny of the plants which retain the distinguishing characteristics of the parents. "Plant" also relates to a line, a variety, a cultivar or an elite plant.

The invention relates to a method for identifying a plant resistant to OWBM comprising the Sm1 locus. The method encompasses the identification of a OWBM resistant plant compared to a plant lacking the nucleic acid of the present invention wherein the method is comprising the steps of:
 a) isolating DNA genomic sequence or RNA nucleic acid from the plant, and
 b) identifying the presence of the nucleic acid of the invention or the presence of resistant alleles and/or the absence of susceptible alleles of a marker within the Sm1 locus In a preferred embodiment, the methods are applied to a cereal, in particular, rice, maize, wheat, barley. It is preferred when said plant is wheat.

The presence or absence of the nucleic acid of the invention is identified with a marker or a fragment derived from said nucleic acid. The method can be based on the identification of the presence of either one nucleic acid encoding either RGA 1 or RGA 2, or the presence of both nucleic acid encoding RGA 1 and RGA 2 in a resistant plant. Similarly, the method will be based on the identification of the absence of the such nucleic acids in the susceptible plant.

Markers of interest within the Sm1 locus according to the present invention, defined by the SNPs Wa_c6957_32 and Excalibur c1787 (FIG. 2), are linked to Sm1 resistance. The expression "markers linked to Sm1 resistance" means markers showing a DNA polymorphism between a resistant plant and a susceptible plant or markers amplifying a DNA region from the resistant plant, which is absent in the susceptible plant. Preferentially the markers within the Sm1 locus are the markers as listed in Table 1. More preferentially, the markers of interest are the codominant markers listed in Table 1A. Codominant markers are more informative, as they can detect heterozygous plants which have inherited both a resistant and susceptible allele and more accurate, as a failed PCR amplification of the marker would not be interpreted as being susceptible as could be the case for a dominant marker targeting the resistance allele.

Any method known in the art may be used in the art to assess the presence or absence of a SNP. Some suitable methods include, but are not limited to, sequencing, hybridization assays, polymerase chain reaction (PCR), ligase chain reaction (LCR), and genotyping-by-sequence (GBS), or combinations thereof.

Different PCR-based methods are available to the person skilled of the art. One can use the Real-Time PCR method or the KASP method from KBioscience (LGC Group, Teddington, Middlesex, UK).

Successive rounds of PCR amplification are performed to amplify the target sequence (marker) using fluorescently labelled primers. The nature of the emitted fluorescence is used to identify the allelic form or forms (as in the case of a heterozygote) present in the mix from the studied DNA.

As used herein, a primer encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form though single-stranded form is preferred. Alternatively, nucleic acid probe can be used. Nucleic acid probe encompasses any nucleic acid of at least 30 nucleotides and which can specifically hybridize under standard stringent conditions with a defined nucleic acid. Standard stringent conditions as used herein refers to conditions for hybridization described for example in Sambrook et al. (1989) which can comprise 1) immobilizing plant genomic DNA fragments or library DNA on a filter 2) pre-hybridizing the filter for 1 to 2 hours at 65° C. in 6×SSC 5×Denhardt's reagent, 0.5% SDS and 20 mg/ml denatured carrier DNA 3) adding the probe (labeled) 4) incubating for 16 to 24 hours 5) washing the filter once for 30 min at 68° C. in 6×SSC, 0.1% SDS 6) washing the filter three times (two times for 30 min in 30 ml and once for 10 min in 500 ml) at 68° C. in 2×SSC 0.1% SDS.

The invention also encompasses a method for introgressing the Sm1 resistance into a plant, the method comprising the steps of:
 a) crossing a first resistant plant comprising the nucleic acid of the invention or a resistant allele as listed in Table 1 with a second plant wherein said second plant is not comprising the nucleic acid of the invention or a resistant allele as listed in Table 1 b) backcrossing the progeny of step a) with said second plant c) identifying and selecting from b) one or more plants comprising the nucleic acid of the invention or a resistant allele as listed in Table 1 associated with OWBM resistance.

As used herein, the term "introgression" refers to a DNA fragment of a particular plant transferred into a second plant. More specifically, in a first purpose said second plant is a susceptible plant to OWBM. Introgression allows the production of a new resistant plant from a susceptible one by transferring from a resistant plant a chromosomal fragment comprising the nucleic acid of the invention to a susceptible plant. The transfer of said nucleic acid is identified with the markers of the present invention.

In a second purpose, said second plant is resistant to OWBM due to the presence in its genome of at least one resistance locus different from Sm1 locus. The introgression of Sm1 locus in said second plant allows the combination of Sm1 locus with other resistance loci to OWBM. This process is well-known as "gene pyramiding" or 'gene stacking". In the case of resistance genes, the stacking improves the resistance by providing a plant with increased durability of resistance when compared to a plant having only one resistance locus.

In a preferred embodiment, the methods are applied to a cereal, in particular, rice, maize, wheat, barley. It is preferred when said plant is wheat.

The invention also relates to the use of the nucleic acid of the invention or any fragment of said nucleic acid as a screening tool for identifying a new ligand peptide interacting with the protein encoded by nucleic acid of the invention.

Methods of the art are well known for the identification of ligand-protein interaction like, for example, the yeast two-hybrid system (Fields and Song, 1989) or by immunoprecipitation.

The invention is also encompassing a method for modifying the nucleic acid of the invention to improve the function of the protein encoded by said nucleic acid in order to improve the resistance to OWBM.

Method of the art related to the modification of the genomic DNA or “gene editing” are well-known like, for example TALENs (WO2011072246) or CRISPR Cas9 (WO2013181440).

The present invention also provides the promoter regions of the genes encoding the proteins conferring resistance to OWBM according to the present invention and encompasses a sequence with at least 80%, preferably with at least 85%, more preferably with at least 90%, and even more preferably with at least 95% sequence identity with the sequence of these promoter regions. The identity percentage is calculated by any sequence analysis method known by the skilled person, and particularly with algorithms such as Needleman-Wunsch. The identity percentage is calculated over the whole length of the query sequence.

In a preferred embodiment, the sequences SEQ ID NO: 31 or SEQ ID NO: 32 or any sequence with at least 80%, preferably with at least 85%, more preferably with at least 90%, and even more preferably with at least 95% sequence identity with SEQ ID NO: 31 or SEQ ID NO: 32 comprises the promoter region of the gene encoding a protein conferring resistance to OWBM according to the invention. In an advantageous embodiment of the present invention, the sequences SEQ ID NO: 33 to SEQ ID NO: 37 or any sequence with at least 80%, preferably with at least 85%, more preferably with at least 90%, and even more preferably with at least 95% sequence identity with SEQ ID NO: 33 to SEQ ID NO: 37 comprises the promoter region of the gene encoding a protein conferring resistance to OWBM according to the invention.

EXAMPLES

Example 1. Fine-Mapping of the Genomic Region Containing the Sm1 Locus

A: Fine-Mapping Based on Genetic Linkage Maps:

The Sm1 gene for resistance to Orange Wheat Blossom Midge (OWBM) was first mapped to the short arm of chromosome 2B by Thomas et al (2005) using SSR markers and its map position has recently been refined by Kassa et al (2016). However, the populations used for the linkage mapping were relatively small and so the resolution of these genetic maps is not very high. As a consequence the inventors had to develop a large F2 population and additional DNA markers to saturate the region in order to screen for new recombination events. A total of 259 new SNPs have been developed for the analysis of recombinant plants, as described below, in order to fine map the region of interest and to identify the genes at the Sm1 resistance locus.

In 2011, 4,466 F2 plants were generated from selfing an F1 cross made between the UK winter wheat varieties Xi19 (susceptible) and Robigus (Sm1 resistant). These individuals were genotyped with eight SNP markers that were evenly distributed between 12.3 cM and 41.3 cM on the genetic map of chromosome 2B to identify recombinants across this region. A subset of 376 lines were further genotyped with an additional set of 42 SNP markers in order to produce a more detailed genetic map of the region around the Sm1 locus.

Following two additional rounds of selfing of the recombinant F2 plants with marker selection, a total of 111 F4 homozygous recombinants were generated across the Sm1 region on 2BS. These F4 recombinants were genotyped with the additional 42 SNP markers described above and phenotyped in during the summer of 2013 for resistance to OWBM under field conditions. Phenotyping was carried out, four to five weeks after flowering at the milk stage (Kassa et el, 2016; Ellis et al, 2009), by visual inspection of individual florets on at least 10 spikes from 10 independent plants per F4 family. F4 families with a complete absence of midge larvae within the spikes were scored as being resistant; whereas if a single larvae was found then the whole F4 family was scored as being susceptible. Midge infestation levels were good and the Sm1 locus was mapped, without any ambiguity, to a genetic interval of 0.49 cM (defined by 22 recombinants out of the 4466 F2 plants).

By mining the available in-house and public genomic resources, an extra 186 SNPs were identified within or closely flanking this 0.49 cM interval. These extra markers allowed further discrimination of the 22 recombinant plants and reduced the genetic interval containing Sm1 to just 0.067 cM. Further analysis of the physical map (see Example 1: B) and sequences from the transcriptomics experiment (see Example 3) added 23 extra SNPs to the region which gave a total of 259 markers tightly-linked to the Sm1 locus.

B: Fine-Mapping Based on Physical Maps:

Both the IWGSC chromosome survey contigs (The International Wheat Genome Sequencing Consortium (IWGSC) (2014)) and the IWGSC Whole genome assembly, ‘IWGSC WGA’ (available from June 2016 from the URGI IWGSC repository) were used as the genomic resources to enable the physical mapping of the Sm1 locus.

The right border of the Sm1 interval was anchored to the IWGS contig 2BS:5245756 (11643 bp) with 21 SNP markers on this contig. Three SNP markers (e.g. Excalibur_c1787_1301 depicted in SEQ ID NO:120) confirmed the recombination breakpoint on the IWGS contig 2BS: 5245756. The left border was anchored to the IWGS contig 2BS:5191992 (937 bp) by a single SNP (i.e. Wa_c6957_32 depicted in SEQ ID NO:9).

Following the release of the 'IWGSC WGA' wheat genomic sequence, a total of 93 SNP markers were anchored, to the region of interest, on two scaffolds: IWGS-CWGAV02_2BS_scaffold14096 and IWGSCWGAV02_2BS_scaffold11627 that are 675,277 bp and 2,720,717 bp in length respectively. The genetic order of 93 SNP markers in the Xi19 x Robigus bi-parental mapping population was consistent with the physical position of the SNPs in the 'IWGSC WGA' scaffolds. The SNP markers Wa_c6957_32 and Excalibur_c1787_1301 delimit the borders of the Sm1 interval (FIG. 2) and define a region of 941,325 bp on the 'IWGSC WGA' Chinese Spring genome (122,033 bp on IWGSCWGAV02_2BS_scaffold14096 and 819,292 bp on IWGSCWGAV02_2BS_scaffold11627; FIG. 2).

In parallel, a Renan BAC library, available at the INRA GNRG Plant Genomic Center (cnrgv.Toulouse.inra.fr/), was also screened. Renan is a midge resistant, French winter wheat variety, which is identical to Robigus at the Sm1 locus, as determined by genotyping both varieties with the 21 SNPs developed within the interval defined by Wa_c6957_32 and Excalibur_c1787_1301. The BAC library was screened with four SNP markers located on the 2BS:5245756 contig, plus one SNP from each of the five IWGSC contigs in the vicinity of 2BS:5245756 (i.e. 2BS: 5157057, 2BS:5163033, 2BS:5191992, 2BS:5174837 and 2BS:5175242).

One BAC clone (715D09) of 110 kbp in length was identified which contained the right border of the Sm1 locus. Annotation of this BAC clone revealed two disease resistance gene analogues: RGA 1 and RGA 2 and a cysteine-rich receptor kinase gene. Real-Time PCR markers developed from the sequence of the two RGA genes (Table 1B) were genotyped on a subset of recombinant plants from the Xi19 x Robigus mapping population, which confirmed their genetic position within the interval.

RGA 1 gene is encoding a protein of sequence SEQ ID NO: 3 and RGA 2 gene is encoding a protein of sequence SEQ ID NO: 6. Both proteins have the CC, NBS, and LRR motifs of a classical CNL resistance genes as shown on FIG. 1. Interestingly the annotation of RGA 2 revealed the presence of extra domains that can also be involved in plant defense (i.e. a NAM, pKinase and a PapD-like domains). Recent studies argue that these "integrated domains" may arise from fusions between NLRs (Nucleotide-binding Leucine-rich Repeats) and that these additional domains serve as "baits" for the pathogen-derived effector proteins; thus enabling pathogen recognition (Sarris et al, 2016).

BLAST analysis of the two Robigus RGA cDNA's against the whole IWGSC WGA dataset identified a region within IWGSCWGAV02_2BS_scaffold11627 with a percentage of identity ranging from 78 to 82% for fragments larger than 700 bp. More specifically, the 1,173 and 968 nucleotides coding for the LRR domains of RGA 1 and RGA 2 respectively, have two BLAST hits each both in an interval of 141,193 bp within IWGSCWGAV02_2BS_scaffold11627 (i.e. RGA.CS1 and RGA.CS2 shown in FIG. 2). The percentages of identity of 77, 81 and 77, 27 for RGA 1 and of 81, 75 and 80, 75 for RGA 2 suggest a tandem duplication of the two ancestral RGA genes. The observed percentage of identity did not differ significantly from those obtained later by BLASTing mRNA contigs against the whole IWGSC WGA (see section entitled "Differential expression on recombinant plants"). No higher percentages of identity were identified elsewhere in the genome suggesting a co-ancestry between RGA 1 and RGA 2 and the cluster of RGA genes identified within IWGSCWGAV02_2BS_scaffold11627 (i.e. RGA.CS1 and RGA.CS2 shown in FIG. 2). The IWGSCWGAV02_2BS_scaffold11627 fragment, remaining within the Sm1 interval, was annotated based on the MAKER score and the ST/mRNAseq data was used to check the quality of the annotation. Only high confidence (HC) genes supported by functional annotation (Uniprot/Swissprot) were retained.

The 390 bp of the pkinase domain of RGA 2 matched with a percentage of identity of 96.69% to a kinase located at the recombination breakpoint on the IWGSCWGAV02_2BS_scaffold11627. The co-dominant markers listed in Table 1A are located in this pKinase domain. The cysteine-rich receptor kinase at the end of the BAC has been mapped outside the interval (FIG. 2).

Percentages of identity to other kinases present in the IWGSCWGAV02_2BS_scaffold11627 were lower than 90%. These data suggest an ancestral re-arrangement of this region in the midge resistant lines that removed nearly 600 kb between the first two Chinese Spring RGA genes (i.e. RGA.CS1 and RGA.CS2 shown in FIG. 2) and this kinase.

It should be noted that Kassa et al (2016) describe Bradi5g00870 as a putative candidate gene for Sm1, but this RGA gene sequence is not found within the target interval identified in the present invention.

Example 2: Sequencing of Robiqus and Xi19

Figure 3:
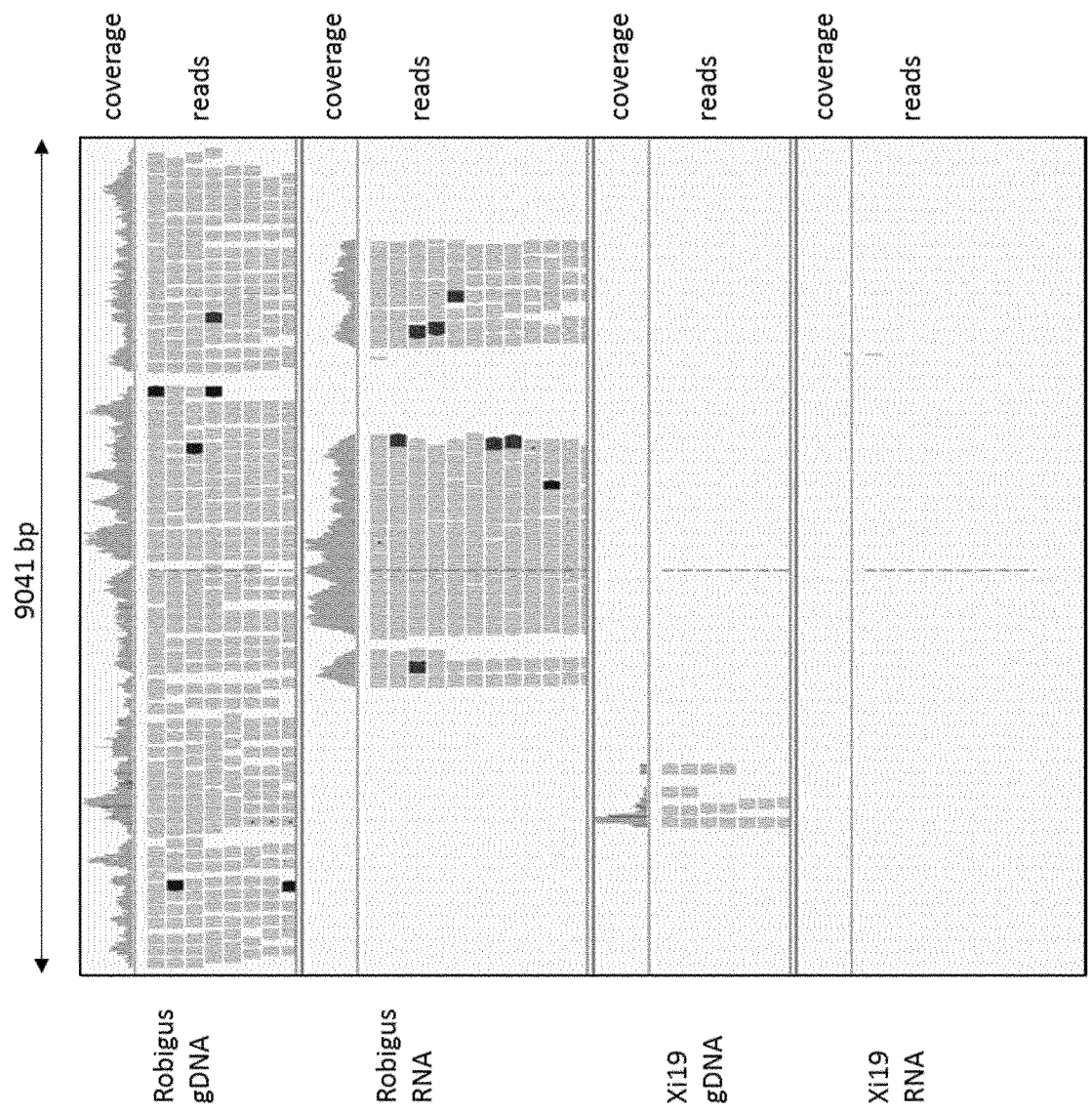
FIG. 3. An Integrative Genomics Viewer (IVG) screenshot showing the alignment of genomic (gDNA-seq) and transcriptomic (mRNA-seq) Illumina reads to the region of BAC clone 715D09 containing RGA 1.

A 30× genome coverage of both Xi19 and Robigus was generated. Bio-informatic mapping of the gDNA reads to the IWGSCWGAV02_2BS_scaffold14096, IWGSCW GAV02_2BS_scaffold11627 and the BAC sequence confirmed large structural differences in the region, which explain the observed lack of recombination. Essentially, there were no gDNA-seq reads from Xi19 that mapped onto the BAC sequence of Renan (FIG. 3). Similarly, none of the gDNA-seq reads from Robigus mapped onto scaffold11627 portion located in the interval. This indicates that the gene content of the corresponding genomic regions in susceptible and resistant plants is very divergent and this was probably caused by a local chromosomal rearrangement. Similar structural rearrangements between the Chinese Spring reference genome sequence and the region containing the *Fusarium* head blight resistance gene (Fhb1) have recently been published (Schweiger et al, 2016).

Example 3: Differential Expression on Recombinant Plants

Due to the major structural differences between 'Chinese Spring' reference genome and Renan at the Sm1 locus, the next approach taken was to sequence the transcriptome from wheat spikes taken from 12 resistant and 13 susceptible plants that had undergone a recombination event very close to the Sm1 locus, as well as the two parental lines: Xi19 and Robigus. The objective was to gather expression evidence for the candidate genes identified within the region and to check for the presence of new genes that were absent from the reference genome, but present at the Sm1 locus. The 25 selected plants, plus the parents, were sown in the field and individual spikes were sampled on dry ice, following midge attack. The mRNA was extracted from these 25 tissue samples and used for paired-end sequencing using an Illumina HiSeq 2500 sequencer, which was performed by external service provider: Service XS. The RNA-Seq Illumina data sets generated on the 25 lines were analysed to produce a de novo transcriptome assembly. The RNA-Seq reads from each individual line were then mapped back onto this de novo transcriptome assembly and the gene expression of the 12 resistant lines was compared to that of the 13 susceptible lines in order to identify differentially expressed genes.

A first screen for differentially expressed sequences, highlighted the presence of 566 genes that were annotated as insect genes and these were only found in the susceptible plant samples; thus confirming that the sampled wheat spikes had contained developing midge larvae. Therefore the absence of insect gene expression in the resistant plant samples can be interpreted as the direct effect of the Sm1 resistance locus.

Amongst the differentially expressed plant genes, six were over-expressed sequences in the resistant lines and 21 were over-expressed in the susceptible lines. The sequence of the 27 assembled EST contigs was used for BLAST analysis against both the IWGSC WGA and the BAC sequence to validate their genomic position (Table 2). Only six genes (3 over-expressed and 3 under-expressed genes), out of the total of twenty-seven, mapped to within the target interval (Table 2). The rest of contigs had BLAST hits with percentages of identity >97% to regions on other wheat chromosomes or were physically distant on the chromosome 2B (Table 2).

Table 2 below shows the chromosomal location of the 27 differentially expressed ESTs identified between the resistant and susceptible plants subjected to RNA-Seq analysis. Below "+" indicates over-expression in resistant lines and "−" indicates over-expression in susceptible lines. The IWGSC WGA hits on 2BS for EST 1, 3 and 6 identified IWGSC WGA contig IWGSCWGAV02_ 2BS_scaffold11627. EST21 (2BS*) maps more than 200 Mbps from the Sm1 locus. EST22 (RGA.Xi19) has been annotated as an RGA protein and it has 89% percentage of identity to RGA.CS1 (FIG. 2).

| Feature | Expression | | IWGSC WGA | Identity percentage with IWGSC WGA | Identity percentage with BAC 715D09 |
| --- | --- | --- | --- | --- | --- |
| EST1 | + | RGA 1 | 2BS | 78% | 100% |
| EST2 | + | | 5DL | 100% | |
| EST3 | + | RGA 2 | 2BS | 87% | 100% |
| EST4 | + | | 5BS | 98% | |
| EST5 | + | | 5DL | 100% | |
| EST6 | + | Kinase | 2BS | 77% | 100% |
| EST7 | − | | 6AL | 100% | |
| EST8 | − | | 7DL | 96% | |
| EST9 | − | | 2AL | 99% | |
| EST10 | − | | 1DS | 98% | |
| EST11 | − | | 4DL | 99% | |
| EST12 | − | | 1AL | 97% | |
| EST13 | − | | 3AL | 96% | |
| EST14 | − | | 7DL | 99% | |
| EST15 | − | | 6BS | 89% | |
| EST16 | − | | 2DL | 97% | |

-continued

| Feature | Expression | | IWGSC WGA | Identity percentage with IWGSC WGA | Identity percentage with BAC 715D09 |
| --- | --- | --- | --- | --- | --- |
| EST17 | − | | 6DL | 98% | |
| EST18 | − | | 2BL | 99% | |
| EST19 | − | | 3DL | 100% | |
| EST20 | − | | 4DL | 100% | |
| EST21 | − | | 2BS* | 99% | |
| EST22 | − | RGA.Xi19 | 2BS | 89% | |
| EST23 | − | | 6DL | 100% | |
| EST24 | − | | 3DL | 98% | |
| EST25 | − | | 4AS | 98% | |
| EST26 | − | | 2BS | 100% | |
| EST27 | − | | 2BS | 100% | |

As Sm1 resistance has been reported as being partially dominant (McKenzie et al, 2002), the following analyses focused on the six over-expressed genes. Amongst these candidates (EST1 to 6 in Table 2), three genes were located on the BAC clone (715D09). As expected, these three genes were absent from Xi19 and so it was not possible to map any of the Xi19 RNA-Seq reads to the BAC sequence. (N.B. EST1 corresponds to RGA 1 and EST 3 corresponds to RGA 2). And conversely, it was not possible to map any of the Robigus RNA-Seq reads to the IWGSCWGAV02_ 2BS_s-caffold11627 fragment that remained in the interval. The other three genes mapped, with strong BLAST hits, to chromosomes 5DL and 5BS.

Example 4: Marker Analysis Around the Sm1 Locus Using a Diverse Panel

In total, 23,400 lines were screened from crosses segregating for Sm1 with ten SNP markers distributed across the Sm1 locus in order to search for extra recombinants within this region. In total, 576 putative recombinants were identified and these, plus their parental lines, were also genotyped with two Real-Time PCR markers developed from RGA 1 and RGA 2 (Table 1B) and 46 markers that included 24 SNPs from within the interval and 22 markers tightly flanking the region. The results showed that no recombination events were found between the two RGA genes and no recombinant plants were found within the small 0.067 cM region identified in the Xi19 x Robigus bi-parental mapping population. The lack of recombination within the region is due to the absence of any sequence homology between resistant and susceptible lines. Moreover, all the lines that carried the two Robigus RGA genes shared the Robigus haplotype based on the 24 markers within the target interval suggesting a single origin and a common ancestor for the Sm1 resistance locus.

Amongst the 576 lines, a sub-panel of 113 diverse lines was selected for phenotypic analysis. This sub-panel contained many recombinant plants arising from different genetic origins in order to validate any potential diagnostic SNP markers. All the recombinant plants and their parental lines were sown and genotyped in summer 2014. The presence of the two RGA genes was always shown to be 100% diagnostic for the presence of Sm1. From these 24 markers within the interval, five were found to be correlated with the presence and absence of the two RGAs (Table 1A), which makes them ideal for marker-assisted selection of the Sm1 gene.

Example 5: Identification of Genomic Regions that have Promoter Motifs for RGA 1 and RGA 2 Genes The 715D09 BAC sequence containing the two RGA genes was submitted to the TSSP (Prediction of PLANT Promoters (Using RegSite Plant DB, Softberry Inc.)) using the algorithm as implemented on the softberry.com website.

The sequences of the arbitrary 3000 bp upstream of the translation start site (TSS) of the two genes of interest containing the predicted promoter sequences are as set forth in SEQ ID NO: 31 for RGA 1 and SEQ ID NO: 32 for RGA 2. Within those 3000 bp, for both genes, extra predicted promoter regions containing TATA box and transcription factor binding sites were identified.

The positions of predicted promoter sequences in SEQ ID NO: 31 based on TSSP algorithm are the following:
Promoter Position 285 with TATA box at position 251;
Promoter Position 1380 with TATA box at position 1364;
Promoter Position 2609 with TATA box at position 2591.

The positions of predicted promoter sequences in SEQ ID NO: 32 based on TSSP algorithm as the following:
Promoter Position 942 with TATA box at position 907;
Promoter Position 2475 with TATA box at position 2461.

Example 6: Functional Study of RGA 1 and RGA 2 Genes

Both RGA 1 and RGA 2 gene functions can be validated with different methods well known in the art. Genetic transformation of a susceptible wheat cultivar overexpressing RGA 1 or RGA 2 under different promoters can be obtained and tested for their ability to confer OWBM resistance in glass-house conditions or in the field.

Validation can also be achieved by mutagenesis with methods known from skilled person in the art, with for example, EMS treatment. The validation consists of obtaining several independent "loss-of-resistance" mutants derived from the EMS treatment of a resistant wheat cultivar and further identifying mutations within the candidate gene; thus confirming the resistance function of the gene. For example, such method is described by Periyannan et al. (2013) used to identify the wheat stem rust resistance gene Sr33.

REFERENCES

Altschul S F, Madden T L, Schaffer A A, Zhang J, Zhang Z, Miller W, Lipman D J (1997) Gapped BLAST and PSI-BLAST: a new generation of protein database search programs. Nucleic Acids Res. 25: 3389-3402

Altschul S F, Wootton J C, Gertz E M, Agarwala R, Morgulis A, Schaffer A A, Yu Y K (2005) Protein database searches using compositionally adjusted substitution matrices. The FEBS Journal 272: 5101-5109

Anderson O D, Greene F C (1989) The characterization and comparative analysis of high-molecular-weight glutenin genes from genomes A and B of hexaploid bread wheat. Theoretical and Applied Genetics 77: 689-700

Anon (2016) Orange wheat blossom midge. AHDB Information sheet N° 53 Summer 2016 (cereals.ahdb.org.uk/)

Bailey T L and Elkan C (1994) Fitting a mixture model by expression maximization to discover in biopolymers. Proceedings of the International Conference on Intelligent Systems for Molecular Biology_2: 28-36

Birkett M A, Bruce T J A, Martin J L, Smart L E, Oakley J, Wadhams L J (2004) Responses of female orange wheat blossom midge to wheat panicle volatiles. Journal of Chemical Ecology 30: 1319-1328

Blake N K, Stougaard R N, Weaver D K, Sherman J D, Lanning S P, Narouka Y, Xue Q, Martin J M, Talbert L E (2011) Identification of a quantitative trait locus for resistance to *Sitodiplosis mosellana* (Géhin), the orange wheat blossom midge, in spring wheat. Plant Breeding 130: 25-30

Bruce T J, Hooper A M, Ireland L, Jones O T, Martin J L, Smart L E, Oakley J, Wadhams L J (2007) Development of a pheromone trap monitoring system for orange wheat blossom midge, *Sitodiplosis mosellana*, in the U K. Pest Management and Science 63: 49-56

Chavalle S, Censier F, San Martin y Gomez G, De Profta M (2015) Protection of winter wheat against orange wheat blossom midge, *Sitodiplosis mosellana* (Géhin) (Diptera: Cecidomyiidae): efficacy of insecticides and cultivar resistance. Pest Management Science 71: 783-790

Christensen A H, Quail P H (1996) Ubiquitin promoter-based vectors for high-level expression of selectable and/or screenable marker genes in monocotyledonous plants. Transgenic Research 5: 213-218

Depigny-This D, Raynal M, Aspart L, Delseny M, Grellet F (1992) The cruciferin gene family in radish. Plant Molecular Biology 20: 467-479

Ding H, Lamb R J (1999) Oviposition and larval establishment of *Sitodiplosis mosellana* (Diptera: Cecidomyiidae) on wheat at different growth stages. The Canadian Entomologist 131: 475-481

Ding H, Lamb R J, Ames N (2000) Inducible production of phenolic acids in wheat and antibiotic resistance to *Sitodiplosis mosellana*. Journal of Chemical Ecology 26: 969-985

Doane J F, Olfert O O, Elliott R H, Hartley S, Meers S (2013) *Sitodiplosis mosellana* (Géhin), orange wheat blossom midge (Diptera: Cecidomyiidae). In "Biological control programmes in Canada 2001-2012". Eds P G Mason & D R Gillespie. Chapter 39, pp 272-276

Dogimont C, Chovelon V, Pauquet J, Boualem A, Bendahmane A (2014) The Vat locus encodes for a CC-NBS-LRR protein that confers resistance to *Aphis gossypii* infestation and *A. gossypii*-mediated virus resistance. The Plant Journal 80: 993-1004

Du B, Zhang W, Liu B, Hu J, Wei J, Shi Z, He R, Zhu L, Chen R, Han B, He G (2009) Identification and characterization of Bph14, a gene conferring resistance to brown planthopper in rice. Proceedings of the National Academy of Sciences USA 106: 22163-22168

Elliot R H, Mann L W (1996) Susceptibility of red spring wheat, *Triticum aestivum* L. cv. Katepwa, during heading and anthesis to damage by wheat midge, *Sitodiplosis mosellana* (Géhin) (Diptera: Cecidomyiidae). The Canadian Entomologist 128: 367-375

Ellis S A, Bruce T J A, Smart L E, Martin J A, Snape J, Self M (2009) Integrated management strategies for varieties tolerant and susceptible to wheat blossom midge. HGCA project report No. 451.

Fields S, Song O (1989) A novel genetic system to detect protein-protein interactions. Nature 340: 245-246

Gharalari A H, Fox S L, Smith M A H, Lamb R J (2009a) Ovipoistion deterrence in spring wheat, *Triticum aestivum*, against orange wheat blossom midge, *Sitodiplosis mosellana*: implications for inheritance of deterrence. Entomologia Experimentalis et Applicata 133: 74-83

Gharalari A H, Fox S L, Smith M A H, Lamb R J (2009b) The relationship between morphological traits of the spring wheat spike and oviposition deterrence to orange wheat blossom midge. Entomologia Experimentalis et Applicata 132: 182-190

Gharalari A H, Smith M A H, Fox S L,Lamb R J (2011) Volatile compounds from non-preferred wheat spikes reduce oviposition by Sitodiplosis mosellana. The Canadian Entomologist 143: 388-391

Gries R, Gries G, Khaskin G, King S, Olfert OO, Kaminski L A, Lamb R, Bennett R (2000) Sex pheromone of orange wheat blossom midge, Sitodiplosis mosellana. Naturwissenschaften 87: 450-454.

Harris M O, Stuart J J, Mohan M, Nair S, Lamb R J, Rohfritsch O (2003) Grasses and gall midges: Plant defense and insect adaptation. Annual Review of Entomology 48: 549-577

Ishida Y, Saito H, Ohta S, Hiei Y, Komari T, Kumashiro T (1996) High efficiency transformation of maize (Zea mays L.) mediated by Agrobacterium tumefaciens. Nature Biotechnology, 14: 745-750

Jouanin L, Guerche P, Pamboukdjian N, Tourneur C, Casse Delbart F, Tourneur J (1987) Structure of T-DNA in plants regenerated from roots transformed with Agrobacterium rhizogene strain A4. Molecular and General Genetics 206: 387-392

Kassa M T, Haas S, Schliephake E, Lewis C, You F M, Pozniak C J, Kramer I, Perovic D, Sharpe A G, Fobert P R, Koch M, Wise I L, Fenwick P, Berry S, Simmonds J, Hourcade D, Senellart P, Duchalais L, Robert O, Forster J, Thomas J B, Friedt W, Ordon F, Uauy C, McCartney C A (2016) A saturated SNP linkage map for the orange blossom midge resistance gene Sm1. Theoretical and Applied Genetics 129: 1507-1517

Kay R, Chan, A, Daly M, McPherson J (1987) Duplication of CaMV 35S promoter sequences creates a strong enhancer for plant genes. Science 236:1299-1302

Lamb R J, McKenzie R I H, Wise I L, Barker P S, Smith M A H (2000) Resistance to Sitodiplosis mosellana (Diptera: Cecidomyiidae) in spring wheat (Gramineae). The Canadian Entomologist 132: 591-605

Lamb R J, Smith M A H, Wise I L, Clarke P, Clarke J (2001) Oviposition deterrence to Sitodiplosis mosellana (Diptera: Cecidomyiidae): a source of resistance for durum wheat (Gramineae). The Canadian Entomologist 133: 579-591

Lamb R J, Wise I L, Smith M A H, McKenzie R I H, Thomas J, Olfert OO (2002) Oviposition deterrence against Sitodiplosis mosellana (Diptera: Cecidomyiidae) in spring wheat (Gramineae). The Canadian Entomologist 134: 85-96

Lamb R J, Sridhar P, Smith M A H, Wise I L (2003) Oviposition preference and offspring performance of a wheat midge Sitodiplosis mosellana (Géhin) (Diptera: Cecidomyiidae) on defended and less defended wheat plants. Environmental Entomology 32: 414-420

Lamb R J, Smith M A H, Wise I L, McKenzie R I H (2015) Resistance to wheat midge (Diptera: Cecidomyiidae) in winter wheat and the origins of resistance in spring wheat (Poaceae). The Canadian Entomologist 1: 1-10

McElroy D, Zhang W, Cao J, Wu R (1990) Isolation of an efficient actin promoter for use in rice transformation. The Plant Cell 2: 163-171

McKenzie R I H, Lamb R J, Aung T, Wise I L, Barker P, Olfert OO (2002) Inheritance of resistance to wheat midge, Sitodiplosis mosellana, in spring wheat. Plant Breeding 121: 383-388

Meyers B C, Dickerman A W, Michelmore R W, Sivaramakrishnan S, Sobral B W, Young N D (1999) Plant disease resistance genes encode members of an ancient and diverse protein family within the nucleotide-binding superfamily. The Plant Journal 20: 317-332.

Miller B S, Halton P (1960) The damage to wheat kernels caused by the wheat blossom midge (Sitodiplosis mosellana). Journal of Science, Food & Agriculture 12: 391-398

Mullis K B, Faloona F A (1987) Specific synthesis of DNA in vitro via a polymerase-catalyzed chain reaction. Methods in Enzymology 155:335-350

Oakley J N (1994) Orange wheat blossom midge: a literature review and survey of the 1993 outbreak. Research Review No. 28, HGCA, Hamlyn House, Highgate Hill, London, UK Oakley J N, Talbot G, Dyer C, Self M M, Freer J B S, Angus W J, Barrett J M, Feuerhelm G, Snape J, Sayers L, Bruce T J A, Smart L E, Wadhams L J (2005) Integrated control of wheat blossom midge: variety choice, use of pheromone traps and treatment thresholds. HGCA Project, Report 363

Olfert O, Elliott R H, Hartley S (2009) Non-native insects in agriculture: strategies to manage the economic and environmental impact of wheat midge, Sitodiplosis mosellana, in Saskatchewan. Biological Invasions 11: 127-133

Periyannan S, Moore J, Ayliffe M, Bansal U, Wang X, Huang L, Deal K, Luo M, Kong X, Bariana H, Mago R, McIntosh R, Dodds P, Dvorak J, Lagudah E (2013). The gene Sr33, an ortholog of barley Mla genes, encodes the wheat stem rust race Ug99. Science, 10.1126/1239028.

Robert L S, Thompson R D, Flavell R B (1989) Tissue-specific expression of a wheat high molecular weight glutenin gene in transgenic tobacco. The Plant Cell 1: 569-578

Rossi M, Goggin F L, Milligan S B, Klaoshian I, Ullman D E, Williamson V M (1998) The nematode resistance gene Mi of tomato confers resistance against the potato aphid. Proceedings of the National Academy of Sciences USA 95: 9750-9754

Sambrook J, Fritsch E F, Maniatis T (1989) Molecular cloning: a laboratory manual. Cold Spring Harbor, New York: Cold Spring Harbor Laboratory Press.

Sarris P F, Cevik V, Dagdas G, Jones J D G, Krasileva K V (2016) Comparative analysis of plant immune receptor architectures uncovers host proteins likely targeted by pathogens. BMC Biology 14:8

Schweiger W, Steiner B, Vautrin S, Nussbaumer T, Slegwart G, Zamini M, Jungreithmeier F, Gratl V, Lemmens M, Mayer K F X, Berges H, Adam G, Buerstmayr H (2016) Suppressed recombination and unique candidate genes in the divergent haplotype encoding Fhb1, a major Fusarium head blight resistance locus in wheat. Theoretical and Applied Genetics 129: 1607-1623

Sekhwal K M, Pingchuan L, Lam I, Wang X, Cloutier S, You F M (2015) Disease resistance gene analogs (RGAs) in Plants. The International Journal of Molecular Sciences 16: 19248-19290

Smith C M, Clement S L (2012) Molecular bases of plant resistance to arthropods. Annual Review of Entomology 57: 309-28

Stemmer P C (1994) DNA shuffling by random fragmentation and reassembly: In vitro recombination for molecular evolution. Proceedings of the National Academy of Sciences USA 91: 10747-10751

Till B J, Colbert T, Tompa R, Enns L C, Codomo C A, Johnson J E, Reynolds S H, Henikoff J G, Greene E A, Stein M N, Comai L, Henikoff S (2003) High-throughput TILLING for functional genomics. Plant Functional Genomics: Methods and Protocols. Edited by: Grotewald E. Clifton, NJ, Humana Press, 205-220

The International Wheat Genome Sequencing Consortium (IWGSC) (2014) A chromosome-based draft sequence of the hexaploid bread wheat (*Triticum aestivum*) genome. Science 345, Issue 6194

Thomas J, Fineberg N, Penner G, McCartney C, Aung T, Wise I, McCallum B (2005) Chromosome location and markers of Sm1: a gene of wheat that conditions antibiotic resistance to orange wheat blossom midge. Molecular Breeding 15: 183-192

Verdaquer B, de Kochko A, Beachy R N, Fauquet C (1996) Isolation and expression in transgenic tobacco and rice plants, of the cassava vein mosaic virus (CVMV) promoter. Plant Molecular Biology 31: 1129-1139

War A R, Paulraj M G, Ahmad T, Buhroo A A, Hussain B, Ignacimuthu S, Sharma H C (2012) Mechanisms of plant defense against insect herbviores. Plant Signalling & Behaviour 7: 1306-1320

Wise I, Lamb R, Smith M (2001) Domestication of wheats (Gramineae) and their susceptibility to herbivory by *Sitodiplosis mosellana* (Diptera: Cecidomyiidae). The Canadian Entomologist 133: 255-67

Zheng S (1965) Wheat Midge. Beijing: Agricultural Press.

The invention claimed is:

1. A method for detecting the resistance allele of a plant resistant to Orange wheat blossom midge (OWBM) comprising the steps of:
   a) isolating DNA genomic sequence or RNA nucleic acid from said plant,
   b) subjecting said nucleic acid to successive rounds of amplification using fluorescently labeled primers to amplify a target sequence containing the allele and
   c) detecting within the target sequence the presence of a resistance allele having the single nucleotide polymorphism selected from:
   the T at position 32 in SEQ ID NO:9,
   the G at position 85 in SEQ ID NO:11,
   the T at position 50 in SEQ ID NO:13,
   the C at position 58 in SEQ ID NO:15,
   the A at position 88 in SEQ ID NO:17,
   the C at position 90 in SEQ ID NO:19, and
   the T at position 67 in SEQ ID NO:21.

2. The method of claim 1, wherein the plant is a cereal plant.

3. The method of claim 1, wherein the plant is a wheat plant.

4. The method of claim 1, wherein the resistance allele is SEQ ID NO:9.

5. The method of claim 1, wherein the resistance allele is SEQ ID NO:11.

6. The method of claim 1, wherein the resistance allele is SEQ ID NO:13.

7. The method of claim 1, wherein the resistance allele is SEQ ID NO:15.

8. The method of claim 1, wherein the resistance allele is SEQ ID NO:17.

9. The method of claim 1, wherein the resistance allele is SEQ ID NO:19.

10. The method of claim 1, wherein the resistance allele is SEQ ID NO:21.

11. The method of claim 1, further comprising breeding the plant containing the resistance allele.

* * * * *